US007150983B2

(12) United States Patent
Georgiadis et al.

(10) Patent No.: US 7,150,983 B2
(45) Date of Patent: Dec. 19, 2006

(54) TRUNCATED AGGRECANASE MOLECULES

(75) Inventors: Katy E. Georgiadis, Belmont, MA (US); Tara K. Crawford, Cambridge, MA (US); Kathleen N. Tomkinson, Cambridge, MA (US); Lisa A. Collins-Racie, Acton, MA (US); Christopher J. Corcoran, Arlington, MA (US); Bethany A. Freeman, Arlington, MA (US); Edward R. Lavallie, Harvard, MA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/358,283

(22) Filed: Feb. 5, 2003

(65) Prior Publication Data

US 2004/0054149 A1 Mar. 18, 2004

Related U.S. Application Data

(60) Provisional application No. 60/354,592, filed on Feb. 5, 2002.

(51) Int. Cl.
*C12N 9/64* (2006.01)
*C12P 21/04* (2006.01)
*C07H 21/04* (2006.01)

(52) U.S. Cl. .................. 435/226; 435/69.7; 536/23.2
(58) Field of Classification Search ............... 435/226, 435/69.7; 536/23.2
See application file for complete search history.

(56) References Cited

U.S. PATENT DOCUMENTS

| 4,419,446 A | 12/1983 | Howley et al. |
| 4,816,567 A | 3/1989 | Cabilly et al. |
| 6,326,162 B1 | 12/2001 | Miller et al. |
| 6,391,610 B1 | 5/2002 | Apte et al. |
| 6,451,575 B1 | 9/2002 | Arner et al. |
| 6,521,436 B1 | 2/2003 | Arner et al. |

FOREIGN PATENT DOCUMENTS

| EP | 0 123 289 A2 | 10/1984 |
| EP | 0 155 476 A1 | 9/1985 |
| EP | 0 177 343 A1 | 9/1986 |
| WO | WO 86/00639 A1 | 1/1986 |
| WO | 99/05291 | 2/1999 |
| WO | WO 00/53774 | 9/2000 |
| WO | 03/062263 | 7/2003 |
| WO | 2004/011637 | 2/2004 |

OTHER PUBLICATIONS (Abbaszade et al. (1999) J.Biol. Chem., vol. 274 (33), pp. 23443-23450.*
Hurskainen et al. (J. Biol. Chem., 1999, vol. 274 (36), pp. 25555-2563.*

Altschul et al., "Basic . . . ," J.Mol. Biol., vol. 215, p. 403-410, (Oct. 5, 1990).
Ausubel, Wiley & Sons, Current Protocols in Molecular Biology, N.Y., 6.3.1-6.3.6, (1989).
Brandt and Mankin, "Pathogenesis . . . ," Textbook of Rheumatology, WB Saunders, P.A., p. 1355-1373, (1993).
Clackson et al., "Making . . . ," Nature, vol. 352, p. 624-628, (Aug. 15, 1991).
Flannery et al., "Identification . . . ," JBC, vol. 267 (No. 2), p. 1008-1014, (Jan. 15, 1992).
Fosang et al., "Neutrofil . . . ," Biochem. J., vol. 304, p. 347-351, (Dec. 1, 1994).
Gething and Sambrook, "Cell-surface . . . ," Nature, vol. 293, p. 620-625, (Oct. 22, 1981).
Gossen and Bujard, "Tight . . . ," PNAS USA, vol. 89, p. 5547-5551, (Jun. 15, 1992).
Gough et al., "Structure . . . ," EMBO J., vol. 4 (No. 3), p. 645-653, (Mar. 1985).
Hughes et al., "Monocolonal . . . ," Biochem. J., vol. 305, p. 799-804, (Feb. 1, 1995).
Jang et al., "Initiation . . . ," J. of Virol., vol. 63 (No. 4), p. 1651-1660, (Apr. 1989).
Kaufman and Sharp, "Amplification . . . ," J. Mol. Biol., vol. 159, p. 601-621, (Aug. 25, 1982).
Kaufman et al., "Coamplification . . . ," Mol. and Cellular Bio., vol. 5 (No. 7), p. 1750-1759, (Jul. 1985).
Kaufman and Sharp, "Construction . . . ," Mol. and Cellular Bio., vol. 2(No. 11), p. 1304-1319, (Nov. 1982).
Kaufman, "Identification . . . ," PNAS USA, vol. 82, p. 689-693, (Feb. 1985).
Kaufman et al., "Improved . . . ," Nuc. Acids Res., vol. 19 (No. 16), p. 4485-4490, (Aug. 25, 1991).
Kohler and Milstein, "Continuous . . . ," Nature, vol. 256, p. 495-497, (Aug. 7, 1975).
Laemmli, "Cleavage . . . ," Nature, vol. 227, p. 680-685, (Aug. 15, 1970).
Lohmander et al., "The Structure . . . ," Arthritis & Rheumatism, vol. 36 (No. 9), p. 1214-1222, (Sep. 1993).
MacLean et al., "Costs . . . ," J. of Rheumatology, vol. 25 ( No. 11), p. 2213-2218, (Nov. 1998).

(Continued)

*Primary Examiner*—Elizabeth Slobodyansky
(74) *Attorney, Agent, or Firm*—Kirkpatrick & Lockhart Nicholson Graham LLP

(57) ABSTRACT

Truncated aggrecanase proteins and nucleotides sequences encoding them as well as processes for producing them are disclosed. Additionally, aggrecanases with amino acid mutations that lead to increased stability and expression levels in comparison with wild-type or native aggrecanases are also disclosed. Aggrecanases of the invention are especially useful for development of compositions for treatment of diseases such as osteoarthritis. Methods for developing inhibitors of the aggrecanase enzymes and antibodies to the enzymes for treatment of conditions characterized by the degradation of aggrecan are also disclosed.

2 Claims, 27 Drawing Sheets

OTHER PUBLICATIONS

Maniatis et al., Molecular Cloning: A Laboratory Manual, p. 387-389, (1982).
Marks et al., "By-passing . . .," J. Mol. Biol., vol. 222, p. 581-597, (Dec. 5, 1991).
Mercuri et al., "Recombinant . . .," JBC, vol. 274 ( No. 45), p. 32387-32395, (Nov. 5, 1999).
Miller et al., "An Insect . . .," Genetic Engineering, vol. 8, Plenum Press, p. 277-298, (1986).
Morinaga et al., "Improvement . . .," Bio/Technology, 84, p. 636-639, (Jul. 1984).
Needleman and Wunsch, "A General . . .," J. Mol. Biol., vol. 48, p. 443-453, (Mar. 1970).
Oakley et al., "A Simplified . . .," Analytical Biochemistry, vol. 105, p. 361-363, (Jul. 1, 1980).
Okayama and Berg, "High-Efficiency . . .," Mol. and Cellular Bio., vol. 2 ( No. 2), p. 161-170, (Feb. 1982).
Sandy et al., "Catabolism . . .," JBC, vol. 266 ( No. 14), p. 8683-8685, (May 15, 1991).
Sandy et al., "The Structure . . .," J. Clin. Invest., vol. 89, p. 1512-1516, (May, 1992).
Steele et al., "Expression . . .," Protein Engineering, vol. 13 (No. 6), p. 397-405, (Jun. 2000).
Taniguchi et al., "Expression . . .," PNAS USA, vol. 77 ( No. 9), p. 5230-5233, (Sep. 1980).
Tortorella et al., "Purification . . .," Science, vol. 284, p. 1664-1666, (Jun. 4, 1999).
Towbin et al., "Electrophoretic . . .," PNAS USA, vol. 76 ( No. 9), p. 4350-4354, (Sep. 1979).
Urlaub and Chasin, "Isolation . . .," PNAS USA, vol. 77 ( No. 7), p. 4216-4220, (Jul. 1980).
Wong et al., "Human . . .," Science, vol. 228 ( No. 4701), p. 810-815, (May 17, 1985).
Cal, Santiago, et al., "*Cloning, Expression Analysis* . . .," GENE, vol. 283, 2002, pp. 49-62.
Cal, Santiago, et al., "*Identification, Characterization, and* . . .," The Journal of Biological Chemistry and Molecular Biology, Inc., vol. 276, No. 21, May 25, 2001, pp. 17932-17940.
Caterson, Bruce et al., "*Mechanisms Involved in Cartilage* . . .," Matrix Biology, vol. 19, 2000, pp. 333-344.
Clark, Melody et al., "*Adamts9, A Novel Member* . . .," GENOMICS, vol. 67, 2000, pp. 343-350.
Flannery, Carl et al., "*Autocatalytic Cleavage of AMAMTS-4* . . .," The Journal of Biological Chemistry, vol. 277, No. 45, Nov. 8, 2002, pp. 42775-42780.
Gao, Gui et al., "*Activation of the Proteolytic* . . .," The Journal of Biological Chemistry, vol. 277, Mar. 29, 2002, No. 13, pp. 11034-11041.
Hashimoto, Gakuji et al., "*Inhibition of Adamts4 (Aggrecanase-1)* . . .," Federation of European Biochemical Societies, vol. 494, 2001, pp. 192-195.
Kuno, Kouji et al., "*ADAMTS-1 Protein Anchors at the* . . .," The Journal of Biological Chemistry, vol. 273, No. 22, May 29, 1998, pp. 13912-13917.
Rodriguez-Manzaneque, Juan Carlos et al., "*Characterization of Meth-1/ADAMTS1* . . .," The Journal of Biological Chemistry, vol. 275, No. 43, Oct. 27, 2000, pp. 33471-33479.
Somerville, Robert et al., "*Characterization of ADAMTS-9* . . .," The Journal of Biological Chemistry, vol. 278, No. 11, Mar. 14, 2003, pp. 9503-9513.
Tortorella, Mickey et al., "*The Thrombospondin Motif of Aggrecanase-1* . . .," The Journal of Biological Chemistry, vol. 275, No. 33, Aug. 18, 2000, pp. 25791-25797.
Vazquez, Francisca et al., "*METH-1, A Human Ortholog* . . .," vol. 274, No. 33, Aug. 13, 1999, pp. 23349-23357.
Kuno et al., "ADAMTS-1 Is an Active Metalloproteinase Associated with the Extracellular Matrix," *J. Biol. Chem.*, 274(26):18821-18826, 1999.
Myers, E.W. and Miller, W., Optical alignments in linear space, *CABIOS*, 4(1):11-17 (1988).
Harlow, E. and Lane, D., *Antibodies: A Laboratory Manual*, Cold Spring Harbor Laboratory Press, Cold Spring Harbor, New York (1988).
Kashiwagi et al., "Altered proteolytic activities of ADAMTS-4 expressed by C-terminal processing," *J. Biol. Chem.*, 279(11):10109-10119 (2004).
"Partial European Search Report" Nov. 16, 2005, European patent application 03710886.7.

\* cited by examiner

Nucleic Acid sequence for full-length ADAMTS-5 protein (aggrecanase-2)
(SEQ ID NO: 1)

```
   1 cttgactcaa tcctgcaagc aagtgtgtgt gtgtccccat cccccgcccc gttaacttca
  61 tagcaaataa caaataccca taaagtccca gtcgcgcagc ccctccccgc gggcagcgca
 121 ctatgctgct cgggtggggcg tccctgctgc tgtgcgcgtt ccgcctgccc ctggccgcgg
 181 tcggccccgc cgcgacacct gcccaggata aagccgggca gcctccgact gctgcagcag
 241 ccgcccagcc ccgccggcgg caggggggagg aggtgcagga gcgagccgag cctcccggcc
 301 acccgcaccc cctggcgcag cggcgcagga gcaaggggct ggtgcagaac atcgaccaac
 361 tctactccgg cggcggcaag gtgggctacc tcgtctacgc gggcggccgg aggttcctct
 421 tggacctgga gcgagatggt tcggtgggca ttgctggctt cgtgcccgca ggaggcggga
 481 cgagtgcgcc ctggcgccac cggagccact gcttctatcg gggcacagtg gacgctagtc
 541 cccgctctct ggctgtcttt gacctctgtg ggggtctcga cggcttcttc gcggtcaagc
 601 acgcgcgcta caccctaaag ccactgctgc gcggaccctg gcggaggaa gaaaaggggc
 661 gcgtgtacgg ggatgggtcc gcacggatcc tgcacgtcta cacccgcgag ggcttcagct
 721 tcgaggccct gccgccgcgc gccagctgcg aaacccccgc gtccacaccg gaggcccacg
 781 agcatgctcc ggcgcacagc aacccgagcg gacgcgcagc actggcctcg cagctcttgg
 841 accagtccgc tctctcgccc gctggggggct caggaccgca gacgtggtgg cggcggcggc
 901 gccgctccat ctcccgggcc cgccaggtgg agctgcttct ggtggctgac gcgtccatgg
 961 cgcggttgta tggccggggc ctgcagcatt acctgctgac cctggcctcc atcgccaata
1021 ggctgtacag ccatgctagc atcgagaacc acatccgcct ggccgtggtg aaggtggtgg
1081 tgctaggcga caaggacaag agcctggaag tgagcaagaa cgctgccacc acactcaaga
1141 acttttgcaa gtggcagcac caacacaacc agctgggaga tgaccatgag gagcactacg
1201 atgcagctat cctgtttact cgggaggatt atgtgtgggca tcattcatgt gacaccctgg
1261 gaatggcaga cgttgggacc atatgttctc cagagcgcag ctgtgctgtg attgaagacg
1321 atggcctcca cgcagccttc actgtggctc acgaaatcgg acatttactt ggcctctccc
1381 atgacgattc caaattctgt gaagagacct tggttccac agaagataag cgcttaatgt
1441 cttccatcct taccagcatt gatgcatcta gccctggtc caaatgcact tcagccacca
1501 tcacagaatt cctggatgat ggccatggta actgtttgct ggacctacca cgaaagcaga
1561 tcctgggccc cgaagaactc ccaggacaga cctacgatgc cacccagcag tgcaacctga
1621 cattcgggcc tgagtactcc gtgtgtcccg gcatggatgt ctgtgctcgc ctgtggtgtg
1681 ctgtggtacg ccagggccag atggtctgtc tgaccaagaa gctgcctgcg gtggaaggga
1741 cgccttgtgg aaaggggaga atctgcctgc agggcaaatg tgtggacaaa accaagaaaa
1801 aatattattc aacgtcaagc catggcaact ggggatcttg ggatcctgg ggccagtgtt
1861 ctcgctcatg tggaggagga gtgcagtttg cctatcgtca ctgtaataac cctgctccca
1921 gaaacaacgg acgctactgc acagggaaga gggccatcta ccgctcctgc agtctcatgc
1981 cctgcccacc caatggtaaa tcatttcgtc atgaacagtg tgaggccaaa aatggctatc
2041 agtctgatgc aaaaggagtc aaaactttg tggaatgggt tcccaaatat gcaggtgtcc
2101 tgccagcgga tgtgtgcaag ctgacctgca gagccaaggg cactggctac tatgtggtat
2161 ttctccaaa ggtgaccgat ggcactgaat gtaggccgta cagtaattcc gtctgcgtcc
2221 gggggaagtg tgtgagaact ggctgtgacg catcattgg ctcaaagctg cagtatgaca
2281 agtgcggagt atgtggagga caactccag ctgtacaaa gattgttgga acctttaata
2341 agaaaagtaa gggttacact gacgtggtga ggattcctga agggcaacc cacataaaag
2401 ttcgacagtt caaagccaaa gaccagacta gattcactgc ctattagcc ctgaaaaaga
```

FIG. 1A

```
2461 aaaacggtga gtaccttatc aatggaaagt acatgatctc cacttcagag actatcattg
2521 acatcaatgg aacagtcatg aactatagcg gttggagcca cagggatgac ttcctgcatg
2581 gcatgggcta ctctgccacg aaggaaattc taatagtgca gattcttgca acagacccca
2641 ctaaaccatt agatgtccgt tatagctttt ttgttcccaa gaagtccact ccaaaagtaa
2701 actctgtcac tagtcatggc agcaataaag tgggatcaca cacttcgcag ccgcagtggg
2761 tcacgggccc atggctcgcc tgctctagga cctgtgacac aggttggcac accagaacgg
2821 tgcagtgcca ggatggaaac cggaagttag caaaaggatg tcctctctcc caaaggcctt
2881 ctgcgtttaa gcaatgcttg ttgaagaaat gttagcctgt ggttatgatc ttatgcacaa
2941 agataactgg aggattcagc accgatgcag tcgtggtgaa caggaggtct acctaacgca
3001 cagaaagtca tgcttcagtg acattgtcaa caggagtcca attatgggca gaatctgctc
3061 tctgtgacca aagaggatg tgcactgctt cacgtgacag tggtgacctt gcaatataga
3121 aaaacttggg agttattgaa catcccctgg gattacaaga aacactgatg aatgtaaaat
3181 cagggggacat ttgaagatgg cagaactgtc tcccccttgt cacctacctc tgatagaatg
3241 tctttaatgg tatcataatc attttcaccc ataatacaca gtagcttctt cttactgttt
3301 gtaaatacat tctcccttgg tatgtcactt tatatccccct ggttctatta aatatccat
3361 atatatttct ataaaaaaag tgtttgacca agtaggtct gcagctattt caacttcctt
3421 ccgtttccag aaagagctgt ggatatttta ctggaaatta agaacttgct gctgttttaa
3481 taagatgtag tatattttct gactacagga gataaaattt cagtcaaaaa accattttga
3541 cagcaagtat cttctgagaa attttgaaaa gtaaatagat ctcagtgtat ctagtcactt
3601 aaatacatac acgggttcat ttacttaaaa cctttgactg cctgtatttt tttcaggtag
3661 ctagccaaat taatgcataa tttcagatgt agaagtaggg tttgcgtgtg tgtgtgtgat
3721 catactcaag agtctaaaaa ctagtttcct tgtgttggaa atttaaaagg aaaaaaatcg
3781 tatttcactg tgttttcaat ttatattttc acaactactt tctctctcca gagctttcat
3841 ctgatatctc acaatgtatg atatacgtac aaaacacaca gcaagttttc tatcatgtcc
3901 aacacattca acactggtat acctcctacc agcaagcctt taaaatgcgt ttgtgtttgc
3961 ttatttgttt tgttcaaggg ttcagtaaga cctacaatgt tttgtatttc ttgacttatt
4021 ttattagaaa cattaaagat cacttggtag ttagccacat tgagaagtgg ttatcattgt
4081 taatgtggtt aatgccaaaa agtggttaat attaataaga ctgttccac accataggca
4141 ataatttctt aatttaaaaa atctaagtat attcctattg tactaaatat ttttcccaac
4201 tggaaagcac ttgattgtac ccgtaagtgt ttgagtgatg acatgtgatg attttcagaa
4261 agttgttgtt tttgtttcca tagcctgttt aagtaggttg taagtttgaa tagttagaca
4321 tggaaattat tttataagca cacacctaaa gatatctttt tagatgataa aatgtacacc
4381 cccccatcac caacctcaca acttagaaaa tctaagttgt ttgatttcat tgggatttct
4441 tttgttgtga aacactgcaa agccaatttt tctttataaa aattcatagt aatcctgcca
4501 aatgtgccta ttgttaaaga tttgcatgtg aagatcttag ggaaccactg tttgagttct
4561 acaagctcat gagagtttat ttttattata agatgttttt aatataaaag aattatgtaa
4621 ctgatcacta tattacatca tttcagtggg ccaggaaaat agatgtcttg ctgttttcag
4681 tattttctta agaaattgct tttaaaacaa ataattgttt tacaaaacca ataattatcc
4741 tttgaatttt catagactga ctttgctttc gacgtagaaa ttttttttc ttaataaatt
4801 atcactttga gaatgaggc ctgtacaagg ctgataacct atatgtgatg gagatcaccc
4861 aatgccaagg gcagaaagca aacctagtta aataggtgag aaaaaaaata ataatcccag
4921 tgccatttgt ctgtgcaaag agaattagga gagaggttaa tgttactttt tccatttttg
4981 gaaataattt taatcaagta actcaaatgt gacaaaattt atttttattt tttgtggtta
5041 tattcccaac aacattaaaa aatactcgag gcataaatgt agttgtctcc tactctgctt
```

FIG. 1B

```
5101 ctcttactat actcatacat ttttaatatg gtttatcaat gattcatgtt tccctcaaat
5161 agtgatggtt tacacctgtc atggaaacaa tcctagagag ctcagagcaa ttaaaccact
5221 attccatgct tttaagtagt tttctccacc tttttcttat gagtctcact agattgactg
5281 aggaatgtat gtctaaattc ctggagaaga tgatatggat tggaaactga aattcagaga
5341 aatggagtgt tcaatagata ccacgaattg tgaacaaagg gaaaattcta tacaactcaa
5401 tctaagtcag tccactttga cttcgtactg tctttcacct ttccattgtt gcatcttgaa
5461 tttttttaaaa tgtctagaat tcaggatgct aggggctact tctccaaaaa aaaaaaaaaa
5521 aaaaaaaaaa aaa
```

FIG. 1C

Amino acid sequence of full-length ADAMTS-5 protein (aggrecanase-2).
(SEQ ID NO: 2)

```
  1 mllgwaslll cafrlplaav gpaatpaqdk agqpptaaaa aqprrrqgee vqeraeppgh
 61 phplaqrrrs kglvqnidql ysgggkvgyl vyaggrrfll dlerdgsvgi agfvpagggt
121 sapwrhrshc fyrgtvdasp rslavfdlcg gldgffavkh arytlkpllr gpwaeeekgr
181 vygdgsaril hvytregfsf ealpprasce tpastpeahe hapahsnpsg raalasqlld
241 qsalspaggs gpqtwwrrrr rsisrarqve lllvadasma rlygrglqhy lltlasianr
301 lyshasienh irlavvkvvv lgdkdkslev sknaattlkn fckwqhqhnq lgddheehyd
361 aailftredl cghhscdtlg madvgticsp erscaviedd glhaaftvah eighllglsh
421 ddskfceetf gstedkrlms siltsidask pwskctsati tefldddghgn clldlprkqi
481 lgpeelpgqt ydatqqcnlt fgpeysvcpg mdvcarlwca vvrqgqmvcl tkklpavegt
541 pcgkgriclq gkcvdktkkk yystsshgnw gswgswgqcs rscgggvqfa yrhcnnpapr
601 nngryctgkr aiyrscslmp cppngksfrh eqceakngyq sdakgvktfv ewvpkyagvl
661 padvckltcr akgtgyyvvf spkvtdgtec rpysnsvcvr gkcvrtgcdg iigsklqydk
721 cgvcggdnss ctkivgtfnk kskgytdvvr ipegathikv rqfkakdqtr ftaylalkkk
781 ngeylingky mistsetiid ingtvmnysg wshrddflhg mgysatkeil ivqilatdpt
841 kpldvrysff vpkkstpkvn svtshgsnkv gshtsqpqwv tgpwlacsrt cdtgwhtrtv
901 qcqdgnrkla kgcplsqrps afkqcllkkc
```

FIG. 2

Nucleic Acid sequence of truncated aggrecanase-2 protein including
nucleotide #123 (atg) through nucleotide # 2382 (gaa) of SEQ ID NO: 1,
also referred to as nucleotide #1(atg) through nucleotide 2259 (gaa).
(SEQ ID NO: 3)

```
 123   atgctgct cggggtgggcg tccctgctgc tgtgcgcgtt ccgcctgccc ctggccgcgg
 181   tcggccccgc cgcgacacct gcccaggata aagccgggca gcctccgact gctgcagcag
 241   ccgcccagcc ccgccggcgg caggggagg aggtgcagga gcgagccgag cctcccggcc
 301   acccgcaccc cctggcgcag cggcgcagga gcaaggggct ggtgcagaac atcgaccaac
 361   tctactccgg cggcggcaag gtgggctacc tcgtctacgc gggcggccgg aggttcctct
 421   tggacctgga gcgagatggt tcggtgggca ttgctggctt cgtgcccgca ggaggcggga
 481   cgagtgcgcc ctggcgccac cggagccact gcttctatcg gggcacagtg gacgctagtc
 541   cccgctctct ggctgtcttt gacctctgtg ggggtctcga cggcttcttc gcggtcaagc
 601   acgcgcgcta caccctaaag ccactgctgc gcggaccctg gcggaggaa gaaaaggggc
 661   gcgtgtacgg ggatgggtcc gcacggatcc tgcacgtcta cacccgcgag ggcttcagct
 721   tcgaggccct gccgccgcgc ccagctgcg aaaccccgc gtccacaccg gaggcccacg
 781   agcatgctcc ggcgcacagc aacccgagcg gacgcgcagc actggccctcg cagctcttgg
 841   accagtccgc tctctcgccc gctgggggct caggaccgca gacgtggtgg cggcggcggc
 901   gccgctccat ctcccgggcc cgccaggtgg agctgcttct ggtggctgac gcgtccatgg
 961   cgcggttgta tggccggggc ctgcagcatt acctgctgac cctggcctcc atcgccaata
1021   ggctgtacag ccatgctagc atcgagaacc acatccgcct ggccgtggtg aaggtggtgg
1081   tgctaggcga caaggacaag agcctggaag tgagcaagaa cgctgccacc acactcaaga
1141   acttttgcaa gtggcagcac caacacaacc agctgggaga tgaccatgag gagcactacg
1201   atgcagctat cctgtttact cgggaggatt tatgtgggca tcattcatgt gacaccctgg
1261   gaatggcaga cgttgggacc atatgttctc cagagcgcag ctgtgctgtg attgaagacg
1321   atggcctcca cgcagccttc actgtggctc acgaaatcgg acatttactt ggcctctccc
1381   atgacgattc caaattctgt gaagagacct tggttccac agaagataag cgcttaatgt
1441   cttccatcct taccagcatt gatgcatcta gccctggtc caaatgcact tcagccacca
1501   tcacagaatt cctggatgat ggccatggta actgtttgct ggacctacca cgaaagcaga
1561   tcctgggccc cgaagaactc ccaggacaga cctacgatgc cacccagcag tgcaacctga
1621   cattcgggcc tgagtactcc gtgtgtcccg catggatgt ctgtgctcgc ctgtggtgtg
1681   ctgtggtacg ccagggccag atggtctgtc tgaccaagaa gctgcctgcg gtggaaggga
1741   cgccttgtgg aaaggggaga atctgcctgc.agggcaaatg tgtggacaaa accaagaaaa
1801   aatattattc aacgtcaagc catggcaact ggggatcttg gggatcctgg ggccagtgtt
1861   ctcgctcatg tggaggagga gtgcagtttg cctatcgtca ctgtaataac cctgctccca
1921   gaaacaacgg acgctactgc acagggaaga gggccatcta ccgctcctgc agtctcatgc
1981   cctgcccacc caatggtaaa tcatttcgtc atgaacagtg tgaggccaaa aatggctatc
2041   agtctgatgc aaaaggagtc aaaactttg tggaatgggt tcccaaatat gcaggtgtcc
2101   tgccagcgga tgtgtgcaag ctgacctgca gagccaaggg cactggctac tatgtggtat
2161   tttctccaaa ggtgaccgat ggcactgaat gtaggccgta cagtaattcc gtctgcgtcc
2221   gggggaagtg tgtgagaact ggctgtgacg gcatcattgg ctcaaagctg cagtatgaca
2281   agtgcggagt atgtggagga gacaactcca gctgtacaaa gattgttgga acctttaata
2341   agaaaagtaa gggttacact gacgtggtga ggattcctga a
```

FIG. 3

Amino Acid sequence of truncated aggrecanase-2 protein including amino acid #1 (Met) through amino acid # 753 (Glu) (SEQ ID NO: 4)

```
  1 mllgwaslll cafrlplaav gpaatpaqdk agqpptaaaa aqprrrqgee vqeraeppgh
 61 phplaqrrrs kglvqnidql ysgggkvgyl vyaggrrfll dlerdgsvgi agfvpagggt
121 sapwrhrshc fyrgtvdasp rslavfdlcg gldgffavkh arytlkpllr gpwaeeekgr
181 vygdgsaril hvytregfsf ealpprasce tpastpeahe hapahsnpsg raalasqlld
241 qsalspaggs gpqtwwrrrr rsisrarqve lllvadasma rlygrglqhy lltlasianr
301 lyshasienh irlavvkvvv lgdkdkslev sknaattlkn fckwqhqhnq lgddheehyd
361 aailftredl cghhscdtlg madvgticsp erscaviedd glhaaftvah eighllglsh
421 ddskfceetf gstedkrlms siltsidask pwskctsati teflddghgn clldlprkqi
481 lgpeelpgqt ydatqqcnlt fgpeysvcpg mdvcarlwca vvrqgqmvcl tkklpavegt
541 pcgkgriclq gkcvdktkkk yystsshgnw gswgswgqcs rscgggvqfa yrhcnnpapr
601 nngryctgkr aiyrscslmp cppngksfrh eqceakngyq sdakgvktfv ewvpkyagvl
661 padvckltcr akgtgyyvvf spkvtdgtec rpysnsvcvr gkcvrtgcdg iigsklqydk
721 cgvcggdnss ctkivgtfnk kskgytdvvr ipe
```

FIG. 4

Nucleic Acid sequence of truncated aggrecanase-2 protein including nucleotide #123 (atg) through nucleotide # 2379 (cct) of SEQ ID NO: 1, also referred to as nucleotide #1(atg) through nucleotide 2256 (cct). (SEQ ID NO: 5)

```
 123   atgctgct cgggtgggcg tccctgctgc tgtgcgcgtt ccgcctgccc ctggccgcgg
 181   tcggccccgc cgcgacacct gcccaggata aagccgggca gcctccgact gctgcagcag
 241   ccgcccagcc ccgccggcgg caggggggagg aggtgcagga gcgagccgag cctcccggcc
 301   acccgcaccc cctggcgcag cggcgcagga gcaaggggct ggtgcagaac atcgaccaac
 361   tctactccgg cggcggcaag gtgggctacc tcgtctacgc gggcggccgg aggttcctct
 421   tggacctgga gcgagatggt tcggtgggca ttgctggctt cgtgcccgca ggaggcggga
 481   cgagtgcgcc ctggcgccac cggagccact gcttctatcg gggcacagtg gacgctagtc
 541   cccgctctct ggctgtcttt gacctctgtg ggggtctcga cggcttcttc gcggtcaagc
 601   acgcgcgcta cccctaaag ccactgctgc gcggaccctg ggcggaggaa gaaaaggggc
 661   gcgtgtacgg ggatgggtcc gcacggatcc tgcacgtcta cacccgcgag ggcttcagct
 721   tcgaggccct gccgccgcgc gccagctgcg aaaccccgc gtccacaccg gaggcccacg
 781   agcatgctcc ggcgcacagc aacccgagcg gacgcgcagc actggcctcg cagctcttgg
 841   accagtccgc tctctcgccc gctggggggct caggaccgca gacgtggtgg cggcggcggc
 901   gccgctccat ctcccgggcc cgccaggtgg agctgcttct ggtggctgac gcgtccatgg
 961   cgcggttgta tggccggggc ctgcagcatt acctgctgac cctggcctcc atcgccaata
1021   ggctgtacag ccatgctagc atcgagaacc acatccgcct ggccgtggtg aaggtggtgg
1081   tgctaggcga caaggacaag agcctggaag tgagcaagaa cgctgccacc acactcaaga
1141   acttttgcaa gtggcagcac caacacaacc agctgggaga tgaccatgag gagcactacg
1201   atgcagctat cctgtttact cgggaggatt tatgtgggca tcattcatgt gacaccctgg
1261   gaatggcaga cgttgggacc atatgttctc cagagcgcag ctgtgctgtg attgaagacg
1321   atggcctcca cgcagccttc actgtggctc acgaaatcgg acatttactt ggcctctccc
1381   atgacgattc caaattctgt gaagagacct tggttccac agaagataag cgcttaatgt
1441   cttccatcct taccagcatt gatgcatcta agccctggtc caaatgcact tcagccacca
1501   tcacagaatt cctggatgat ggccatggta actgtttgct ggacctacca cgaaagcaga
1561   tcctgggccc cgaagaactc ccaggacaga cctacgatgc cacccagcag tgcaacctga
1621   cattcgggcc tgagtactcc gtgtgtccgg catggatgt ctgtgctcgc ctggtgtg
1681   ctgtggtacg ccagggccag atggtctgtc tgaccaagaa gctgcctgcg gtggaaggga
1741   cgccttgtgg aaaggggaga tctgcctgc agggcaaatg tgtggacaaa accaagaaaa
1801   aatattattc aacgtcaagc catggcaact ggggatcttg gggatcctgg ggccagtgtt
1861   ctcgctcatg tggaggagga gtgcagtttg cctatcgtca ctgtaataac cctgctccca
1921   gaaacaacgg acgctactgc acagggaaga gggccatcta ccgctcctgc agtctcatgc
1981   cctgcccacc caatggtaaa tcatttcgtc atgaacagtg tgaggccaaa atggctatc
2041   agtctgatgc aaaaggagtc aaaactttgg tggaatgggt tcccaaatat gcaggtgtcc
2101   tgccagcgga tgtgtgcaag ctgacctgca gagccaaggg cactggctac tatgtggtat
2161   tttctccaaa ggtgaccgat ggcactgaat gtaggccgta cagtaattcc gtctgcgtcc
2221   gggggaagtg tgtgagaact ggctgtgacg gcatcattgg ctcaaagctg cagtatgaca
2281   agtgcggagt atgtggagga gacaactcca gctgtacaaa gattgttgga acctttaata
2341   agaaaagtaa gggttacact gacgtggtga ggattcct
```

FIG. 5

Amino Acid sequence of truncated aggrecanase-2 protein including amino acid #1 (Met) through amino acid # 752 (Pro) (SEQ ID NO: 6)

```
  1 mllgwaslll cafrlplaav gpaatpaqdk agqpptaaaa aqprrrqgee vqeraeppgh
 61 phplaqrrrs kglvqnidql ysgggkvgyl vyaggrrfll dlerdgsvgi agfvpagggt
121 sapwrhrshc fyrgtvdasp rslavfdlcg gldgffavkh arytlkpllr gpwaeeekgr
181 vygdgsaril hvytregfsf ealpprasce tpastpeahe hapahsnpsg raalasqlld
241 qsalspaggs gpqtwwrrrr rsisrarqve lllvadasma rlygrglqhy lltlasianr
301 lyshasienh irlavvkvvv lgdkdkslev sknaattlkn fckwqhqhnq lgddheehyd
361 aailftredl cghhscdtlg madvgticsp erscaviedd glhaaftvah eighllglsh
421 ddskfceetf gstedkrlms siltsidask pwskctsati teflddghgn clldlprkqi
481 lgpeelpgqt ydatqqcnlt fgpeysvcpg mdvcarlwca vvrqgqmvcl tkklpavegt
541 pcgkgriclq gkcvdktkkk yystsshgnw gswgswgqcs rscgggvqfa yrhcnnpapr
601 nngryctgkr aiyrscslmp cppngksfrh eqceakngyq sdakgvktfv ewvpkyagvl
661 padvckltcr akgtgyyvvf spkvtdgtec rpysnsvcvr gkcvrtgcdg iigsklqydk
721 cgvcggdnss ctkivgtfnk kskgytdvvr ip
```

FIG. 6

Nucleic Acid sequence of truncated aggrecanase-2 protein including
nucleotide #123 (atg) through nucleotide #2007 (ttt) of SEQ ID NO: 1,
also referred to as nucleotide #1(atg) through nucleotide #1884 (ttt).
(SEQ ID NO: 7)

```
   1 cttgactcaa tcctgcaagc aagtgtgtgt gtgtccccat cccccgcccc gttaacttca
  61 tagcaaataa caaatacccca taaagtccca gtcgcgcagc ccctccccgc gggcagcgca
 121 ctatgctgct cgggtgggcg tccctgctgc tgtgcgcgtt ccgcctgccc ctggccgcgg
 181 tcggccccgc cgcgacacct gcccaggata aagccgggca gcctccgact gctgcagcag
 241 ccgcccagcc ccgccggcgg cagggggagg aggtgcagga gcgagccgag cctcccggcc
 301 acccgcaccc cctggcgcag cggcgcagga gcaaggggct ggtgcagaac atcgaccaac
 361 tctactccgg cggcggcaag gtgggctacc tcgtctacgc gggcggccgg aggttcctct
 421 tggacctgga gcgagatggt tcggtgggca ttgctggctt cgtgcccgca ggaggcggga
 481 cgagtgcgcc ctggcgccac cggagccact gcttctatcg gggcacagtg gacgctagtc
 541 cccgctctct ggctgtcttt gacctctgtg ggggtctcga cggcttcttc gcggtcaagc
 601 acgcgcgcta caccctaaag ccactgctgc gcggaccctg gcggaggaa gaaaagggg
 661 gcgtgtacgg ggatgggtcc gcacggatcc tgcacgtcta cacccgcgag ggcttcagct
 721 tcgaggccct gccgccgcgc gccagctgcg aaacccccgc gtccacaccg gaggcccacg
 781 agcatgctcc ggcgcacagc aacccgagcg gacgcgcagc actggcctcg cagctcttgg
 841 accagtccgc tctctcgccc gctggggct caggaccgca gacgtggtgg cggcggcggc
 901 gccgctccat ctcccgggcc cgccaggtgg agctgcttct ggtggctgac gcgtccatgg
 961 cgcggttgta tggccggggc ctgcagcatt acctgctgac cctggcctcc atcgccaata
1021 ggctgtacag ccatgctagc atcgagaacc acatccgcct ggccgtggtg aaggtggtgg
1081 tgctaggcga caaggacaag agcctggaag tgagcaagaa cgctgccacc acactcaaga
1141 acttttgcaa gtggcagcac caacacaacc agctgggaga tgaccatgag gagcactacg
1201 atgcagctat cctgttact cgggaggatt tatgtgggca tcattcatgt gacaccctgg
1261 gaatggcaga cgttgggacc atatgttctc cagagcgcag ctgtgctgtg attgaagacg
1321 atggcctcca cgcagccttc actgtggctc acgaaatcgg acatttactt ggcctctccc
1381 atgacgattc caaattctgt gaagagacct ttggttccac agaagataag cgcttaatgt
1441 cttccatcct taccagcatt gatgcatcta gccctggtc caaatgcact tcagccacca
1501 tcacagaatt cctggatgat ggccatggta actgtttgct ggacctacca cgaaagcaga
1561 tcctgggccc cgaagaactc ccaggacaga cctacgatgc cacccagcag tgcaacctga
1621 cattcgggcc tgagtactcc gtgtgtcccg gcatggatgt ctgtgctcgc ctgtggtgtg
1681 ctgtggtacg ccagggccag atggtctgtc tgaccaagaa gctgcctgcg gtggaaggga
1741 cgccttgtgg aaaggggaga atctgcctgc agggcaaatg tgtggacaaa accaagaaaa
1801 aatattattc aacgtcaagc catggcaact ggggatcttg gggatcctgg ggccagtgtt
1861 ctcgctcatg tggaggagga gtgcagtttg cctatcgtca ctgtaataac cctgctccca
1921 gaaacaacgg acgctactgc acagggaaga gggccatcta ccgctcctgc agtctcatgc
1981 cctgcccacc caatggtaaa tcattt
```

FIG. 7

Amino Acid sequence of truncated aggrecanase-2 protein including amino
acid #1 (Met) through amino acid #628 (Phe) (SEQ ID NO: 8)

```
  1 mllgwaslll cafrlplaav gpaatpaqdk agqpptaaaa aqprrrqgee vqeraeppgh
 61 phplaqrrrs kglvqnidql ysgggkvgyl vyaggrrfll dlerdgsvgi agfvpagggt
121 sapwrhrshc fyrgtvdasp rslavfdlcg gldgffavkh arytlkpllr gpwaeeekgr
181 vygdgsaril hvytregfsf ealpprasce tpastpeahe hapahsnpsg raalasqlld
241 qsalspaggs gpqtwwrrrr rsisrarqve lllvadasma rlygrglqhy lltlasianr
301 lyshasienh irlavvkvvv lgdkdkslev sknaattlkn fckwqhqhnq lgddheehyd
361 aailftredl cghhscdtlg madvgticsp erscaviedd glhaaftvah eighllglsh
421 ddskfceetf gstedkrlms siltsidask pwskctsati teflddghgn clldlprkqi
481 lgpeelpgqt ydatqqcnlt fgpeysvcpg mdvcarlwca vvrqgqmvcl tkklpavegt
541 pcgkgriclq gkcvdktkkk yystsshgnw gswgswgqcs rscgggvqfa yrhcnnpapr
601 nngryctgkr aiyrscslmp cppngksf
```

FIG. 8

Nucleic Acid sequence of truncated aggrecanase-2 protein including nucleotide #123 (atg) through nucleotide #1824 (cat) of SEQ ID NO: 1, also referred to as nucleotide #1(atg) through nucleotide #1701 (cat) (SEQ ID NO: 9)

```
 123   atgctgct cggggtgggcg tccctgctgc tgtgcgcgtt ccgcctgccc ctggccgcgg
 181   tcggccccgc cgcgacacct gcccaggata aagccgggca gcctccgact gctgcagcag
 241   ccgcccagcc ccgccggcgg caggggagg aggtgcagga gcgagccgag cctcccggcc
 301   acccgcaccc cctggcgcag cggcgcagga gcaagggggct ggtgcagaac atcgaccaac
 361   tctactccgg cggcggcaag gtgggctacc tcgtctacgc gggcggccgg aggttcctct
 421   tggacctgga gcgagatggt tcggtgggca ttgctggctt cgtgcccgca ggaggcggga
 481   cgagtgcgcc ctggcgccac cggagccact gcttctatcg gggcacagtg gacgctagtc
 541   cccgctctct ggctgtcttt gacctctgtg ggggtctcga cggcttcttc gcggtcaagc
 601   acgcgcgcta caccctaaag ccactgctgc gcggaccctg ggcggaggaa gaaaaggggc
 661   gcgtgtacgg ggatgggtcc gcacggatcc tgcacgtcta cacccgcgag ggcttcagct
 721   tcgaggccct gccgccgcgc gccagctgcg aaaccccgc gtccacaccg gaggcccacg
 781   agcatgctcc ggcgcacagc aacccgagcg gacgcgcagc actggcctcg cagctcttgg
 841   accagtccgc tctctcgccc gctgggggct caggaccgca gacgtggtgg cggcggcggc
 901   gccgctccat ctcccgggcc cgccaggtgg agctgcttct ggtggctgac gcgtccatgg
 961   cgcggttgta tggccggggc ctgcagcatt acctgctgac cctggcctcc atcgccaata
1021   ggctgtacag ccatgctagc atcgagaacc acatccgcct ggccgtggtg aaggtggtgg
1081   tgctaggcga caaggacaag agcctggaag tgagcaagaa cgctgccacc acactcaaga
1141   acttttgcaa gtggcagcac caacacaacc agctgggaga tgaccatgag gagcactacg
1201   atgcagctat cctgtttact cgggaggatt tatgtgggca tcattcatgt gacaccctgg
1261   gaatggcaga cgttgggacc atatgttctc cagagcgcag ctgtgctgtg attgaagacg
1321   atggcctcca cgcagccttc actgtggctc acgaaatcgg acatttactt ggcctctccc
1381   atgacgattc caaattctgt gaagagacct tggttccac agaagataag cgcttaatgt
1441   cttccatcct taccagcatt gatgcatcta gccctggtc caaatgcact tcagccacca
1501   tcacagaatt cctggatgat ggccatggta actgtttgct ggacctacca cgaaagcaga
1561   tcctgggccc cgaagaactc ccaggacaga cctacgatgc cacccagcag tgcaacctga
1621   cattcgggcc tgagtactcc gtgtgtcccg gcatggatgt ctgtgctcgc ctgtggtgtg
1681   ctgtggtacg ccagggccag atggtctgtc tgaccaagaa gctgcctgcg gtggaaggga
1741   cgccttgtgg aaaggggaga atctgcctgc agggcaaatg tgtggacaaa accaagaaaa
1801   aatattattc aacgtcaagc cat
```

FIG. 9

Amino Acid sequence of truncated aggrecanase-2 protein including amino acid #1 (Met) through amino acid #567 (His) (SEQ ID NO: 10)

```
  1 mllgwaslll cafrlplaav gpaatpaqdk agqpptaaaa aqprrrqgee vqeraeppgh
 61 phplaqrrrs kglvqnidql ysgggkvgyl vyaggrrfll dlerdgsvgi agfvpagggt
121 sapwrhrshc fyrgtvdasp rslavfdlcg gldgffavkh arytlkpllr gpwaeeekgr
181 vygdgsaril hvytregfsf ealpprasce tpastpeahe hapahsnpsg raalasqlld
241 qsalspaggs gpqtwwrrrr rsisrarqve lllvadasma rlygrglqhy lltlasianr
301 lyshasienh irlavvkvvv lgdkdkslev sknaattlkn fckwqhqhnq lgddheehyd
361 aailftredl cghhscdtlg madvgticsp erscaviedd glhaaftvah eighllglsh
421 ddskfceetf gstedkrlms siltsidask pwskctsati teflddghgn clldlprkqi
481 lgpeelpgqt ydatqqcnlt fgpeysvcpg mdvcarlwca vvrqgqmvcl tkklpavegt
541 pcgkgriclq gkcvdktkkk yystssh
```

FIG. 10

Amino acid sequence of full-length aggrecanase-1 protein (SEQ ID NO: 11)

```
  1 msqtgshpgr glagrwlwga qpclllpivp lswlvwllll llasllpsar lasplpreee
 61 ivfpeklngs vlpgsgtpar llcrlqafge tllleleqds gvqvegltvq ylgqapellg
121 gaepgtyltg tingdpesva slhwdggall gvlqyrgael hlqpleggtp nsaggpgahi
181 lrrkspasgq gpmcnvkapl gspsprprra krfaslsrfv etlvvaddkm aafhgaglkr
241 ylltvmaaaa kafkhpsirn pvslvvtrlv ilgsgeegpq vgpsaaqtlr sfcawqrgln
301 tpedsdpdhf dtailftrqd lcgvstcdtl gmadvgtvcd parscaived dglqsaftaa
361 helghvfnml hdnskpcisl ngplstsrhv mapvmahvdp eepwspcsar fitdfldngy
421 ghclldkpea plhlpvtfpg kdydadrqcq ltfgpdsrhc pqlpppcaal wcsghlngha
481 mcqtkhspwa dgtpcgpaqa cmggrclhmd qlqdfnipqa ggwgpwgpwg dcsrtcgggv
541 qfssrdctrp vprnggkyce grrtrfrscn tedcptgsal tfreeqcaay nhrtdlfksf
601 pgpmdwvpry tgvapqdqck ltcqaralgy yyvleprvvd gtpcspdsss vcvqgrciha
661 gcdriigskk kfdkcmvcgg dgsgcskqsg sfrkfrygyn nvvtipagat hilvrqqgnp
721 ghrsiylalk lpdgsyalng eytlmpsptd vvlpgavslr ysgataaset lsghgplaqp
781 ltlqvlvagn pqdtrlrysf fvprptpstp rptpqdwlhr raqileilrr rpwagrk
```

FIG. 11

Amino Acid sequence of truncated aggrecanase-1 protein including amino acid #1 (Met) through amino acid #575 (Pro) (SEQ ID NO: 12)

```
  1 msqtgshpgr glagrwlwga qpclllpivp lswlvwllll llasllpsar lasplpreee
 61 ivfpeklngs vlpgsgtpar llcrlqafge tllleleqds gvqvegltvq ylgqapellg
121 gaepgtyltg tingdpesva slhwdggall gvlqyrgael hlqpleggtp nsaggpgahi
181 lrrkspasgq gpmcnvkapl gspsprprra krfaslsrfv etlvvaddkm aafhgaglkr
241 ylltvmaaaa kafkhpsirn pvslvvtrlv ilgsgeegpq vgpsaaqtlr sfcawqrgln
301 tpedsdpdhf dtailftrqd lcgvstcdtl gmadvgtvcd parscaived dglqsaftaa
361 helghvfnml hdnskpcisl ngplstsrhv mapvmahvdp eepwspcsar fitdfldngy
421 ghclldkpea plhlpvtfpg kdydadrqcq ltfgpdsrhc pqlpppcaal wcsghlngha
481 mcqtkhspwa dgtpcgpaqa cmggrclhmd qlqdfnipqa ggwgpwgpwg dcsrtcgggv
541 qfssrdctrp vprnggkyce grrtrfrscn tedcp
```

FIG. 12

Amino Acid sequence of truncated aggrecanase-1 protein including amino acid #1 (Met) through amino acid #520(Ala) (SEQ ID NO: 13)

```
  1 msqtgshpgr glagrwlwga qpclllpivp lswlvwllll llasllpsar lasplpreee
 61 ivfpeklngs vlpgsgtpar llcrlqafge tllleleqds gvqvegltvq ylgqapellg
121 gaepgtyltg tingdpesva slhwdggall gvlqyrgael hlqpleggtp nsaggpgahi
181 lrrkspasgq gpmcnvkapl gspsprprra krfaslsrfv etlvvaddkm aafhgaglkr
241 ylltvmaaaa kafkhpsirn pvslvvtrlv ilgsgeegpq vgpsaaqtlr sfcawqrgln
301 tpedsdpdhf dtailftrqd lcgvstcdtl gmadvgtvcd parscaived dglqsaftaa
361 helghvfnml hdnskpcisl ngplstsrhv mapvmahvdp eepwspcsar fitdfldngy
421 ghclldkpea plhlpvtfpg kdydadrqcq ltfgpdsrhc pqlpppcaal wcsghlngha
481 mcqtkhspwa dgtpcgpaqa cmggrclhmd qlqdfnipqa
```

FIG. 13

Nucleic acid sequence of a recombinant truncated aggrecanase-2 protein
comprising a peptide linker and a streptavidin tag

```
gaattcccaccatgctgctcgggtgggcg tccctgctgc tgtgcgcgtt ccgcctgccc ctggccgcgg
tcggccccgc cgcgacacct gcccaggata agccgggca gcctccgact gctgcagcag
ccgcccagcc ccgccggcgg caggggagg aggtgcagga gcgagccgag cctcccggcc
acccgcaccc cctggcgcag cggcgcagga gcaaggggct ggtgcagaac atcgaccaac
tctactccgg cggcggcaag gtgggctacc tcgtctacgc gggcggccgg aggttcctct
tggacctgga gcgagatggt tcggtgggca ttgctggctt cgtgcccgca ggaggcggga
cgagtgcgcc ctggcgccac cggagccact gcttctatcg gggcacagtg gacgctagtc
cccgctctct ggctgtcttt gacctctgtg ggggtctcga cggcttcttc gcggtcaagc
acgcgcgcta cacctaaag ccactgctgc gcggaccctg ggcggaggaa gaaaaggggc
gcgtgtacgg ggatgggtcc gcacggatcc tgcacgtcta cacccgcgag ggcttcagct
tcgaggccct gccgccgcgc gccagctgcg aaaccccgc gtccacaccg gaggcccacg
agcatgctcc ggcgcacagc aacccgagcg gacgcgcagc actggcctcg cagctcttgg
accagtccgc tctctcgccc gctgggggct caggaccgca gacgtggtgg cggcggcggc
gccgctccat ctcccgggcc cgccaggtgg agctgcttct ggtggctgac gcgtccatgg
cgcggttgta tggccggggc ctgcagcatt acctgctgac cctggcctcc atcgccaata
ggctgtacag ccatgctagc atcgagaacc acatccgcct ggccgtggtg aaggtggtgg
tgctaggcga caaggacaag agcctggaag tgagcaagaa cgctgccacc acactcaaga
actttttgcaa gtggcagcac caacacaacc agctgggaga tgaccatgag gagcactacg
atgcagctat cctgtttact cgggaggatt tatgtgggca tcattcatgt gacaccctgg
gaatggcaga cgttgggacc atatgttctc cagagcgcag ctgtgctgtg attgaagacg
atggcctcca cgcagccttc actgtggctc acgaaatcgg acatttactt ggcctctccc
atgacgattc caaattctgt gaagagacct ttggttccac agaagataag cgcttaatgt
cttccatcct taccagcatt gatgcatcta gccctggtc caaatgcact tcagccacca
tcacagaatt cctggatgat ggccatggta actgtttgct ggacctacca cgaaagcaga
tcctgggccc cgaagaactc ccaggacaga cctacgatgc cacccagcag tgcaacctga
cattcgggcc tgagtactcc gtgtgtcccg gcatggatgt ctgtgctcgc ctgtggtgtg
ctgtggtacg ccagggccag atggtctgtc tgaccaagaa gctgcctgcg gtggaaggga
cgccttgtgg aaaggggaga atctgcctgc agggcaaatg tgtggacaaa accaagaaaa
aatattattc aacgtcaagc catggcaact ggggatcttg gggatcctgg ggccagtgtt
ctcgctcatg tggaggagga gtgcagtttg cctatcgtca ctgtaataac cctgctccca
gaaacaacgg acgctactgc acagggaaga gggccatcta ccgctcctgc agtctcatgc
cctgcccacc caatggtaaa tcatttcgtc atgaacagtg tgaggccaaa aatggctatc
agtctgatgc aaaaggagtc aaaactttg tggaatgggt tcccaaatat gcaggtgtcc
tgccagcgga tgtgtgcaag ctgacctgca gagccaaggg cactggctac tatgtggtat
tttctccaaa ggtgaccgat ggcactgaat gtaggccgta cagtaattcc gtctgcgtcc
gggggaagtg tgtgagaact ggctgtgacg gcatcattgg ctcaaagctg cagtatgaca
agtgcggagt atgtggagga gacaactcca gctgtacaaa gattgttgga acctttaata
agaaaagtaa gggttacact gacgtggtga ggattcctgg atccggatct gcttggagcc
acccgcagtt cgaaaaataaggcggccgc
```

FIG. 14

Amino Acid sequence of truncated aggrecanase-2 protein including a
peptide linker and a streptavidin tag
(SEQ ID NO: 15)

```
  1 mllgwaslll cafrlplaav gpaatpaqdk agqpptaaaa aqprrrqgee vqeraeppgh
 61 phplaqrrrs kglvqnidql ysgggkvgyl vyaggrrfll dlerdgsvgi agfvpagggt
121 sapwrhrshc fyrgtvdasp rslavfdlcg gldgffavkh arytlkpllr gpwaeeekgr
181 vygdgsaril hvytregfsf ealpprasce tpastpeahe hapahsnpsg raalasqlld
241 qsalspaggs gpqtwwrrrr rsisrarqve lllvadasma rlygrglqhy lltlasianr
301 lyshasienh irlavvkvvv lgdkdkslev sknaattlkn fckwqhqhnq lgddheehyd
361 aailftredl cghhscdtlg madvgticsp erscaviedd glhaaftvah eighllglsh
421 ddskfceetf gstedkrlms siltsidask pwskctsati teflddghgn clldlprkqi
481 lgpeelpgqt ydatqqcnlt fgpeysvcpg mdvcarlwca vvrqgqmvcl tkklpavegt
541 pcgkgriclq gkcvdktkkk yystsshgnw gswgswgqcs rscgggvqfa yrhcnnpapr
601 nngryctgkr aiyrscslmp cppngksfrh eqceakngyq sdakgvktfv ewvpkyagvl
661 padvckltcr akgtgyyvvf spkvtdgtec rpysnsvcvr gkcvrtgcdg iigsklqydk
721 cgvcggdnss ctkivgtfnk kskgytdvvr ipgsawshpqfek
```

FIG. 15

Aggrecanase activity of conditioned medium from CHO cells expressing wild-type (ADAMTS-5 WT) or active-site mutant (ADAMTS-5 ASM) as detected by an ELISA assay.

Amino acid sequence of full-length ADAMTS-5 protein with an E to Q mutation at amino acid 411. (SEQ ID NO: 30)

```
  1 mllgwaslll cafrlplaav gpaatpaqdk agqpptaaaa aqprrrqgee vqeraeppgh
 61 phplaqrrrs kglvqnidql ysgggkvgyl vyaggrrfll dlerdgsvgi agfvpagggt
121 sapwrhrshc fyrgtvdasp rslavfdlcg gldgffavkh arytlkpllr gpwaeeekgr
181 vygdgsaril hvytregfsf ealpprasce tpastpeahe hapahsnpsg raalasqlld
241 qsalspaggs gpqtwwrrrr rsisrarqve lllvadasma rlygrglqhy lltlasianr
301 lyshasienh irlavvkvvv lgdkdkslev sknaattlkn fckwqhqhnq lgddheehyd
361 aailftredl cghhscdtlg madvgticsp erscaviedd glhaaftvah qighllglsh
421 ddskfceetf gstedkrlms siltsidask pwskctsati teflddghgn clldlprkqi
481 lgpeelpgqt ydatqqcnlt fgpeysvcpg mdvcarlwca vvrqgqmvcl tkklpavegt
541 pcgkgriclq gkcvdktkkk yystsshgnw gswgswgqcs rscgggvqfa yrhcnnpapr
601 nngryctgkr aiyrscslmp cppngksfrh eqceakngyq sdakgvktfv ewvpkyagvl
661 padvckltcr akgtgyyvvf spkvtdgtec rpysnsvcvr gkcvrtgcdg iigsklqydk
721 cgvcggdnss ctkivgtfnk kskgytdvvr ipegathikv rqfkakdqtr ftaylalkkk
781 ngeylingky mistsetiid ingtvmnysg wshrddflhg mgysatkeil ivqilatdpt
841 kpldvrysff vpkkstpkvn svtshgsnkv gshtsqpqwv tgpwlacsrt cdtgwhtrtv
901 qcqdgnrkla kgcplsqrps afkqcllkkc
```

FIG. 21

Nucleic Acid sequence of aggrecanase-1. (SEQ ID NO: 31)

```
   1 cacagacaca tatgcacgag agagacagag gaggaaagag acagagacaa aggcacagcg
  61 gaagaaggca gagacagggc aggcacagaa gcggcccaga cagagtccta cagagggaga
 121 ggccagagaa gctgcagaag acacaggcag ggagagacaa agatccagga aaggagggct
 181 caggaggaga gtttggagaa gccagacccc tgggcacctc tcccaagccc aaggactaag
 241 ttttctccat ttcctttaac ggtcctcagc ccttctgaaa actttgcctc tgaccttggc
 301 aggagtccaa gcccccaggc tacagagagg agctttccaa agctagggtg tggaggactt
 361 ggtgccctag acggcctcag tccctcccag ctgcagtacc agtgccatgt cccagacagg
 421 ctcgcatccc ggggaggggct tggcagggcg ctggctgtgg ggagcccaac cctgcctcct
 481 gctccccatt gtgccgctct cctggctggt gtggctgctt ctgctactgc tggcctctct
 541 cctgccctca gcccggctgg ccagcccct ccccgggag gaggagatcg tgtttccaga
 601 gaagctcaac ggcagcgtcc tgcctggctc gggcacccct gccaggctgt tgtgccgctt
 661 gcaggccttt ggggagacgc tgctactaga gctggagcag gactccggtg tgcaggtcga
 721 ggggctgaca gtgcagtacc tgggccaggc gcctgagctg ctgggtggag cagagcctgg
 781 cacctacctg actggcacca tcaatggaga tccggagtcg gtggcatctc tgcactggga
 841 tgggggagcc ctgttaggcg tgttacaata tcgggggggct gaactccacc tccagcccct
 901 ggagggaggc acccctaact ctgctggggg acctggggct cacatcctac gccggaagag
 961 tcctgccagc ggtcaaggtc ccatgtgcaa cgtcaaggct cctcttggaa gccccagccc
1021 cagaccccga agagccaagc gctttgcttc actgagtaga tttgtggaga cactggtggt
1081 ggcagatgac aagatggccg cattccacgg tgcggggcta aagcgctacc tgctaacagt
1141 gatggcagca gcagccaagg ccttcaagca cccaagcatc cgcaatcctg tcagcttggt
1201 ggtgactcgg ctagtgatcc tggggtcagg cgaggagggg ccccaagtgg ggcccagtgc
1261 tgcccagacc ctgcgcagct tctgtgcctg gcagcggggc ctcaacaccc ctgaggactc
1321 ggaccctgac cactttgaca cagccattct gtttacccgt caggacctgt gtggagtctc
1381 cacttgcgac acgctgggta tggctgatgt gggcaccgtc tgtgacccgg ctcggagctg
1441 tgccattgtg gaggatgatg ggctccagtc agccttcact gctgctcatg aactgggtca
1501 tgtcttcaac atgctccatg acaactccaa gccatgcatc agtttgaatg ggcctttgag
1561 cacctctcgc catgtcatgg cccctgtgat ggctcatgtg gatcctgagg agccctggtc
1621 cccctgcagt gcccgcttca tcactgactt cctggacaat ggctatgggc actgtctctt
1681 agacaaacca gaggctccat gcatctgcc tgtgactttc cctggcaagg actatgatgc
1741 tgaccgccag tgccagctga ccttcgggcc cgactcacgc attgtccac agctgccgcc
1801 gccctgtgct gccctctggt gctctggcca cctcaatggc catgccatgt gccagaccaa
1861 acactcgccc tgggccgatg cacaccctg cgggcccgca caggcctgca tgggtggtcg
1921 ctgcctccac atggaccagc tccaggactt caatattcca caggctggtg gctggggtcc
1981 ttggggacca tggggtgact gctctcggac ctgtggggt ggtgtccagt tctcctcccg
2041 agactgcacg aggcctgtcc cccggaatgg tgcaagtac tgtgagggcc gccgtacccg
2101 cttccgctcc tgcaacactg aggactgccc aactggctca gccctgacct tccgcgagga
2161 gcagtgtgct gcctacaacc accgcaccga cctcttcaag agcttcccag ggcccatgga
2221 ctgggttcct cgctacacag gcgtggcccc ccaggaccag tgcaaactca cctgccaggc
2281 ccggcactg ggctactact atgtgctgga gccacgggtg gtagatggga cccctgttc
2341 cccggacagc tcctcggtct gtgtccaggg ccgatgcatc catgctggct gtgatcgcat
2401 cattggctcc aagaagaagt tgacaagtg catggtgtgc ggaggggacg gttctggttg
2461 cagcaagcag tcaggctcct tcaggaaatt caggtacgga tacaacaatg tggtcactat
```

FIG. 22A

```
2521 ccccgcgggg gccacccaca ttcttgtccg gcagcaggga aaccctggcc accggagcat
2581 ctacttggcc ctgaagctgc cagatggctc ctatgccctc aatggtgaat acacgctgat
2641 gccctcccccc acagatgtgg tactgcctgg ggcagtcagc ttgcgctaca gcggggccac
2701 tgcagcctca gagacactgt caggccatgg gccactggcc cagcctttga cactgcaagt
2761 cctagtggct ggcaaccccc aggacacacg cctccgatac agcttcttcg tgccccggcc
2821 gacccccttca acgccacgcc ccactcccca ggactggctg caccgaagag cacagattct
2881 ggagatcctt cggcggcgcc cctgggcggg caggaaataa cctcactatc ccggctgccc
2941 tttctgggca ccggggcctc ggacttagct gggagaaaga gagagcttct gttgctgcct
3001 catgctaaga ctcagtgggg aggggctgtg ggcgtgagac ctgcccctcc tctctgccct
3061 aatgcgcagg ctggccctgc cctggtttcc tgccctggga ggcagtgatg ggttagtgga
3121 tggaaggggc tgacagacag ccctccatct aaactgcccc ctctgccctg cgggtcacag
3181 gagggagggg gaaggcaggg agggcctggg ccccagttgt atttatttag tatttattca
3241 cttttattta gcaccaggga aggggacaag gactagggtc ctggggaacc tgaccccctga
3301 cccctcatag ccctcacccct ggggctagga aatccagggt ggtggtgata ggtataagtg
3361 gtgtgtgtat gcgtgtgtgt gtgtgtgtga aaatgtgtgt gtgcttatgt atgaggtaca
3421 acctgttctg ctttcctctt cctgaatttt attttttggg aaaagaaaag tcaagggtag
3481 ggtgggccctt caggggagtga gggattatct ttttttttt ttctttcttt ctttctttt
3541 ttttttgag acagaatctc gctctgtcgc ccaggctgga gtgcaatggc acaatctcgg
3601 ctcactgcat cctccgcctc ccgggttcaa gtgattctca tgcctcagcc tcctgagtag
3661 ctgggattac aggctcctgc caccacgccc agctaatttt tgttttgttt tgtttggaga
3721 cagagtctcg ctattgtcac cagggctgga atgatttcag ctcactgcaa ccttcgccac
3781 ctgggttcca gcaattctcc tgcctcagcc tcccgagtag ctgagattat aggcacctac
3841 caccacgccc ggctaatttt tgtatttta gtagagacgg ggtttcacca tgttggccag
3901 gctggtctcg aactcctgac cttaggtgat ccactcgcct tcatctccca aagtgctggg
3961 attacaggcg tgagccaccg tgcctggcca cgcccaacta ttttttgtat ttttagtaga
4021 gacagggttt caccatgttg gccaggctgc tcttgaactc ctgacctcag gtaatcgacc
4081 tgcctcggcc tcccaaagtg ctgggattac aggtgtgagc caccacgccc ggtacatatt
4141 ttttaaattg aattctacta tttatgtgat ccttttggag tcagacagat gtggttgcat
4201 cctaactcca tgtctctgag cattagattt ctcatttgcc aataataata cctccccttag
4261 aagtttgttg tgaggattaa ataatgtaaa taaagaacta gcataac
```

FIG. 22B

Nucleic acid sequence of a truncated aggrecanase-1 molecule encoding, for example, the protein set forth in Figure 12 (SEQ ID NO: 32)

```
                                             atgt cccagacagg
ctcgcatccc gggaggggct tggcagggcg ctggctgtgg ggagcccaac cctgcctcct
gctccccatt gtgccgctct cctggctggt gtggctgctt ctgctactgc tggcctctct
cctgccctca gcccggctgg ccagccccct ccccgggag gaggagatcg tgtttccaga
gaagctcaac ggcagcgtcc tgcctggctc gggcaccccct gccaggctgt tgtgccgctt
gcaggccttt ggggagacgc tgctactaga gctggagcag gactccggtg tgcaggtcga
ggggctgaca gtgcagtacc tgggccaggc gcctgagctg ctgggtggag cagagcctgg
cacctacctg actggcacca tcaatggaga tccggagtcg gtggcatctc tgcactggga
tgggggagcc ctgttaggcg tgttacaata tcgggggggct gaactccacc tccagcccct
ggagggaggc accccctaact ctgctgggggg acctggggct cacatcctac gccggaagag
tcctgccagc ggtcaaggtc ccatgtgcaa cgtcaaggct cctcttggaa gccccagccc
cagaccccga agagccaagc gctttgcttc actgagtaga tttgtggaga cactggtggt
ggcagatgac aagatggccg cattccacgg tgcggggcta aagcgctacc tgctaacagt
gatggcagca gcagccaagg ccttcaagca cccaagcatc cgcaatcctg tcagcttggt
ggtgactcgg ctagtgatcc tggggtcagg cgaggagggg ccccaagtgg ggcccagtgc
tgcccagacc ctgcgcagct tctgtgcctg gcagcggggc ctcaacaccc ctgaggactc
ggaccctgac cactttgaca cagccattct gtttacccgt caggacctgt gtggagtctc
cacttgcgac acgctgggta tggctgatgt gggcaccgtc tgtgacccgg ctcggagctg
tgccattgtg gaggatgatg ggctccagtc agccttcact gctgctcatg aactgggtca
tgtcttcaac atgctccatg acaactccaa gccatgcatc agtttgaatg gcctttgag
cacctctcgc catgtcatgg cccctgtgat ggctcatgtg gatcctgagg agccctggtc
ccctgcagt gcccgcttca tcactgactt cctggacaat ggctatgggc actgtctctt
agacaaacca gaggctccat tgcatctgcc tgtgactttc cctggcaagg actatgatgc
tgaccgccag tgccagctga ccttcgggcc cgactcacgc cattgtccac agctgccgcc
gccctgtgct gccctctggt gctctggcca cctcaatggc catgccatgt gccagaccaa
acactcgccc tgggccgatg cacaccctg cgggcccgca caggcctgca tgggtggtcg
ctgcctccac atggaccagc tccaggactt caatattcca caggctggtg gctggggtcc
ttggggacca tggggtgact gctctcggac ctgtgggggt ggtgtccagt tctcctcccg
agactgcacg aggcctgtcc cccggaatgg tggcaagtac tgtgagggcc gccgtacccg
cttccgctcc tgcaacactg aggactgccc a
```

FIG. 23

Nucleic acid sequence of a truncated aggrecanase-1 molecule encoding, for example, the protein set forth in Figure 13. (SEQ ID NO: 33)

```
                                               atgt cccagacagg
ctcgcatccc gggaggggct tggcagggcg ctggctgtgg ggagcccaac cctgcctcct
gctcccatt  gtgccgctct cctggctggt gtggctgctt ctgctactgc tggcctctct
cctgccctca gcccggctgg ccagccccct cccccgggag gaggagatcg tgtttccaga
gaagctcaac ggcagcgtcc tgcctggctc gggcacccct gccaggctgt tgtgccgctt
gcaggccttt ggggagacgc tgctactaga gctggagcag gactccggtg tgcaggtcga
ggggctgaca gtgcagtacc tgggccaggc gcctgagctg ctgggtggag cagagcctgg
cacctacctg actggcacca tcaatggaga tccggagtcg gtggcatctc tgcactggga
tggggagcc  ctgttaggcg tgttacaata tcgggggggct gaactccacc tccagcccct
ggagggaggc acccctaact ctgctggggg acctggggct cacatcctac gccggaagag
tcctgccagc ggtcaaggtc ccatgtgcaa cgtcaaggct cctcttggaa gccccagccc
cagaccccga agagccaagc gctttgcttc actgagtaga tttgtggaga cactggtggt
ggcagatgac aagatggccg cattccacgg tgcggggcta aagcgctacc tgctaacagt
gatggcagca gcagccaagg ccttcaagca cccaagcatc cgcaatcctg tcagcttggt
ggtgactcgg ctagtgatcc tggggtcagg cgaggagggg ccccaagtgg ggcccagtgc
tgcccagacc ctgcgcagct tctgtgcctg gcagcggggc ctcaacaccc ctgaggactc
ggaccctgac cactttgaca cagccattct gtttacccgt caggacctgt gtggagtctc
cacttgcgac acgctgggta tggctgatgt gggcaccgtc tgtgacccgg ctcggagctg
tgccattgtg gaggatgatg ggctccagtc agccttcact gctgctcatg aactgggtca
tgtcttcaac atgctccatg acaactccaa gccatgcatc agtttgaatg ggcctttgag
cacctctcgc catgtcatgg ccctgtgat ggctcatgtg atcctgagg agccctggtc
ccctgcagt  gcccgcttca tcactgactt cctggacaat ggctatgggc actgtctctt
agacaaacca gaggctccat tgcatctgcc tgtgactttc cctggcaagg actatgatgc
tgaccgccag tgccagctga ccttcgggcc cgactcacgc cattgtccac agctgccgcc
gccctgtgct gccctctggt gctctggcca cctcaatggc catgccatgt gccagaccaa
acactcgccc tgggccgatg cacaccctg cggcccgca caggcctgca tgggtggtcg
ctgcctccac atggaccagc tccaggactt caatattcca caggct
```

FIG. 24

TRUNCATED AGGRECANASE MOLECULES

RELATED APPLICATIONS

This application relies on the benefit of priority of U.S. provisional patent application Ser. No. 60/354,592 filed Feb. 5, 2002, the entire disclosure of which is incorporated by reference herein.

FIELD OF THE INVENTION

The present invention relates to the discovery of truncated aggrecanase molecules, processes for producing them, and methods employing these molecules to develop inhibitors to aggrecanase enzymes. The invention further relates to the development of inhibitors of, as well as antibodies to, aggrecanase enzymes. These inhibitors and antibodies may be useful for the treatment of various aggrecanase-associated conditions including osteoarthritis.

BACKGROUND OF THE INVENTION

Aggrecan is a major extracellular component of articular cartilage. It is a proteoglycan responsible for providing cartilage with its mechanical properties of compressibility and elasticity. The loss of aggrecan has been implicated in the degradation of articular cartilage in arthritic diseases such as osteoarthritis.

Osteoarthritis is a debilitating disease which affects at least 30 million Americans (MacLean et al., J Rheumatol 25:2213–2218 (1998)). Osteoarthritis can severely reduce quality of life due to degradation of articular cartilage and the resulting chronic pain. An early and important characteristic of the osteoarthritic process is loss of aggrecan from the extracellular matrix (Brandt and Mankin, "Pathogenesis of Osteoarthritis," *Textbook of Rheumatology*, W B Saunders Company, Philadelphia, Pa., pgs. 1355–1373 (1993)). The large, sugar-containing portion of aggrecan is thereby lost from the extra-cellular matrix, resulting in deficiencies in the biomechanical characteristics of the cartilage.

A proteolytic activity termed "aggrecanase" is believed to be responsible for the cleavage of aggrecan, thereby having a role in cartilage degradation associated with osteoarthritis and inflammatory joint disease. Research has been conducted to identify the enzymes responsible for the degradation of aggrecan in human osteoarthritic cartilage. Aggrecan contains two N-terminal globular domains, G1 and G2, separated by a proteolytically sensitive interglobular domain, followed by a glycosaminoglycan attachment region and a C-terminal globular domain, G3. At least two enzymatic cleavage sites have been identified within the interglobular domain of aggrecan. One enzymatic cleavage site within the interglobular domain of aggrecan ($Asn^{341}$-$Phe^{312}$) has been observed to be cleaved by several known metalloproteases. Flannery et al., J Biol Chem 267:1008–1014 (1992); Fosang et al., Biochemical J. 304: 347–351 (1994). Cleavage at a second aggrecan cleavage site within aggrecan ($Glu^{373}$-$Ala^{374}$) due to IL-1 induced cartilage aggrecan cleavage results in the generation of an aggrecan fragment found in human synovial fluid (Sandy et al., J Clin Invest 89:1512–1516 (1992); Lohmander et al., Arthritis Rheum 36: 1214–1222 (1993); Sandy et al., J Biol Chem 266: 8683–8685 (1991)). Aggrecan cleavage at ($Glu^{373}$-$Ala^{374}$) has been attributed to aggrecanase activity (Sandy et al., J Clin Invest 89:1512–1516 (1992). This $Glu^{373}$-$Ala^{374}$ cleavage site will be referred to as the aggrecanase cleavage site.

Recently, identification of two enzymes, aggrecanase-1 (ADAMTS-4) and aggrecanase-2 (ADAMTS-11) within the "a Disintegrin and Metalloproteinase with Thrombospondin motifs" (ADAMTS) family, have been identified which are synthesized by IL-1 stimulated cartilage and cleave aggrecan at the $Glu^{373}$-$Ala^{374}$ site (Tortorella et al., Science 284:1664–1666 (1999); Abbaszade et al., J Biol Chem 274: 23443–23450 (1999)). Aggrecanase-1 is reported to include at least six domains: signal; propeptide; catalytic; disintegrin; TSP type-1 motif and C-terminal. Aggrecanase-2 is also a multidomain protein. It is reported to have a signal sequence; a prodomain; a metalloproteinase domain; a disintegrin domain and a spacer domain between a TSP motif and a TSP sub motif in the C-terminal of the protein. It was generally believed that the TSP domains and the spacer domain are critical for substrate recognition. Specifically, Tortorella et al. reported that "this region may serve to bind aggrecanase-1 to the glycosaminoglycans of the aggrecan substrate." See Tortorella et al., Science 284:1664–1666 (1999).

It is contemplated that there are other, related enzymes in the ADAMTS family which are capable of cleaving aggrecan at the $Glu^{373}$-$Ala^{374}$ bond and could contribute to aggrecan cleavage in osteoarthritis. It is possible that these enzymes could be synthesized by osteoarthritic human articular cartilage. However, it has been difficult to develop inhibitors and treatment therapies to treat diseases that involve aggrecan cleavage because aggrecanases have been difficult to isolate and purify in large amounts due to poor stability of these molecules and generally low expression levels. Therefore, there is a need to identify novel forms of aggrecanases and further develop ways to isolate and purify aggrecanase proteins in large amounts in order to investigate their role in disease states and also to develop therapies and compositions to treat diseases involving aggrecan cleavage.

SUMMARY OF THE INVENTION

The present invention is directed to truncated aggrecanase proteins and variants and fragments thereof; nucleotide sequences which encode truncated aggrecanase enzymes of the invention and fragments and variants thereof; and processes for the production of truncated aggrecanases. Truncated aggrecanases of the invention are biologically active and have greater stability and higher expression levels than their full-length counterparts. More specifically, the invention features truncated aggrecanase-1 and aggrecanase-2 enzymes that are more stable and show higher levels of expression than full-length aggrecanase-1 and aggrecanase-2 enzymes, respectively; nucleic acid sequences encoding truncated aggrecanases-1 and 2 of the invention and fragments and variants thereof; and methods of producing truncated aggrecanases 1 and 2, or fragments and variants thereof.

In one embodiment, truncated aggrecanases of the invention comprise aggrecanases that have at least one TSP domain deleted. In another embodiment, truncated aggrecanases of the invention comprise aggrecanases that have at least two TSP domains deleted. Although, TSP domains in aggrecanases have been thought to be important for substrate recognition, and therefore, for the ability of aggrecanase to recognize and subsequently cleave aggrecan, truncated aggrecanase proteins of the invention are biologically active despite deletion of one or both TSP domains in the proteins.

Truncated aggrecanases of the invention have greater stability and are expressed at higher levels compared with the full-length aggrecanase proteins, thereby facilitating isolation, purification, and use of aggrecanases of the invention in the development of inhibitors and therapies for treatment of diseases. Accordingly, in one embodiment, the invention comprises methods for producing large amounts of purified truncated aggrecanases that may be used for development of inhibitors and treatment therapies.

The invention further includes compositions comprising truncated aggrecanases of the invention and use of such compositions for the development of inhibitors of aggrecanases for treatment of diseases including osteoarthritis. In addition, the invention includes methods for identifying and developing inhibitors of aggrecanase which block the enzyme's activity. The invention also includes antibodies to these enzymes, in one embodiment, for example, antibodies that block aggrecanase activity. These inhibitors and antibodies may be used in various assays and therapies for treatment of conditions characterized by the degradation of articular cartilage. In one embodiment, inhibitors are peptide molecules that bind aggrecanases.

This invention provides amino acid sequences of biologically active truncated aggrecanase molecules that have greater stability compared with the full-length aggrecanase protein.

In one aspect, the invention features biologically active truncated aggrecanase-2 molecules that have at least one TSP domain deleted, such as a protein with an amino acid sequence from amino acid #1 (Met) through amino acid #753 (Glu) of SEQ ID NO: 4; from amino acid #1 (Met) through amino acid #752 (Pro) of SEQ ID NO: 6; and from amino acid #1 (Met) through amino acid #628 (Phe) of SEQ ID NO: 8, and variants and fragments thereof, including substitution mutants, that exhibit aggrecanase activity.

The invention also features truncated aggrecanase-1 molecules that have at least one TSP domain deleted. An example includes an aggrecanase-1 protein with an amino acid sequence from amino acid #1 (Met) through amino acid #520 (Ala) of SEQ ID NO: 13, fragments, and variants thereof including substitution mutants that exhibit aggrecanase activity.

In another embodiment, the invention features biologically active truncated aggrecanase-2 proteins with at least two TSP domains deleted comprising, for example, a protein with an amino acid sequence from amino acid #1 through amino acid #527 (His) of SEQ ID NO: 10 (FIG. 10), variants, and fragments thereof including substitution mutants that exhibit aggrecanase activity.

Truncated aggrecanases with one or both TSP domains deleted are biologically active and are more stable than the full-length aggrecanase enzymes.

The invention also features nucleic acid molecules that encode truncated aggrecanases of the invention. For example, nucleic acid molecules encoding truncated aggrecanase-2 molecules of the invention include: nucleotide #1 through nucleotide #2259 of SEQ ID NO: 3 (FIG. 3), which encodes a polypeptide set forth in SEQ ID NO: 4; nucleotide #1 through nucleotide #2256 of SEQ ID NO: 5 (FIG. 5), which encodes a polypeptide set forth in SEQ ID NO: 6; nucleotide #1 through nucleotide #1884 of SEQ ID NO: 7 (FIG. 7), which encodes the polypeptide set forth in SEQ ID NO: 8; and nucleotide #1 through nucleotide #1701 of SEQ ID NO: 9 (FIG. 9), which encodes the polypeptide set forth in SEQ ID NO: 10. Nucleic acid molecules of the invention further include fragments and variants of SEQ ID NOs: 3, 5, 7, and 9 which encode truncated aggrecanase-2 molecules of the invention, nucleotide sequences that hybridize under moderate to stringent conditions with nucleotide sequences of SEQ ID NOs: 3, 5, 7, or 9 and fragments or variants thereof, naturally occurring allelic sequences, and equivalent degenerative codon sequences of aggrecanase-2 nucleic acid sequences disclosed herein.

Nucleic acid molecules encoding truncated aggrecanase-1 molecules of the invention include, for example, nucleotides which encode the polypeptides of SEQ ID NOs: 12 and 13; set forth in FIGS. 23 and 24 respectively, fragments and variants of nucleic acids that encode truncated aggrecanase-1 molecules of the invention, nucleotide sequences that hybridize under moderate to stringent conditions to nucleic acid sequences that encode truncated aggrecanase-1 molecules of the invention, for example, nucleic acid sequences of FIGS. 23 and 24, or fragments and variants thereof, naturally occurring allelic sequences and equivalent degenerative codon sequences of aggrecanase-1 encoding nucleic acid sequences. A nucleic acid sequence for full-length aggrecanase-1 molecule is found in Genbank under Accession No.: NM_005099 (FIG. 22). Therefore, one skilled in the art can use this sequence to generate a full-length aggrecanase-1 molecule set forth in SEQ ID NO: 11, or use part of the nucleotide sequence to generate a truncated protein, for example, the aggrecanase protein set forth in FIG. 12 or 13. For example nucleotide #407 through nucleotide #2132 of the published NM_005099 sequence (FIG. 23) (SEQ ID NO: 32) may be used for generating the truncated aggrecanase-1 protein of SEQ ID NO: 12. Similarly, nucleotide #1 through nucleotide #1967 of the published NM_005099 sequence (FIG. 24) (SEQ ID NO: 33) may be used for the generation of truncated aggrecanase molecule of FIG. 13.

In another aspect, the invention includes aggrecanase molecules that comprise mutations that increase stability and expression levels of truncated aggrecanase molecules compared with their full-length counterparts. Aggrecanases with mutations in their active sites are particularly useful for the synthesis of inhibitors of aggrecanases. Accordingly, in one embodiment, the invention features an aggrecanase-2 molecule with a mutation at amino acid 411 (E411-Q411 mutation) in the active site within the catalytic domain. The amino acid sequence of an aggrecanase-2 molecule with the E411-Q411 mutation is shown in FIG. 21 (SEQ ID NO: 30). Mutations that lead to increased stability of the aggrecanase proteins in comparison with their wild-type counterparts can be made in both truncated as well as full-length aggrecanase proteins. It is contemplated that mutations that alter stability of aggrecanase molecules can be made within the catalytic domain of an aggrecanase protein or outside the catalytic domain. Aggrecanase proteins carrying such mutations may be found in nature or may be generated artificially. One skilled in the art can test the effect of a mutation on the stability of an aggrecanase molecule by one of many assays provided. Mutations of the invention include, for example, amino acid substitutions or modifications. Amino acid mutations in aggrecanases of the invention can be generated by mutagenesis, chemical alteration, or by alteration of DNA sequence used to produce the polypeptide.

Aggrecanase-1 molecules can also be generated to include mutations in the catalytic domain in order to increase their stability. For example, FIG. 17 features flag-tagged truncated aggrecanase-1 proteins that include an E-to-Q amino acid mutation in the catalytic domain of truncated aggrecanase-1 molecules, the wild-type sequences of which are set forth in SEQ ID NO: 12 and 13, thereby leading to increased stability of aggrecanase-1 proteins compared to full-length wild-type aggrecanase-1 protein, the sequence of which is set forth in SEQ ID NO: 11. These aggrecanases are particularly useful for the development as well as identification of novel inhibitors of aggrecanases.

The invention further features truncated and/or mutant aggrecanase family members and aggrecanase-like proteins with deletions and/or substitution mutations, where a deletion or an amino acid substitution mutation occurs in a region of the protein comparable to that of aggrecanases of the invention.

The invention further includes variants and equivalent degenerative codon sequences of nucleic acid sequences described herein that encode biologically active truncated aggrecanase polypeptides. Additionally, the invention includes nucleic acid molecules that hybridize under moderate to stringent conditions to the nucleic acids of the invention, allelic variants and substitution and deletion mutants of nucleic acids molecules described herein. In one embodiment, truncated aggrecanases and/or aggrecanases carrying at least one amino acid substitution encoded by nucleic acid molecules of the invention are more stable than the corresponding full-length aggrecanase protein and can be expressed at higher levels than the full-length aggrecanase protein. In one embodiment, mutations are introduced in nucleic acid molecules encoding aggrecanases of the invention that lead to mutations; for example, amino acid substitutions, in the protein encoded by the nucleic acid carrying the mutation. One example of such a mutation is a nucleic acid sequence encoding an aggrecanase-2 protein with an E-to-Q mutation in the active site of molecule. In another embodiment, the invention includes aggrecanase-1 nucleic acid molecules that encode aggrecanase-1 proteins comprising an E-to-Q mutation in the catalytic domain, thereby leading to generation of molecules with greater stability, longer half-lives and increased levels of expression as compared to the full-length aggrecanases 1 and 2.

It is expected that other species have DNA sequences that are similar or identical to human aggrecanase enzymes described herein. Accordingly, the invention further includes methods for obtaining other nucleic acid molecules encoding truncated aggrecanases or aggrecanase-like molecules or aggrecanases with amino acid substitutions that alter their biological activity, from humans as well as non-human species. In one embodiment, a method for isolating a nucleic acid sequence encoding an aggrecanase of the invention involves utilizing a nucleic acid sequence disclosed herein or variants or fragments thereof; for example, SEQ ID NO: 1 or a fragment or a variant thereof; SEQ ID NO: 3 or a fragment or a variant thereof; SEQ ID NO: 5 or a fragment or a variant thereof; SEQ ID NO: 7 or a fragment or a variant thereof; SEQ ID NO: 9 or a fragment or a variant thereof; SEQ ID NO: 31 or a fragment or a variant thereof; SEQ ID NO: 32 or a fragment or variant thereof; or SEQ ID NO: 33 or a fragment or a variant thereof, to design probes for screening libraries for the corresponding gene from other species or coding regions of genes that encode proteins/peptides with aggrecanase activity. Therefore, the invention includes DNA sequences from other species, which are homologous to human aggrecanase sequences, or fragments or variants thereof, and can be obtained using at least one of the DNA sequences provided herein. In addition, the present invention includes DNA sequences that encode fragments or variants of aggrecanases of the invention. The present invention may also include functional fragments of the aggrecanase protein, and DNA sequences encoding such functional fragments, as well as functional fragments of other related proteins. The ability of such a fragment to function is determinable by an assay of the protein in one of many biological assays described for the assay of the aggrecanase protein.

In another aspect, the invention provides methods for producing isolated truncated aggrecanases of the invention. In one embodiment, a human aggrecanase protein of the invention or a variant or fragment thereof may be produced, for example, by culturing a cell transformed with a DNA sequence: from nucleotide #1 through nucleotide #2259, set forth in SEQ ID NO: 3; or from nucleotide #1 through nucleotide #2256, set forth in FIG. 5; or from nucleotide #1 through nucleotide #1884, set forth in FIG. 7; or from nucleotide #1 through nucleotide #1701, set forth in FIG. 9, and recovering and purifying from the culture medium an aggrecanase-2 protein characterized by the amino acid sequence set forth in: FIG. 4 from amino acid #1 (Met) through amino acid #753 (Glu); FIG. 6 from amino acid #1 (Met) through amino acid #752 (Pro); FIG. 8 from amino acid #1 (Met) through amino acid #628 (Phe); or FIG. 10 from amino acid #1 (Met) through amino acid #567 (His). Similarly, nucleic acid sequences expressing truncated aggrecanase-1 molecules; for example, nucleic acid sequences set forth in FIGS. 23 and 24 can be used for the production of truncated aggrecanase-1 proteins set forth in FIGS. 12 and 13, where the aggrecanase-1 proteins are substantially free from other proteinaceous materials with which they are co-produced.

In another embodiment, truncated aggrecanase proteins of the invention may be produced by culturing a cell transformed with a full-length DNA sequence for aggrecanase, and recovering truncated aggrecanase proteins from the culture medium. Accordingly, in one embodiment, a truncated aggrecanase-2 protein including amino acid #1 (Met) to amino acid #753 (Glu), set forth in SEQ ID No: 4, is recovered from the culture medium of a cell transformed with a full-length nucleic acid molecule for aggrecanase-2; for example, nucleic acid molecule set forth in SEQ ID NO: 1. In another embodiment, a truncated aggrecanase-2 molecule including amino acid #1 (Met) to amino acid #752 (Pro), is recovered from culture medium of cells transformed with a nucleic acid molecule for full-length aggrecanase-2. Truncated aggrecanase protein of SEQ ID NO: 4 results from cleavage of the full-length aggrecanase protein, set forth in SEQ ID NO: 2, at $E^{753}$-$G^{754}$, yielding a 55 kDa protein. The nucleotide and amino acid sequences of the full-length aggrecanase-2 molecule are set forth in SEQ ID NO: 1 and SEQ ID NO: 2 respectively (Accession Nos: NM_007038 and NP_008969) (FIGS. 1A–1C and 2).

Truncated aggrecanases of the invention that are purified from a culture medium are substantially free from other proteinaceous materials. A recovered purified aggrecanase protein having at least one TSP domain deleted generally exhibits proteolytic aggrecanase activity by cleaving aggrecan, as disclosed. Therefore, truncated proteins of the invention may be further characterized by the ability to demonstrate aggrecan proteolytic activity in an assay which determines the presence of an aggrecan-degrading molecule. These assays or the development thereof is within the knowledge of one skilled in the art. Such assays may involve contacting an aggrecan substrate with a truncated aggrecanase molecule and monitoring the production of aggrecan fragments (see, for example, Hughes et al., Biochem J 305: 799–804 (1995); Mercuri et al., J. Bio Chem. 274:32387–32395 (1999)). For production in mammalian cells, a DNA sequence used for expression of a truncated aggrecanase of the invention further comprises a DNA sequence encoding a suitable propeptide 5' to and linked in frame to the nucleotide sequence encoding the aggrecanase enzyme.

The invention also provides antibodies that bind to isolated aggrecanase proteins of the invention. In one embodiment, such an antibody reduces, inhibits or antagonizes aggrecanase activity. The invention further provides methods for developing and identifying inhibitors of aggrecanase activity comprising the use of a truncated aggrecanase protein with amino acid sequence chosen from, for example, SEQ ID NO: 4, SEQ ID NO: 6, SEQ ID NO: 8, SEQ ID NO: 10, SEQ ID NO: 12, or SEQ ID NO: 13 or a fragment or a variant thereof. In one embodiment, inhibitors of aggrecanase activity prevent cleavage of aggrecan.

Additionally, the invention provides pharmaceutical compositions for inhibiting the proteolytic activity of aggrecanases, wherein the compositions comprise at least one antibody according to the invention and at least one pharmaceutical carrier. The invention also provides methods for inhibiting aggrecanase activity in a mammal comprising administering to the mammal an effective amount of a pharmaceutical composition according to the invention to inhibit aggrecanase activity.

In another embodiment, the invention includes methods for identifying or developing inhibitors of aggrecanases and the inhibitors produced thereby. In one embodiment, inhibitors of the invention prevent binding of an aggrecanase to an aggrecan molecule. In another embodiment, inhibitors of the invention prevent cleavage of aggrecan by aggrecanase.

The method may entail the identification of inhibitors based on an assay comprising combining at least one aggrecanase protein of this invention with at least one test sample; and determining if the test sample inhibits activity of the aggrecanase protein. The test sample may comprise known or unknown samples, and these samples may be peptides, proteins, chemical compounds (often referred to as small molecules), or antibodies. They may be selected for testing individually, or in batches, such as from a library. The art provides aggrecanase activity assays that could be easily utilized in such a method. Assays for inhibitors may involve contacting a mixture of aggrecan and the inhibitor with an aggrecanase molecule followed by measurement of the aggrecanase inhibition; for instance, by detection and measurement of aggrecan fragments produced by cleavage at an aggrecanase-susceptible site.

The method may also entail the determination of binding sites based on at least one of the amino acid sequences of aggrecanase and the three-dimensional structure of aggrecanase, and optionally aggrecan. Based on this information, one could develop or identify a candidate molecule that may inhibit aggrecanase activity based on a structural analysis, such as predicted structural interaction with the binding site. In one embodiment, such a molecule may comprise a peptide, protein, chemical compound, or antibody. Candidate molecules may be later assayed for actual inhibitory activity of the aggrecanase enzyme, as discussed.

Another aspect of the invention therefore provides pharmaceutical compositions containing a therapeutically effective amount of aggrecanase inhibitors in a pharmaceutically acceptable vehicle.

Aggrecanase-mediated degradation of aggrecan in cartilage has been implicated in osteoarthritis and other inflammatory diseases. Therefore, these compositions of the invention may be used in the treatment of diseases characterized by the degradation of aggrecan and/or an up regulation of aggrecanase. The compositions may be used in the treatment of these conditions or in the prevention thereof.

The invention further includes methods for treating patients suffering from conditions characterized by a degradation of aggrecan or preventing such conditions. These methods, according to the invention, entail administering to a patient needing such treatment an effective amount of a composition comprising an aggrecanase inhibitor which inhibits the proteolytic activity of aggrecanase enzymes.

The DNA sequences of the present invention are useful, for example, as probes for the detection of mRNA encoding aggrecanase in a given cell population. Thus, the present invention includes methods of detecting or diagnosing genetic disorders involving aggrecanases, or disorders involving cellular, organ, or tissue disorders in which aggrecanase is irregularly transcribed or expressed. The DNA sequences may also be useful for preparing vectors for gene therapy applications as described below.

A further aspect of the invention includes vectors comprising a DNA sequence as described above in operative association with an expression control sequence therefor. These vectors may be employed in a novel process for producing an aggrecanase protein of the invention in which a cell line transformed with a DNA sequence encoding an aggrecanase protein in operative association with an expression control sequence therefor, is cultured in a suitable culture medium and an aggrecanase protein is recovered and purified therefrom. This process may employ a number of known cells, both prokaryotic and eukaryotic in origin, as host cells for expression of the polypeptide. The vectors may be used in gene therapy applications. In such use, the vectors may be transfected into the cells of a patient ex vivo, and the cells may be reintroduced into a patient. Alternatively, the vectors may be introduced into a patient in vivo through targeted transfection.

Additional aspects of the disclosure will be set forth in part in the description, and in part be obvious from the description, or may be learned from practicing the invention. The invention is set forth and particularly pointed out in the claims, and the disclosure should not be construed as limiting the scope of the claims. The following detailed description includes exemplary representations of various embodiments of the invention, which are not restrictive of the invention as claimed. The accompanying figures constitute a part of this specification and, together with the description, serve to illustrate embodiments and not limit the invention.

DESCRIPTION OF THE DRAWINGS

FIGS. 1A–1C show the nucleotide sequence of a full-length aggrecanase-2/ADAMTS-5 molecule (SEQ ID NO: 1).

FIG. 2 shows the amino acid sequence of a full length aggrecanase-2/ADAMTS-5 molecule (SEQ ID NO: 2) encoded by nucleotide #1 through nucleotide #2915 of SEQ ID NO: 1.

FIG. 3 shows the nucleotide sequence of a truncated aggrecanase-2 protein of the invention from nucleotide #1 through nucleotide #2259 (SEQ ID NO: 3).

FIG. 4 shows the amino acid sequence of a truncated aggrecanase-2 protein of the invention from amino acid #1 through amino acid #753 (SEQ ID NO: 4), encoded by nucleotide sequence set forth in SEQ ID NO: 3.

FIG. 5 shows the nucleotide sequence of a truncated aggrecanase-2/ADAMTS-5 of the invention from nucleotide #1 through nucleotide #2256 (SEQ ID NO: 5).

FIG. 6 shows the amino acid sequence of a truncated aggrecanase-2 protein of the invention from amino acid #1 through amino acid #752 (SEQ ID NO: 6), encoded by nucleotide sequence set forth in SEQ ID NO: 5.

FIG. 7 shows the nucleotide sequence of a truncated aggrecanase-2 molecule of the invention from nucleotide #1 through nucleotide #1884 (SEQ ID NO: 7).

FIG. 8 shows the amino acid sequence of a truncated aggrecanase-2 protein of the invention from amino acid #1 through amino acid #628 (SEQ ID NO: 8), encoded by the nucleotide sequence set forth in SEQ ID NO: 7.

FIG. 9 shows the nucleotide sequence of a truncated aggrecanase-2 molecule of the invention from nucleotide #1 through nucleotide #1701 (SEQ ID NO: 9).

FIG. 10 shows the amino acid sequence of a truncated aggrecanase-2 protein of the invention from amino acid #1 through amino acid #567 (SEQ ID NO: 10), encoded by the nucleotide sequence set forth in SEQ ID NO: 9.

FIG. 11 shows the amino acid sequence of a full-length aggrecanase-1 molecule (SEQ ID NO: 11).

FIG. 12 shows the amino acid sequence of a truncated aggrecanase-1 molecule including amino acid #1 through amino acid #575 (Pro) (SEQ ID NO: 12).

FIG. 13 shows the amino acid sequence of a truncated aggrecanase-1 molecule including amino acid #1 through amino acid #520 (Ala) (SEQ ID NO: 13).

FIG. 14 shows the nucleotide sequence of a recombinant truncated aggrecanase-2 protein comprising a peptide linker and a streptavidin tag (SEQ ID NO: 14).

FIG. 15 shows the amino acid sequence of a recombinant truncated aggrecanase-2 protein (SEQ ID NO: 15), encoded by nucleotide sequence set forth in SEQ ID NO: 14.

Figure 16:
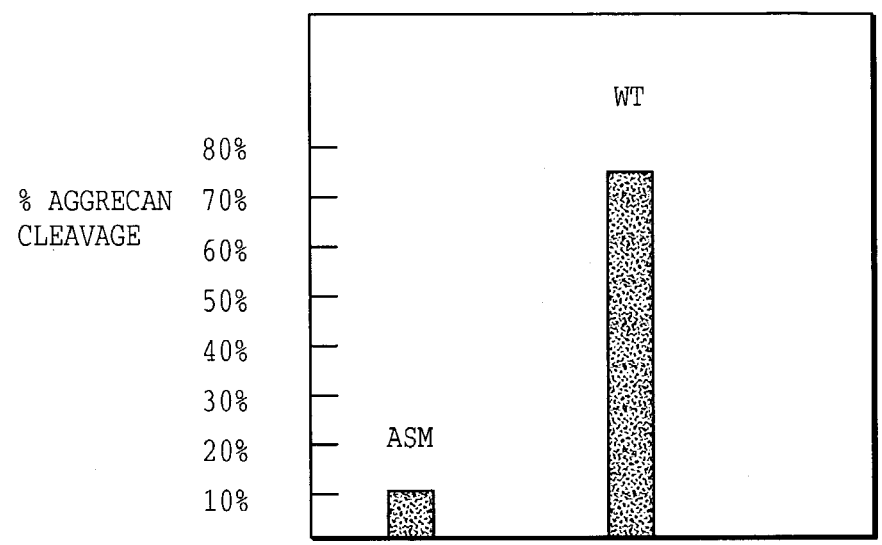

FIG. 16 shows aggrecanase activity of conditioned medium from CHO cells expressing wild-type (ADAMTS-5 WT) or active-site mutant (ADAMTS-5 ASM) as detected by the aggrecanase ELISA assay.

Figure 17:
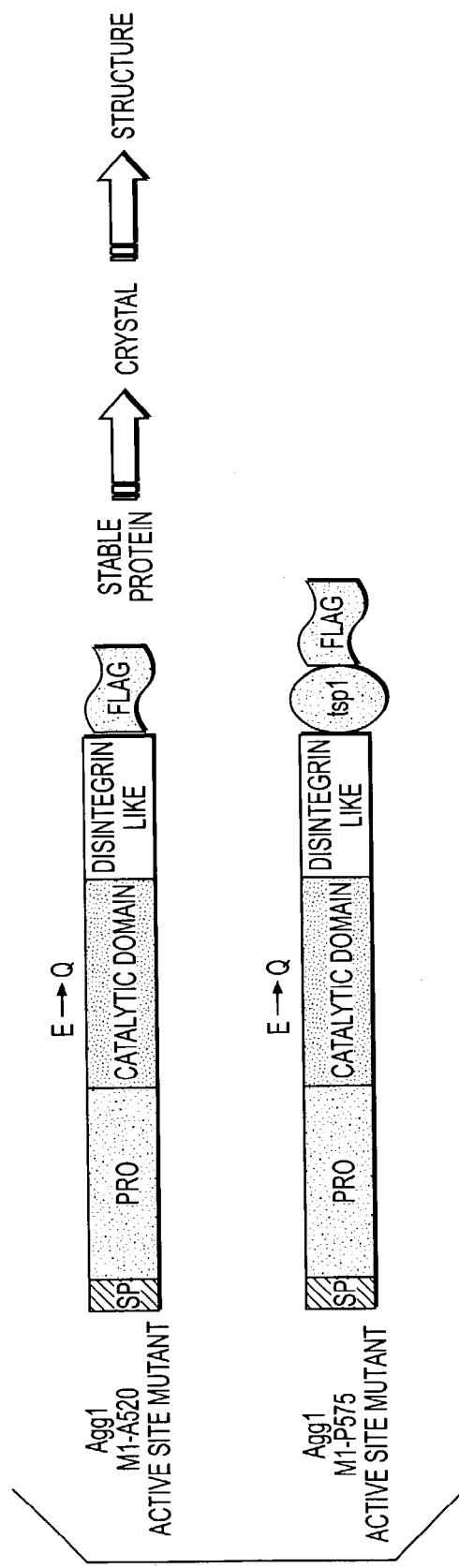

FIG. 17 shows a schematic representation of flag-tagged truncated aggrecanase-1 molecules with an E-to-Q mutation in the catalytic domain.

Figure 18:
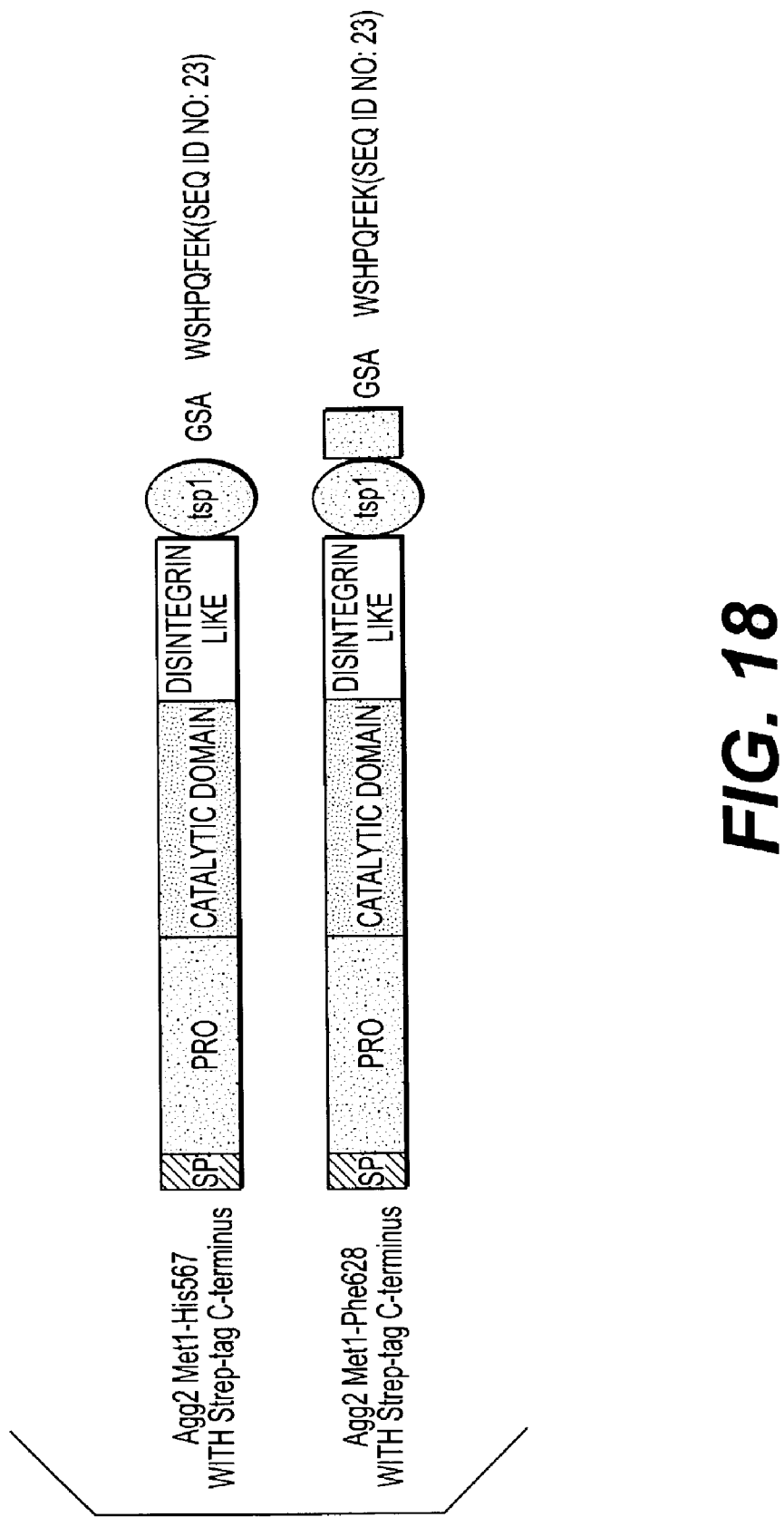

FIG. 18 shows a schematic representation of streptavidin tagged truncated aggrecanase-2 molecules.

Figure 19:
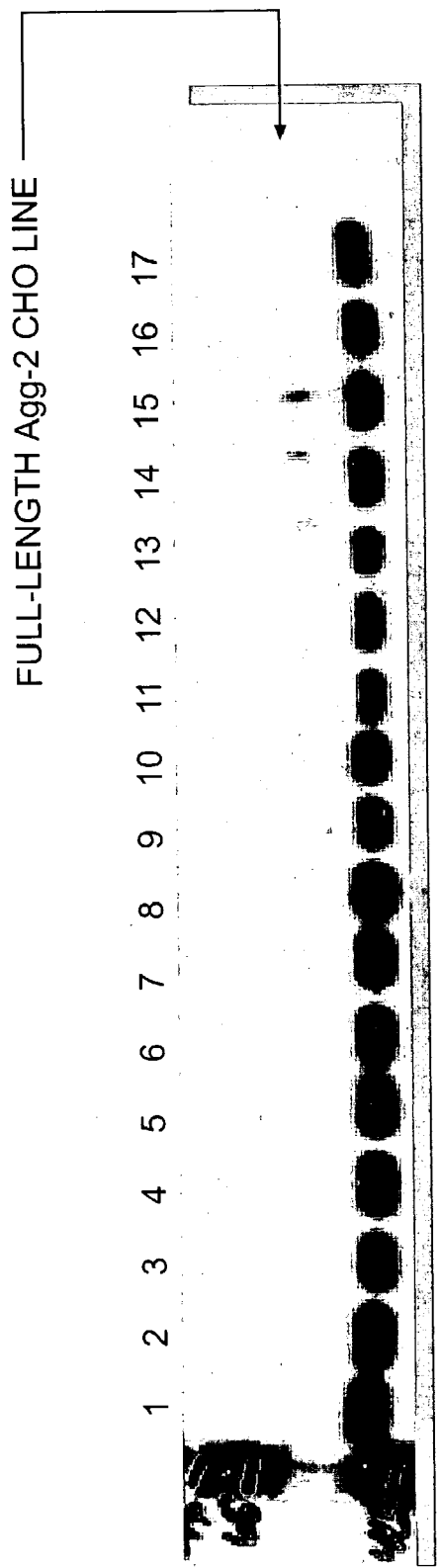

FIG. 19 shows a western blot with expression of truncated aggrecanase-2 proteins in comparison with a full-length aggrecanase-2 protein.

Figure 20:
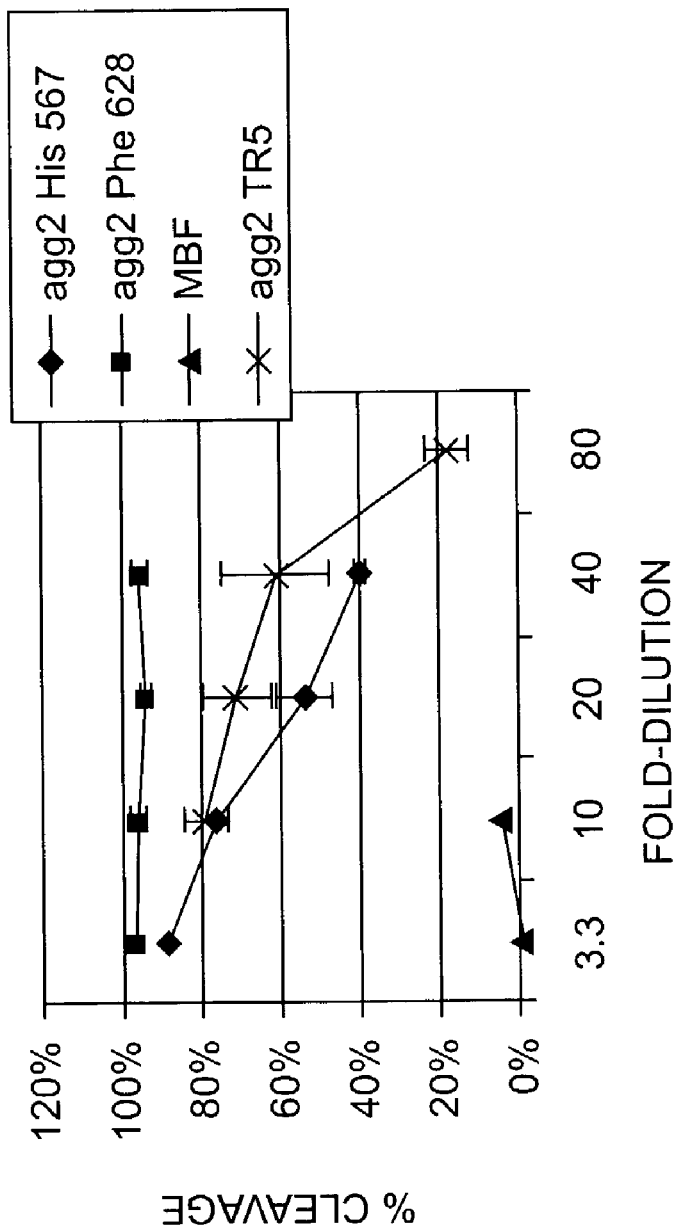

FIG. 20 shows percent aggrecan cleavage by truncated aggrecanase-2 molecules of the invention in a 3B3 ELISA assay.

FIG. 21 shows the amino acid sequence for a full-length ADAMTS-5 protein with an E-to-Q mutation at amino acid position 411 (SEQ IS NO: 30).

FIGS. 22A and 22B show a nucleic acid sequence encoding a full-length aggrecanase-1 protein (SEQ ID NO: 31).

FIG. 23 shows a nucleic acid sequence encoding a truncated aggrecanase-1 molecule; for example, the protein set forth in FIG. 12 (SEQ ID NO: 32).

FIG. 24 shows a nucleic acid sequence encoding a truncated aggrecanase-1 molecule; for example, the protein set forth in FIG. 13 (SEQ ID NO: 33).

DETAILED DESCRIPTION OF THE INVENTION

I. Definitions

In order that the present invention may be more readily understood, certain terms are first defined. Additional definitions are set forth throughout the detailed description.

The term "aggrecanase" refers to a family of polypeptides that are capable of cleaving the aggrecan protein. Generally, these are proteins that cleave aggrecan at the $Glu^{373}$-$Ala^{374}$ aggrecanase cleavage site. Aggrecanases of the present invention encompass but are not limited to the sequences of SEQ ID NO: 11 (aggrecanase-1) and SEQ ID NO: 2 (aggrecanase-2). The term "aggrecanase" includes naturally occurring variants SEQ ID NOs: 11 and 2, as well as fragments of the sequences encoded by SEQ ID NOs: 11 and 2 that are active in at least one of the assays provided. For example, included in this definition are amino acid sequences substantially similar or substantially identical to the amino acid of SEQ ID NOs: 11 or 2 or fragments thereof; or an amino acid sequence at least about 50%, about 55%, about 60%, about 65%, about 70%, about 75%, about 80%, about 85%, about 90%, about 92%, about 93%, about 94%, about 95%, about 96%, about 97%, about 98%, or about 99% identical to the amino acid sequence of SEQ ID NO: 11 or 2, or a fragment thereof.

The term aggrecanase further includes the proteins encoded by the nucleic acid sequence of SEQ ID NO: 31 and 1 (aggrecanase-1 and 2 respectively) disclosed, fragments and variants thereof. In one embodiment, the nucleic acids of the present invention will possess a sequence which is either derived from, or is a variant of a natural aggrecanase encoding gene, or a fragment thereof.

The term "antibody" refers to an immunoglobulin, or a fragment thereof, and encompasses any polypeptide comprising an antigen-binding site. The term includes but is not limited to polyclonal, monoclonal, monospecific, polyspecific, non-specific, humanized, human, single-chain, chimeric, synthetic, recombinant, hybrid, mutated, grafted, and in vitro generated antibodies. It also includes, unless otherwise stated, antibody fragments such as Fab, F(ab')$_2$, Fv, scFv, Fd, dAb, and other antibody fragments which retain the antigen binding function.

The term "biological activity" refers to at least one cellular process interrupted or initiated by an aggrecanase enzyme binding to aggrecan. Generally, biological activity refers to proteolytic cleavage of aggrecan by aggrecanase. Aggrecanase activities include, but are not limited to, binding of aggrecanase to aggrecan and cleavage of aggrecan by aggrecanase. Activity can also include a biological response resulting from the binding to or cleavage of aggrecan by aggrecanases of the invention.

The term "deletion" as used herein is the removal of at least one amino acid from the full-length amino acid sequence of an aggrecanase. The term deletion also refers to removal of nucleotides from a nucleic acid sequence encoding an aggrecanase, thereby resulting in a nucleic acid that encodes a truncated protein.

A deletion in a nucleic acid molecule encoding an aggrecanase or an aggrecanase protein can be made anywhere in the nucleic acid molecule or the protein as desirable. For example, a deletion may occur anywhere within the protein; for example, N-terminus, C-terminus or any other part of an aggrecanase protein, and can include removal of at least one amino acid; for example, from about 1 to about 5 amino acids, from about 5 to about 10 amino acids, from about 10 to about 20 amino acids, from about 20 to about 30 amino acids, from about 30 to about 50 amino acids, from about 50 to about 100 amino acids, from about 100 to about 150 amino acids, from about 150 to about 200 amino acids, from about 200 to about 250 amino acids, from about 250 to about 300 amino acids, from about 300 to about 350 amino acids, from about 350 to about 400 amino acids, from about 400 to about 450 amino acids, from about 450 to about 500 amino acids, or greater than 500 amino acids.

Deletions can also be made in nucleic acid molecules that encode aggrecanases of the invention; for example, deletions can be made in the region of a nucleic acid that encodes for a TSP domain of an aggrecanase. Such deletions typically encompass the 3' region of a nucleic acid molecule encoding an aggrecanase of the invention. However, it is contemplated that deletions can be made anywhere in a nucleic acid expressing an aggrecanase molecule. One skilled in the art can test truncated aggrecanases of the invention for activity in one of many assays disclosed.

An amino acid deletion according to the invention comprises the removal of at least one amino acid from the N-terminus of an aggrecanase protein. In another embodiment, a deletion comprises removal of at least one amino acid from the C-terminus of an aggrecanase protein. In yet another embodiment, a deletion comprises removal of amino acids from a region lying between N-terminal end and C-terminal end of an aggrecanase molecule. In one embodiment, such a deletion involves removal of an entire domain of an aggrecanase of the invention. For example, aggrecanases of the invention comprising a deletion include aggrecanase-1 molecules that have one TSP domain deleted or aggrecanase-1 molecules that have two TSP domains deleted, or aggrecanase-2 molecules that have one TSP domain deleted, or aggrecanase-2 molecules that have two TSP domains deleted. Aggrecanases according to the invention may comprise deletion of all TSP domains within an aggrecanase protein. It is contemplated that other domains within aggrecanase molecules may also be deleted to generate biologically active truncated aggrecanases that are more stable than the full-length counterpart.

The term "fragment" as used herein, refers to a portion of an aggrecanase protein of the invention, for example, a portion of amino acid sequences set forth in SEQ ID NO: 2, 4, 6, 8, 10, 11, 12, and 13. In one embodiment, a fragment of a protein refers to an amino acid sequence that has aggrecanase activity in one of many assays provided. The term "fragment" also includes nucleotide sequences that are long enough to encode peptides that exhibit aggrecanase activity. However, fragments of a nucleotide sequence may or may not encode protein fragments that retain aggrecanase biological activity. Protein and nucleic acid fragments of the invention include portions of other nucleic acid molecules or proteins that are substantially identical to at least one portion of the nucleotide sequences set forth in SEQ ID NOs: 1, 3, 5, 7, 9, 31, 32, or 33, or at least one portion of amino acid sequences set forth in SEQ ID NOs: 2, 4, 6, 8, 10, 11, 12, or 13, respectively. Fragments of nucleic acid sequences may range, for example, from at least about 20 nucleotides, from at least about 50 nucleotides, from at least about 100 nucleotides, from at least about 150 nucleotides, from at least about 200 nucleotides, from at least about 250 nucleotides, from at least about 300 nucleotides, from at least about 400 nucleotides, from at least about 500 nucleotides, from at least about 600 nucleotides, from at least about 700 nucleotides, from at least about 800 nucleotides, up to the entire length of the nucleic acid sequence set forth in SEQ ID NO: 1. In one embodiment, nucleic acid fragments encode peptides that have aggrecanase activity. Protein fragments may range, for example, from at least about 5 amino acids, from at least about 10 amino acids, from at least about 20 amino acids, from about 30 amino acids, from about 40 amino acids, from about 50 amino acids, from at least about 100 amino acids, from at least about 150 amino acids, from at least about 200 amino acids, from at least about 250 amino acids, from at least about 300 amino acids, from at least about 350 amino acids, from at least about 400 amino acids, up to the entire length of the amino acid sequence set forth in SEQ ID NO: 2. Fragments of nucleic acids of the invention can arise from 3' portions, 5' portions or any other part of a nucleic acid sequence. Similarly, protein fragments can arise from N-terminus portion, C-terminus portion or any other part of a protein. In one embodiment, fragments of proteins retain aggrecanase activity. In another embodiment, protein fragments of the invention arise from a portion of a protein that has aggrecanase activity.

The term "effective amount" refers to a dosage or an amount of a composition of at least one aggrecanase inhibitor or antibody of the invention that is sufficient to treat a patient.

The term "inhibit" or "inhibition" of aggrecanase or aggrecanase activity refers to a reduction, inhibition of otherwise diminution of at least one activity of aggrecanase due to binding of an inhibitor to the aggrecanase or aggrecan. The reduction, inhibition, or diminution of binding can be measured by one of many assays provided. Inhibition of aggrecanase activity does not necessarily indicate a complete negation of aggrecanase activity. A reduction in activity can be, for example, at least about 10%, 20%, 30%, 40%, 50%, 60%, 70%, 80%, 90%, or more. In one embodiment, inhibition is measured by a reduction in the detection of cleavage products of aggrecan. Inhibitors of the present invention include, but are not limited to, antibodies, proteins, peptides, and chemical compounds (often referred to as small molecules).

The term "isolated" describes a nucleic acid molecule or polypeptide molecule that is substantially free of its natural environment. For instance, an isolated protein is substantially free of cellular material or other contaminating proteins from the cell or tissue source from which it is derived. The term "isolated" also refers to an aggrecanase protein according to the invention which is free from association with other proteases and retains aggrecanase proteolytic activity. In addition, the term "isolated" refers to nucleic acid molecules that encode aggrecanases of the invention and are free from other cellular material and contaminants.

The term "neoepitope antibody" refers to an antibody that specifically recognizes a new N- or C-terminal amino acid sequence generated by proteolytic cleavage but which does not bind to such an epitope on the intact (uncleaved) substrate.

The term "operative association" with an expression control sequence generally refers to the presence of a specific nucleotide sequence or sequences that control or affect transcription rate or efficiency of a nucleotide molecule linked to the sequence. For example, a promoter sequence that is located proximally to the 5' end of an aggrecanase coding nucleotide sequence may be in operative association with the aggrecanase encoding nucleotide sequence. Expression control sequences include, but are not limited to, for example, promoters, enhancers, and other expression control sequences, or any combination of such elements, either 5' or 3' to an aggrecanase encoding nucleotide sequence in order to control its expression. Not all of these elements are required, however. A skilled artisan can select the appropriate expression control sequences, for example, depending on desired expression levels for the aggrecanases of the invention.

The term "specific binding" of an antibody means that the antibody binds to at least one aggrecanase molecule of the present invention and the antibody will not show any significant binding to molecules other than at least one novel aggrecanase molecule. The term is also applicable where, e.g., an antigen binding domain of an antibody is specific for a particular epitope, which is represented on a number of antigens, and the specific binding member (the antibody) carrying the antigen binding domain will be able to bind to the various antigens carrying the epitope. Therefore, it is contemplated that an antibody of the invention will bind to an epitope on multiple novel aggrecanase proteins. Typically, the binding is considered specific when the affinity constant $K_a$ is higher than $10^8$ $M^{-1}$. An antibody is said to "specifically bind" to an antigen if, under appropriately selected conditions, such binding is not substantially inhibited, while at the same time non-specific binding is inhibited. The conditions are usually defined in terms of concentration of antibodies, ionic strength of the solution, temperature, time allowed for binding, concentration of additional molecules associated with the binding reaction (e.g., serum albumin, milk casein), etc. Such conditions are well known in the art, and a skilled artisan using routine techniques can select appropriate conditions.

The term "stability" as used herein, generally refers to a decrease in the rate of degradation of a protein, thereby increasing its half-life, solubility, and/or expression levels. Several factors affect protein stability in vitro and in vivo, for example, pH, salt concentration, temperature, protein degradation, for example by proteases, metal ions, autocatalysis of proteins, hydrophobicity etc. In one embodiment, the invention includes truncated aggrecanases that are more stable than their full-length counterparts. In another embodiment, the invention includes aggrecanase active-site mutants that are more stable than their wild-type counterparts. Conditions that make a protein more stable generally include conditions that keep the protein in a folded conformation for longer than normal, thereby preserving its biological activity for a longer period of time. An increase in stability of a protein generally increases its half-life and expression levels, thereby making it possible to purify the protein in large amounts for therapeutic purposes and for development of inhibitors.

The term "highly stringent" or "high stringency" describes conditions for hybridization and washing used for determining nucleic acid-nucleic acid interactions. Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. The stringency conditions are dependent on the length of the nucleic acid and the base composition of the nucleic acid and can be determined by techniques well known in the art. Generally, stringency can be altered or controlled by, for example, manipulating temperature and salt concentration during hybridization and washing. For example, a combination of high temperature and low salt concentration increases stringency. Such conditions are known to those skilled in the art and can be found in, for example, *Current Protocols in Molecular Biology*, John Wiley & Sons, N.Y., 6.3.1–6.3.6, (1989). Both aqueous and nonaqueous conditions as described in the art can be used. One example of highly stringent hybridization conditions is hybridization in 6× sodium chloride/sodium citrate (SSC) at about 45° C., followed by at least one wash in 0.2×SSC, 0.1% SDS at 50° C. A second example of highly stringent hybridization conditions is hybridization in 6×SSC at about 45° C., followed by at least one wash in 0.2×SSC, 0.1% SDS at 55° C. Another example of highly stringent hybridization conditions is hybridization in 6×SSC at about 45° C., followed by at least one wash in 0.2×SSC, 0.1% SDS at 60° C. A further example of highly stringent hybridization conditions is hybridization in 6×SSC at about 45° C., followed by at least one wash in 0.2×SSC, 0.1% SDS at 65° C. Highly stringent conditions include hybridization in 0.5M sodium phosphate, 7% SDS at 65° C., followed by at least one wash at 0.2×SSC, 1% SDS at 65° C.

The phrase "moderately stringent" or "moderate stringency" hybridization refers to conditions that permit a nucleic acid to bind a complementary nucleic acid that has at least about 60%, at least about 75%, or at least about 85%, identity to the nucleic acid, with greater than about 90% identity to the nucleic acid especially preferred. Moderately stringent conditions comprise but are not limited to, for example, hybridization in 50% formamide, 5× Denhart's solution, 5×SSPE, 0.2% SDS at 42° C., followed by washing in 0.2×SSPE, 0.2% SDS, at 65° C. (see, e.g., Sambrook et al., *Molecular Cloning: A Laboratory Manual*, Cold Spring Harbor Laboratory Press, 1989).

The phrase "substantially identical" or "substantially similar" means that the relevant amino acid or nucleotide sequence will be identical to or have insubstantial differences (through conserved amino acid substitutions) in comparison to the sequences which are disclosed. Nucleotide and polypeptides of the invention include, for example, those that are at least about 50%, at least about 55%, at least about 60%, at least about 65%, at least about 70%, at least about 75%, at least about 80%, at least about 85%, at least about 90%, at least about 92%, at least about 93%, at least about 94%, at least about 95%, at least about 96%, at least about 97%, at least about 98%, or at least about 99% identical in sequence to nucleic acid molecules and polypeptides disclosed.

For polypeptides, at least 20, 30, 50, 100, or more amino acids will be compared between the original polypeptide and the variant polypeptide that is substantially identical to the original. For nucleic acids, at least 50, 100, 150, 300, or more nucleotides will be compared between the original nucleic acid and the variant nucleic acid that is substantially identical to the original. Thus, a variant could be substantially identical in a region or regions, but divergent in others, while still meeting the definition of "substantially identical." Percent identity between two sequences is determined by standard alignment algorithms such as, for example, Basic Local Alignment Tool (BLAST) described in Altschul et al., J. Mol. Biol., 215:403–410 (1990), the algorithm of Needleman and Wunsch, J. Mol. Biol., 48:444–453 (1970), or the algorithm of Meyers and Miller, Comput. Appl. Biosci., 4:11–17 (1988).

The term "treating" or "treatment" refers to both therapeutic treatment and prophylactic or preventative measures. Those in need of treatment may include individuals already having a particular medical disorder as well as those who may ultimately acquire the disorder (i.e., those needing preventative measures). Treatment may regulate aggrecanase activity or the level of aggrecanase to prevent or ameliorate clinical symptoms of at least one disease. The inhibitors and/or antibodies may function by, for example, preventing the interaction or binding of aggrecanase to aggrecan, or by reducing or inhibiting aggrecanase activity.

The term "truncated" as used herein, refers to nucleotides encoding aggrecanases of the invention that are missing at least one nucleotide, or aggrecanases of the invention that are missing at least one amino acid, which are found in a full-length aggrecanase nucleic acid molecule or amino acid sequence, respectively. Truncated proteins of the invention are generally shorter in length compared with their full-length counterparts, usually due to a deletion of at least one nucleotide in a nucleic acid sequence encoding a truncated protein or in at least one amino acid of the corresponding full-length protein.

In one embodiment, for example, truncated aggrecanases of the invention include truncated aggrecanase-1 proteins comprising an amino acid sequence set forth in SEQ ID NO: 12 comprising deletion of amino acid #576 through the C-terminal end of the full-length aggrecanase-1 protein, set forth in SEQ ID NO: 11; and SEQ ID NO: 13 comprising deletion of amino acid #521 through the C-terminal end of the full-length aggrecanase-1 protein, set forth in SEQ. ID NO: 11. In another embodiment, truncated aggrecanases of the invention comprise aggrecanase-2 truncated proteins; for example, as set forth in SEQ ID NO: 4 comprising deletion of amino acid #754 through the C-terminal end of the full-length aggrecanase-2 protein, set forth in SEQ ID NO: 2; SEQ ID NO: 6 comprising deletion of amino acid #753 through the C-terminal end of the full-length aggrecanase-2 protein, set forth in SEQ ID NO: 2; SEQ ID NO: 8 comprising deletion of amino acid #629 through the C-terminal end of the full-length aggrecanase-2 protein, set forth in SEQ ID NO: 2; and SEQ ID NO: 10 comprising deletion of amino acid #568 through the C-terminal end of the full-length aggrecanase-2 protein, set forth in SEQ ID NO: 2. Such a deletion can be made either in a nucleic acid that encodes an aggrecanase or be made in the protein itself subsequent to the formation of the protein. Accordingly, the term "truncated" as used herein refers to nucleic acids that encode aggrecanases that are truncated as well as truncated aggrecanases themselves. Nucleic acids encoding for truncated proteins of the invention are depicted in SEQ ID NOs: 3, 5, 7, 9, 11, 32, and 33. Truncated proteins of the invention can be expressed as fusion proteins.

Truncated aggrecanases of the invention have greater stability than the corresponding full-length aggrecanase molecule. Truncated aggrecanases of the invention can also be expressed at higher levels both in vivo and in vitro than the corresponding full-length aggrecanase proteins. Truncated aggrecanases of the invention are biologically active and may include other alterations, such as amino acid substitutions, modifications, or deletions in other parts of the protein.

The term "variant" refers to nucleotide and amino acid sequences that are substantially identical or similar to the nucleotide and amino acid sequences provided, respectively. Variants can be naturally occurring, for example, naturally occurring human and non-human nucleotide sequences that encode aggrecanase or aggrecanase-like proteins, or be generated artificially. Examples of variants are aggrecanases resulting from alternative splicing of the aggrecanase mRNA, including both 3' and 5' spliced variants of the aggrecanases of the invention, point mutations and other mutations, or proteolytic cleavage of the aggrecanase protein. Variants of aggrecanases of the invention include nucleic acid molecules or fragments thereof and amino acid sequences and fragments thereof, that are substantially identical or similar to other nucleic acids (or their complementary strands when they are optimally aligned (with appropriate insertions or deletions)) or amino acid sequences respectively. In one embodiment, there is at least about 50% identity, at least about 55% identity, at least about 60% identity, at least about 65% identity, at least about 70% identity, at least about 75% identity, at least about 80% identity, at least about 85% identity, at least about 90%, at least about 92% identity, at least about 93% identity, at least about 94% identity, at least about 95% identity, at least about 96% identity, at least about 97% identity, at least about 98% identity, or at least about 99% identity between a nucleic acid molecule or protein of the invention and another nucleic acid molecule or protein respectively, when optimally aligned. Variants, as defined, include both naturally occurring nucleic acid sequences as well as equivalent degenerative codon sequences of the aggrecanases of the invention. Additionally, variants include proteins or polypeptides that exhibit aggrecanase activity, as defined.

To assist in the identification of the sequences listed in the specification and figures, the following table (Table 1) is provided, which lists the SEQ ID NOs, the figure location, and a brief description of each sequence.

TABLE 1

| SEQUENCES | FIGURES | DESCRIPTION |
| --- | --- | --- |
| SEQ ID NO: 1 | FIGS. 1A–1C | full-length nucleotide sequence of ADAMTS-5 (aggrecanase-2) |
| SEQ ID NO: 2 | FIG. 2 | full-length a.a. sequence of ADAMTS-5 encoded by SEQ ID NO: 1 |
| SEQ ID NO: 3 | FIG. 3 | a nucleotide sequence from nucleotide #123 to nucleotide #2382 of SEQ ID NO: 1 |
| SEQ ID NO: 4 | FIG. 4 | a.a. sequence of a truncated aggrecanase-2 molecule encoded by SEQ ID NO: 3 |
| SEQ ID NO: 5 | FIG. 5 | a nucleotide sequence from nucleotide #123 to nucleotide #2379 of SEQ ID NO: 1 |
| SEQ ID NO: 6 | FIG. 6 | a.a. sequence of a truncated aggrecanase-2 molecule encoded by SEQ ID NO: 5 |
| SEQ ID NO: 7 | FIG. 7 | a nucleotide sequence from nucleotide #123 to nucleotide #2007 of SEQ ID NO: 1 |
| SEQ ID NO: 8 | FIG. 8 | a.a. sequence of a truncated aggrecanase-2 molecule encoded by SEQ ID NO: 7 |
| SEQ ID NO: 9 | FIG. 9 | a nucleotide sequence from nucleotide #123 to nucleotide #1824 of SEQ ID NO: 1 |
| SEQ ID NO: 10 | FIG. 10 | a.a. sequence of a truncated aggrecanase-2 molecule encoded by SEQ ID NO: 9 |
| SEQ ID NO: 11 | FIG. 11 | a.a. sequence of full-length aggrecanase-1 protein encoded by SEQ ID NO: 31 |
| SEQ ID NO: 12 | FIG. 12 | a.a. sequence of truncated aggrecanase-1 protein including a.a #1 Met) through a.a #575 (Pro) encoded by SEQ ID NO: 32 |
| SEQ ID NO: 13 | FIG. 13 | a.a. sequence of truncated aggrecanase-1 protein including a.a. #1 (Met) through a.a. #520 (Ala) encoded by SEQ ID NO: 33 |
| SEQ ID NO: 14 | FIG. 14 | a nucleotide sequence of a recombinant truncated aggrecanase-2 protein with a peptide linker and a streptavidin tag |

TABLE 1-continued

| SEQUENCES | FIGURES | DESCRIPTION |
|---|---|---|
| SEQ ID NO: 15 | FIG. 15 | a.a. sequence of a recombinant aggrecanase-2 protein encoded by SEQ ID NO: 14. |
| SEQ ID NO: 16 | | Primer |
| SEQ ID NO: 17 | | Primer |
| SEQ ID NO: 18 | | Primer |
| SEQ ID NO: 19 | | Primer |
| SEQ ID NO: 20 | | oligonucleotide |
| SEQ ID NO: 21 | | oligonucleotide |
| SEQ ID NO: 22 | | peptide linker |
| SEQ ID NO: 23 | FIG. 18 | streptavidin-tag |
| SEQ ID NO: 24 | | oligonucleotide |
| SEQ ID NO: 25 | | oligonucleotide |
| SEQ ID NO: 26 | | catalytic motif |
| SEQ ID NO: 27 | | Nucleotide insert |
| SEQ ID NO: 28 | | insert containing XhoI site |
| SEQ ID NO: 29 | | 68 bp adapter |
| SEQ ID NO: 30 | FIG. 21 | aggrecanase-2 protein with an E-to-Q mutation at a.a. position 411 |
| SEQ ID NO: 31 | FIGS. 22A and 22B | full-length nucleotide sequence of aggrecanase-1 |
| SEQ ID NO: 32 | FIG. 23 | Nucleotide sequence of a truncated aggrecanase-1 |
| SEQ ID NO: 33 | FIG. 24 | Nucleotide sequence of a truncated aggrecanase-1 | a.a. = amino acid

II. Novel Aggrecanase Molecules

In one embodiment, the nucleotide sequence of a truncated aggrecanase-2 of the invention is set forth in SEQ ID NO: 3, wherein the nucleic acid sequence includes nucleotide #123 through nucleotide #2382 of the full-length nucleic acid sequence of aggrecanase-2, set forth in SEQ ID NO: 1. In another embodiment the nucleotide sequence of a truncated aggrecanase-2 is set forth in FIG. 5 from nucleotide #1 through nucleotide #2256. In another embodiment the nucleotide sequence of a truncated aggrecanase-2 of the invention comprises nucleotide #1 through #1884 set forth in FIG. 7, which comprises deletion of a nucleotide sequence encoding a TSP domain. In yet another embodiment, the nucleic acid sequence of a truncated aggrecanase-2 protein of the invention comprises nucleotide #1 through nucleotide #1701 which encodes an aggrecanase-2 protein having both TSP domains deleted. The invention further includes naturally occurring nucleic acid sequences and fragments and variants thereof, as well as those that are artificially generated and equivalent degenerative codon sequences of the sequence described above as set forth in FIGS. 3, 5, 7, and 9, as well as fragments thereof which encode polypeptides that exhibit aggrecanase activity.

In another embodiment, the nucleotide sequences of the invention include nucleic acid sequences that encode truncated aggrecanase-1 molecules. For example, a truncated aggrecanase-1 protein, as set forth in FIG. 12, can be encoded by the nucleic acid sequence set forth in FIG. 23 (SEQ ID NO: 32). Yet another truncated aggrecanase-1 protein of the invention is set forth in FIG. 13, which includes deletion of a TSP domain. A nucleic acid sequence that encodes such a truncated aggrecanase-1 protein is set forth in FIG. 24 (SEQ ID NO: 33).

The amino acid sequence of an isolated truncated aggrecanase-2 molecule is set forth in FIG. 4 from amino acid #1 (Met) through #753 (Glu). The invention further features amino acid sequences encoded by nucleotide sequences of FIGS. 5, 7, and 9, which encode truncated aggrecanase-2 proteins, amino acid sequences of which are set forth in: FIG. 6 including amino acid #1 (Met) through #752 (Pro); FIG. 8 including amino acid #1 (Met) through amino acid #628 (Phe); and FIG. 10 including amino acid #1 (Met) through amino acid #567 (His). The invention further includes amino acid sequences for truncated aggrecanase-1 molecules. The amino acid sequence for a truncated aggrecanase-1 molecule is set forth in FIG. 23, which may be encoded by the nucleotide sequence of FIG. 12. Yet another truncated aggrecanase-1 molecule of the invention is featured in FIG. 13, which may be encoded by the nucleic acid sequence of FIG. 24. The invention further includes fragments and variants of the amino acid sequences of polypeptides that exhibit aggrecanase activity.

A human aggrecanase protein of the invention or a fragment thereof may be produced by culturing a cell transformed with a DNA sequence of FIG. 3 from nucleotide #1 through #2259 and recovering and purifying from the culture medium a protein characterized by the amino acid sequence set forth in. FIG. 4 from amino acid #1 (Met) through #753 (Glu) substantially free from other proteinaceous materials with which it is co-produced.

In another embodiment, the aggrecanase protein of the invention may be produced by culturing a cell transformed with the DNA sequence of FIG. 5 from nucleotide #1 through nucleotide #2256 and recovering and purifying the aggrecanase protein comprising an amino acid sequence of FIG. 6 from amino acid #1 (Met) through amino acid #752 (Pro). In another embodiment, the aggrecanase protein of the invention may be produced by culturing a cell transformed with the DNA sequence of FIG. 5 from nucleotide #1 to nucleotide #2256 with an additional GAA following CCT and recovering and purifying the aggrecanase protein comprising an amino acid sequence of FIG. 4 from amino acid #1 (Met) through amino acid #753 (Glu). In yet another embodiment aggrecanase proteins of the present invention may be produced by culturing a cell transformed with the DNA sequence of FIGS. 1A–1C (SEQ ID NO: 1) and recovering and purifying a truncated aggrecanase protein from the culture medium comprising amino acid #1 through amino acid #752 (SEQ ID NO: 6), or amino acid #1 through amino acid #753 (SEQ ID NO: 4), produced due to cleavage of the full-length aggrecanase-2 protein set forth in SEQ ID NO: 2.

In a further embodiment, a protein recovered from a cell culture medium includes amino acids #1 through #628 (SEQ ID NO: 8); amino acids #1 though 567 (SEQ ID NO: 10); amino acids #1 through #575 (SEQ ID NO: 12) or amino acids #1 through #520 (SEQ ID NO: 13). Purified expressed proteins are substantially free from other proteinaceous materials with which they are co-produced, as well as from other contaminants. A recovered purified protein is contemplated to exhibit proteolytic aggrecanase activity by cleaving aggrecan. Thus, proteins of the invention may be further characterized by their ability to demonstrate aggrecan proteolytic activity in an assay which determines the presence of an aggrecan-degrading molecule. These assays or the development thereof is within the knowledge of one skilled in the art. Such assays may involve contacting an aggrecan substrate with the aggrecanase molecule and monitoring the production of aggrecan fragments (see, for example, Hughes et al., Biochem J 305:799–804 (1995); Mercuri et al., J. Bio Chem. 274:32387–32395 (1999)).

For production in mammalian cells, the DNA sequence further comprises a DNA sequence encoding a suitable propeptide 5' to and linked in frame to the nucleotide sequence encoding an aggrecanase enzyme. Aggrecanase proteins of the invention recovered from a culture medium are purified by isolating them from other proteinaceous materials with which they are co-produced and from other contaminants present. The isolated and purified proteins may be characterized by the ability to cleave aggrecan substrate.

Aggrecanase proteins provided herein also include proteins encoded by the sequences similar to those of FIG. 3 from nucleotide #1 through #2259; FIG. 5 from nucleotide #1 through nucleotide #2256; FIG. 7 from nucleotide #1 through nucleotide #1884; FIG. 9 from nucleotide #1 through nucleotide #1701; FIG. 23 from nucleotide #1 through nucleotide #1725; and FIG. 24 from nucleotide #1 through nucleotide #1560, but into which modifications or deletions are naturally provided (e.g., allelic variations in the nucleotide sequence which may result in amino acid changes in the polypeptide) or deliberately engineered. For example, synthetic polypeptides may wholly or partially duplicate continuous sequences of the amino acid residues of FIG. 4 from amino acid #1 (Met) through amino acid #753 (Glu); FIG. 6 from amino acid #1 (Met) through #752 (Pro); FIG. 8 from amino acid #1 (Met) through amino acid #628 (Phe); FIG. 10 from amino acid #1 (Met) through amino acid #567 (His); FIG. 12 from amino acid #1 (Met) through amino acid #575 (Pro); or FIG. 13 from amino acid #1 (Met) through amino acid #520 (Ala). These sequences, by virtue of sharing primary, secondary, or tertiary structural and conformational characteristics with aggrecanase molecules, may possess biological properties in common therewith.

It is known, for example, that numerous conservative amino acid substitutions are possible without significantly modifying the structure and conformation of a protein, thus maintaining the biological properties as well. For example, it is recognized that conservative amino acid substitutions may be made among amino acids with basic side chains, such as lysine (Lys or K), arginine (Arg or R) and histidine (His or H); amino acids with acidic side chains, such as aspartic acid (Asp or D) and glutamic acid (Glu or E); amino acids with uncharged polar side chains, such as asparagine (Asn or N), glutamine (Gln or Q), serine (Ser or S), threonine (Thr or T), and tyrosine (Tyr or Y); and amino acids with nonpolar side chains, such as alanine (Ala or A), glycine (Gly or G), valine (Val or V), leucine (Leu or L), isoleucine (Ile or I), proline (Pro or P), phenylalanine (Phe or F), methionine (Met or M), tryptophan (Trp or W), and cysteine (Cys or C). Thus, these modifications and deletions of the native aggrecanase may be employed as biologically active substitutes for naturally occurring aggrecanase and in the development of inhibitors of other polypeptides in therapeutic processes. It can be readily determined whether a given variant of aggrecanase maintains the biological activity of aggrecanase by subjecting both aggrecanase and the variant of aggrecanase, as well as inhibitors thereof, to the assays described in the examples.

The invention also includes aggrecanase molecules comprising amino acid substitutions that increase the stability of the aggrecanase molecules. For example, the amino acid sequence of an aggrecanase-2 molecule with an E-to-Q mutation at position 411 of the protein is provided in SEQ ID NO: 30. FIG. 17 further provides schematic representations of amino acid mutations E-to-Q within the catalytic domains of truncated aggrecanase-1 molecules of FIGS. 12 and 13. Although the E-to-Q mutation is in the active site of the molecule and serves to prevent degradation of aggrecanases of the invention, and to thereby increase stability and half-life of aggrecanases, it is contemplated that amino acid mutations can be made in other regions of the protein that increase stability of aggrecanase molecules.

In one embodiment, active site mutations are introduced into aggrecanases to intentionally block the catalytic activity of the enzyme. This is especially useful for the purposes of crystallization and structural determination of aggrecanases and subsequently to identify and develop inhibitors of aggrecanases. Increased stability of truncated or active-site mutant aggrecanases of the invention makes it possible to purify and isolate large amounts of aggrecanase molecules for subsequent use in the development of inhibitors for treatment of diseases. The E-to-Q mutation makes the aggrecanases biologically inactive, thereby enabling purification of inactive protein in large amounts for use in gene therapy in patients and also for development of inhibitors.

Desired amino acid substitutions (whether conservative or non-conservative) can be determined by those skilled in the art at the time such substitutions are desired. For example, amino acid substitutions can be used to identify important amino acid residues of the proteins or polypeptides of the invention or to increase or decrease the activity of the aggrecanases of the invention described. Exemplary amino acid substitutions are set forth in Table 2.

TABLE 2

Amino Acid Substitutions

| Original Residues | Exemplary Substitutions | More Conservative Substitutions |
|---|---|---|
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4 Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

In certain embodiments, conservative amino acid substitutions also encompass non-naturally occurring amino acid residues which are typically incorporated by chemical peptide synthesis rather than by synthesis in biological systems.

Other specific mutations of the sequences of aggrecanase proteins described herein involve modifications of glycosylation sites. These modifications may involve O-linked or N-linked glycosylation sites. For instance, the absence of glycosylation or only partial glycosylation results from amino acid substitution or deletion at asparagine-linked glycosylation recognition sites. The asparagine-linked-glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Additionally, bacterial expression of aggrecanase-related protein will also result in production of a non-glycosylated protein, even if the glycosylation sites are left unmodified.

III. Aggrecanase Nucleotide Sequences

Nucleic acids within the scope of the invention include isolated DNA and RNA sequences that hybridize to the native aggrecanase DNA sequences disclosed under conditions of moderate to high stringency. Conditions of high stringency generally refer to hybridization and washing conditions that employ higher temperatures and lower salt concentrations. Additionally, inclusion of formamide also increases stringency. For example, hybridization conditions at 60–65° C. in the absence of formamide or at 42° C. with 50% formamide, are both high stringency conditions.

Further included in the present invention are DNA sequences which hybridize under high to moderate stringent conditions with the DNA sequence of SEQ ID NOs: 3, 5, 7, 9, 32, or 33 and encode a truncated aggrecanase protein having the ability to cleave aggrecan. In one embodiment, DNA sequences include those which hybridize under high stringent conditions (see Maniatis et al., *Molecular Cloning: A Laboratory Manual*, Cold Spring Harbor Laboratory, pgs. 387–389 (1982)). Such stringent conditions comprise, for example, 0.1×SSC/0.1% SDS at 65° C. DNA sequences identified by hybridization include, for example, DNA sequences that encode a protein which is at least about 80% identical, at least about 90% identical, or at least about 95% identical to the sequence of the proteins of the invention, for example, amino acid sequences set forth in SEQ ID NOs: 4, 6, 8, 10, 12, and 13. DNAs that are equivalents to the DNAs of SEQ ID NOs: 3, 5, 7, 9, 32, or 33 will also hybridize under moderately stringent conditions to the DNA sequence encoding the peptide sequence of SEQ ID NO: 4, 6, 8, 10, 12, or 13, respectively. It is understood, however, that under certain conditions, nucleic acid molecules that encode truncated proteins will hybridize to nucleic acid molecules encoding full-length proteins.

Conditions of moderate stringency are known in the art and are defined by Sambrook et al., *Molecular Cloning: A Laboratory Manual*, Vol. 1, Cold Spring Harbor Press (2$^{nd}$ ed. 1989). In one embodiment, for example, conditions of moderate stringency include use of a prewashing solution of 5×SSC, 0.5% SDS, 1.0 mM EDTA (pH 8.0), and hybridization conditions of about 55° C.–60° C. temperature and washing overnight in 5×SSC overnight at about 55° C. The skilled artisan will recognize that the conditions may be adjusted as necessary according to factors such as the length and composition of the nucleic acid sequences.

Still a further aspect of the invention are DNA sequences encoding truncated aggrecanases having aggrecanase proteolytic activity or other yet undisclosed or undiscovered activities of aggrecanases.

In yet another embodiment, nucleic acids of the invention include nucleic acid molecules that encode aggrecanases comprising mutations that lead to increase in stability of such molecules.

Finally, allelic or other variations of the sequences of the invention, for example, SEQ ID NOs: 3, 5, 7, 9, 32, and 33, encoding amino acid sequences set forth in SEQ ID NOs: 4, 6, 8, 10, 12, and 13 respectively, or peptide sequence variants of aggrecanases of the invention that have aggrecanase activity, are also included in the present invention. Additionally, the present invention includes fragments of the DNA sequences of the invention and variants of such sequences that encode a protein with aggrecanase activity.

Similarly, DNA sequences that code for aggrecanase proteins but which differ in codon sequence due to the degeneracies of the genetic code or allelic variations (naturally occurring base changes in the species population which may or may not result in an amino acid change) also encode novel aggrecanases described herein. Variations in the DNA sequences of FIGS. 1, 3, 5, 7, 9, 31, 32, and 33, which are caused by point mutations or by induced modifications (including insertion, deletion, and substitution) to enhance the activity, half-life, or production of the polypeptides encoded are also encompassed in the invention.

Another aspect of the present invention includes vectors for use in a method of expression of these novel aggrecanase polypeptides. Preferably, vectors of the invention contain a DNA sequence described above which encodes a truncated aggrecanase or an active site mutant aggrecanase of the invention. Additionally, vectors contain appropriate expression control sequences permitting expression of aggrecanase protein sequences of the invention. Alternatively, vectors incorporating modified sequences as described above are also embodiments of the present invention. Additionally, the sequence of FIG. 3 from nucleotide #1 through #2259, or FIG. 5 from nucleotide #1 through #2256, or FIG. 7 from nucleotide #1 through nucleotide #1884, or FIG. 9 from nucleotide #1 through nucleotide #1701, or FIG. 23 from nucleotide #1 through nucleotide #1726, or FIG. 24 from nucleotide #1 through nucleotide #1561, or other sequences encoding aggrecanase proteins could be manipulated to express composite aggrecanase molecules. Thus, the present invention includes chimeric DNA molecules encoding an aggrecanase protein comprising a fragment from nucleotide sequences set forth in SEQ ID NOs: 3, 5, 7, 9, 32, and 33 linked in correct reading frame to a DNA sequence encoding another aggrecanase polypeptide. A DNA molecule as set forth in SEQ ID NOs: 3, 5, 7, 9, 32, or 33, or a variant or fragment thereof, may be linked either 5' or 3' to a DNA molecule encoding another aggrecanase.

IV. Production of Aggrecanase Proteins

Another aspect of the present invention provides methods for producing aggrecanase proteins. In one embodiment, a method of the present invention involves culturing a suitable cell line, which has been transformed with a DNA sequence encoding an aggrecanase protein of the invention under the control of known regulatory sequences. The transformed host cells are cultured and the aggrecanase proteins are recovered and purified from the culture medium. The purified proteins are substantially free from other proteins with which they are co-produced, as well as from other contaminants.

Suitable cells or cell lines may be mammalian cells, such as Chinese hamster ovary cells (CHO). The selection of suitable mammalian host cells and methods for transformation, culture, amplification, screening, product production, and purification are known in the art. See, e.g., Gething and Sambrook, Nature, 293:620–625 (1981), Kaufman et al., Mol. Cell. Biol., 5(7):1750–1759 (1985), or Howley et al., U.S. Pat. No. 4,419,446. Another suitable mammalian cell line, which is described in the accompanying examples, is the monkey COS-1 cell line. The mammalian cell line CV-1 may also be suitable.

Bacterial cells may also be suitable hosts. For example, the various strains of *E. coli* (e.g., HB101, MC1061) are well-known as host cells in the field of biotechnology. Various strains of *B. subtilis, Pseudomonas*, other bacilli, and the like may also be employed in this method. For expression of aggrecanase proteins of the invention in bacterial cells, DNA encoding the propeptide of an aggrecanase is generally not necessary.

Many strains of yeast cells known to those skilled in the art may also be available as host cells for expression of polypeptides of the present invention. Additionally, where desired, insect cells may be utilized as host cells in the method of the present invention. See, e.g. Miller et al., Genetic Engineering, 8:277–298, Plenum Press (1986) and references cited therein.

Various vectors disclosed may be employed in the method of transforming cell lines and usually contain selected regulatory sequences in operative association with the DNA coding sequences of the invention which are capable of directing the replication and expression thereof in selected host cells. Regulatory sequences for such vectors are known to those skilled in the art and may be selected, depending upon the host cells. Such selection is routine and does not form part of the present invention.

One skilled in the art can construct mammalian vectors by employing a nucleic acid sequence disclosed, for example, SEQ ID NOs: 1, 3, 5, 7, 9, 31, 32, and 33.

Truncated aggrecanase proteins of the invention can also be expressed as fusion proteins including the protein sequence. For example, the sequence set forth in SEQ ID NO: 4, 6, 8, 10, 12, or 13, or a fragment or a variant thereof, and, for example, a tag (i.e., a second protein or at least one amino acid) from about 2 to 50 amino acids, or from about 50 to about 100 amino acids, which are added to the amino terminus of, the carboxy terminus of, or any point within the amino acid sequence of an aggrecanase protein, or a fragment or variant thereof. Typically, such amino acid tags are made to stabilize the resulting fusion protein or to simplify purification of an expressed recombinant form of the corresponding aggrecanase protein or a fragment or a variant of such protein, including, for example, a truncated form of an aggrecanase protein of the invention. Such tags are known in the art. Representative examples of such tags include sequences which encode a series of histidine residues, the epitope tag FLAG, the Herpes simplex glycoprotein D, beta-galactosidase, maltose binding protein, streptavidin tag, or glutathione S-transferase. In one embodiment, a nucleic acid sequence encoding a tag is linked in frame to a nucleic acid sequence encoding an aggrecanase of the invention for subsequent production of a recombinant or fusion aggrecanase protein including the tag. Such recombinant or fusion aggrecanase proteins include, for example, truncated aggrecanase-1 enzymes with a C-terminal FLAG tag, as shown in FIG. 17, and truncated aggrecanase-2 enzymes with a C-terminal streptavidin tag, as shown in FIG. 18. A nucleic acid sequence encoding a truncated aggrecanase-2 protein comprising a streptavidin tag is set forth in FIG. 14 (SEQ ID NO: 14), which encodes a truncated aggrecanase-2 fusion protein as set forth in FIG. 15.

Similarly, aggrecanases that contain amino acid mutations which lead to increased stability, expression levels, and/or half-lives can also be produced as fusion proteins using, for example, the amino acid sequence set forth in SEQ ID NO: 30, or a fragment or variant thereof, and, for example, a tag as discussed above. Examples of aggrecanase-1 and -2 fusion proteins of the invention, including aggrecanases with amino acid mutations in their catalytic domain, are set forth in FIGS. 14, 15, 17, and 18.

V. Generation of Antibodies

Isolated proteins of the present inventions may be used to generate antibodies, either monoclonal or polyclonal, to aggrecanase and/or other aggrecanase-related proteins, using methods of antibody production that are generally known in the art. Thus, the present invention also includes antibodies to aggrecanase or other related proteins. The antibodies include both antibodies that block aggrecanase activity and antibodies that do not. The antibodies may be useful for detection and/or purification of aggrecanase or related proteins, or for inhibiting or preventing the effects of aggrecanase. Aggrecanases of the invention or portions thereof may be utilized to prepare antibodies that specifically bind to aggrecanase.

Antibodies can be made, for example, via traditional hybridoma techniques (Kohler and Milstein, Nature 256: 495497 (1975)), recombinant DNA methods (for example, U.S. Pat. No. 4,816,567), or phage display techniques using antibody libraries (Clackson et al., Nature 352: 624–628 (1991); Marks et al., J. Mol. Biol. 222:581–597 (1991)). For various antibody production techniques, see Antibodies: A Laboratory Manual, eds. Harlow et al., Cold Spring Harbor Laboratory (1988).

Antibodies of the invention may be used in the treatment of the diseases described below. Antibodies can also be used in the assays and methods of detection described.

VI. Development of Inhibitors

Various conditions such as osteoarthritis are known to be characterized by degradation of aggrecan. Therefore, truncated aggrecanases of the invention and aggrecanases with mutations that lead to increased stability and expression levels of aggrecanases, make it possible to generate aggrecanase molecules in large amounts in order to develop inhibitors to aggrecanases.

The invention therefore provides compositions comprising an aggrecanase inhibitor. Inhibitors may be developed using an aggrecanase molecule of the invention in screening assays involving a mixture of aggrecan substrate with an inhibitor of aggrecanase activity followed by exposure to aggrecan. Inhibitors can be screened using high throughput processes, such as by screening a library of inhibitors. Inhibitors can also be made using three-dimensional structural analysis and/or computer aided drug design. The method may entail determination of binding sites for inhibitors based on the three-dimensional structure of aggrecanase and aggrecan and developing molecules reactive with a binding site on aggrecanase or aggrecan. Candidate molecules are assayed for inhibitory activity. Additional standard methods for developing inhibitors of aggrecanase molecules are known to those skilled in the art. An assay for identification and development of aggrecanase inhibitors involves, for example, contacting a mixture of aggrecan and an inhibitor with an aggrecanase molecule followed by measurement of the degree of aggrecanase inhibition, for instance, by detection and measurement of aggrecan fragments produced by cleavage at an aggrecanase susceptible site. Inhibitors may be proteins, peptides, antibodies, or chemical compounds. In one embodiment, inhibitors are peptide molecules that bind an active site on aggrecanase molecules. For example, active site mutants of aggrecanase-1 and aggrecanase-2 molecules can be used for the development of peptide inhibitors. Aggrecanase-1 molecules that comprise an E-to-Q amino acid change within the catalytic domain are set forth in FIG. 17. Similarly, the amino acid sequence of an aggrecanase-2 molecule with an E-to-Q change at position 411 within the catalytic domain is set forth in FIG. 21 (SEQ ID NO: 30).

VII. Disease Treatment and Diagnosis

Inhibitors of aggrecanase activity may be used in the treatment of diseases described below. Inhibitors can also be used in the assays and methods of detection described. Various diseases that are contemplated as being treatable by using inhibitors of aggrecanases of the invention include, but are not limited to, osteoarthritis, cancer, inflammatory joint disease, rheumatoid arthritis, septic arthritis, periodontal diseases, corneal ulceration, proteinuria, coronary thrombosis from atherosclerotic plaque rupture, aneurysmal aortic disease, inflammatory bowel disease, Crohn's disease, emphysema, acute respiratory distress syndrome, asthma, chronic obstructive pulmonary disease, Alzheimer's disease, brain and hematopoietic malignancies, osteoporosis, Parkinson's disease, migraine, depression, peripheral neuropathy, Huntington's disease, multiple sclerosis, ocular angiogenesis, macular degeneration, aortic aneurysm, myocardial infarction, autoimmune disorders, degenerative cartilage loss following traumatic joint injury, head trauma, dystrophobic epidermolysis bullosa, spinal cord injury, acute and chronic neurodegenerative diseases, osteopenias, tempero mandibular joint disease, demyelating diseases of the nervous system, organ transplant toxicity and rejection, cachexia, allergy, tissue ulcerations, restenosis, and other diseases characterized by altered aggrecanase activity or altered aggrecanase level.

Inhibitors and antibodies of the invention that inhibit activity of aggrecanases and/or compounds that lower expression of aggrecanases may be used in the treatment of any disease in a mammal that involves degradation of the extracellular matrix. An effective amount of at least one of aggrecanase antibodies or inhibitors, in a pharmaceutically acceptable vehicle, can be used for treatment of diseases, such as osteoarthritis, or other diseases disclosed which are characterized by degradation of matrix proteins, such as aggrecan, by aggrecanases and aggrecanase-related proteins.

VIII. Administration

Another aspect of the invention provides pharmaceutical compositions containing a therapeutically effective amount of an aggrecanase inhibitor or antibody. Therefore, these compositions of the invention may be used in the treatment of diseases characterized by the degradation of aggrecan by an aggrecanase enzyme or a protein with aggrecanase-like activity.

The invention includes methods for treating patients suffering from conditions characterized by a degradation of aggrecan. These methods, according to the invention, entail administering to a patient needing such treatment an effective amount of a composition comprising an aggrecanase inhibitor which inhibits the proteolytic activity. It is contemplated that inhibitors of the invention may function either by inhibiting aggrecanase activity or simply by regulating levels of aggrecanases in a disease state.

Inhibitors of the present invention are useful to diagnose or treat various medical disorders in humans or animals. In one embodiment, the antibodies of the invention can be used to inhibit or reduce at least one activity associated with an aggrecanase protein, relative to an aggrecanase protein not bound by the same antibody. In one embodiment, inhibitors of the invention can inhibit or reduce at least one of the activities of an aggrecanase molecule relative to the aggrecanase that is not bound by an antibody. In certain embodiments, an activity of an aggrecanase, when bound by at least one of the presently disclosed antibodies, is inhibited at least 50%, may be inhibited at least 60, 62, 64, 66, 68, 70, 72, 72, 76, 78, 80, 82, 84, 86, or 88%, may be inhibited at least 90, 91, 92, 93, or 94%, or may be inhibited at least 95% to 100% relative to the aggrecanase protein that is not bound by at least one of the presently disclosed antibodies.

Generally, compositions of the present are administered to a patient so that antibodies or their binding fragments are administered at a dose ranging from about 1 µg/kg to about 20 mg/kg, about 1 µg/kg to about 10 mg/kg, about 1 µg/kg to about 1 mg/kg, about 10 µg/kg to about 1 mg/kg, about 10 µg/kg to about 100 µg/kg, about 100 µg to about 1 mg/kg, or about 500 µg/kg to about 1 mg/kg. Antibodies are administered as a bolus dose, to maximize the interval of time that the antibodies can circulate in the patient's body following their administration to the patient. Continuous infusion may also be used after an initial bolus dose In another embodiment, the invention is directed to administration of inhibitors of aggrecanases, such as proteins, peptides, antibodies, and chemical compounds. The effective amount of an inhibitor is a dosage which is useful for reducing activity of aggrecanases to achieve a desired biological outcome. Generally, appropriate therapeutic dosages for administering an inhibitor may range, for example, from about 5 mg to about 100 mg, from about 15 mg to about 85 mg, from about 30 mg to about 70 mg, or from about 40 mg to about 60 mg. Inhibitors can be administered in one dose, or at intervals such as once daily, once weekly, or once monthly. Dosage schedules for administration of an aggrecanase inhibitor can be adjusted based on, for example, the affinity of the inhibitor for its aggrecanase target, the half-life of the inhibitor, and the severity of the patient's condition. Generally, inhibitors are administered as a bolus dose, to maximize their circulating levels. Continuous infusions may also be used after the bolus dose.

Toxicity and therapeutic efficacy of such compounds can be determined by standard pharmaceutical procedures in cell culture or experimental animal models, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Inhibitors, which exhibit large therapeutic indices, are generally preferred.

The data obtained from cell culture assays and animal studies can be used in formulating a range of dosages for use in humans. The dosage of such compounds may lie within a range of circulating concentrations that exhibit an $ED_{50}$ with little or no toxicity. The dosage may vary within this range depending upon the dosage form employed and the route of administration utilized. For any inhibitor used according to the present invention, a therapeutically effective dose can be estimated initially from cell culture assays. A dose may be formulated in animal models to achieve a circulating plasma concentration range that exhibits an $IC_{50}$ (i.e., the concentration of the test antibody which achieves a half-maximal inhibition of symptoms) as determined by cell culture assays. Levels in plasma may be measured, for example, by high performance liquid chromatography. The effects of any particular dosage can be monitored by suitable bioassays. Examples of suitable bioassays include DNA replication assays, transcription-based assays, GDF protein/receptor binding assays, creatine kinase assays, assays based on the differentiation of pre-adipocytes, assays based on glucose uptake in adipocytes, and immunological assays.

Therapeutic methods of the invention include administering an aggrecanase inhibitor composition topically, systemically, or locally as an implant or a device. The dosage regimen for the administration of composition will be determined by the attending physician based on various factors which modify the action of the aggrecanase protein, the site of pathology, the severity of disease, the patient's age, sex, and diet, the severity of any inflammation, time of administration and other clinical factors. Generally, systemic or injectable administration will be initiated at a dose which is minimally effective, and the dose will be increased over a preselected time course until a positive effect is observed. Subsequently, incremental increases in dosage will be made limiting to levels that produce a corresponding increase in effect, while taking into account any adverse affects that may appear. The addition of other known factors to a final composition may also affect the dosage.

Progress can be monitored by periodic assessment of disease progression. The progress can be monitored, for example, by X-rays, MRI or other imaging modalities, synovial fluid analysis, and/or clinical examination.

IX. Assays and Methods of Detection

The inhibitors and antibodies of the invention can be used in assays and methods of detection to determine the presence or absence of, or quantify aggrecanase in a sample. The inhibitors and antibodies of the present invention may be used to detect aggrecanase proteins, in vivo or in vitro. By correlating the presence or level of these proteins with a disease, one of skill in the art can diagnose the associated disease or determine its severity. Diseases that may be diagnosed by the presently disclosed inhibitors and antibodies are set forth above.

Detection methods for use with antibodies are well known in the art and include ELISA, radioimmunoassay, immunoblot, western blot, immunofluorescence, immuno-precipitation, and other comparable techniques. The antibodies may further be provided in a diagnostic kit that incorporates at least one of these techniques to detect a protein (e.g., an aggrecanase protein). Such a kit may contain other components, packaging, instructions, or other material to aid the detection of an aggrecanase protein, and instructions regarding use of the kit. When protein inhibitors, for example, peptide inhibitors, are used in such diagnostic assays, protein—protein interaction assays can be employed.

Where inhibitors are intended for diagnostic purposes, it may be desirable to modify them, for example, with a ligand group (such as biotin) or a detectable marker group (such as a fluorescent group, a radioisotope or an enzyme). If desired, the antibodies (whether polyclonal or monoclonal) may be labeled using conventional techniques. Suitable labels include fluorophores, chromophores, radioactive atoms, electron-dense reagents, enzymes, and ligands having specific binding partners. Enzymes are typically detected by their activity. For example, horseradish peroxidase can be detected by its ability to convert tetramethylbenzidine (TMB) to a blue pigment, quantifiable with a spectrophotometer. Other suitable binding partners include biotin and avidin or streptavidin, IgG and protein A, and the numerous receptor-ligand couples known in the art.

The following examples illustrate practice of the present invention in isolating and characterizing human aggrecanase and other aggrecanase-related proteins, obtaining the human proteins and expressing the proteins via recombinant techniques.

EXAMPLES

Example 1

Cloning of ADAMTS-5 (Aggrecanase-2)

PCR primers were designed to the published sequence for human ADAMTS-5 (GenBank Accession #AF142099). The full-length coding sequence for ADAMTS-5 was amplified from a human uterus cDNA library (Genetics Institute/Wyeth Research) using the Advantage-GC PCR kit (Clontech).

ADAMTS-5 was isolated using PCR. Tissue expression pattern of aggrecanase-5 was determined by PCR amplification of 7 different oligo dT-primed human cDNA libraries including placenta, brain, muscle, lung, heart, uterus, and spinal cord. PCR primers that amplified 5' and 3' regions of the ADAMTS-5 cDNA were used. Primer sequences for amplifying the 5' portion of ADAMTS-5 were as follows: 5' primer: 5'GACTGACTGAATTCATACCCATAAAGTC-CCAGTCGCGCA (SEQ ID NO: 16), which incorporated an 8 bp tail (GACTGACT), and an EcoR1 site (GAATTC) upstream of the start codon (ATG) of the ADAMTS-5 sequence and 3' primer: 5'CAGGGCTTAGATGCATCMT-GCTGG (SEQ ID NO: 17). Primer sequences for amplifying 3' portion of ADAMTS-5 were as follows: 5' primer: 5' TACCAGCATTGATGCATCTAAGCCCT (SEQ ID NO: 18) and 3' primer 5' AAATGGGCGCGGCCGCTGCATCG-GTGCTGAATCCTCCAGTTATCT (SEQ ID NO: 19), which incorporated an 8 bp tail (AAATGGGC) and a Not1 site (GCGGCCGC) downstream of the stop codon (TAG) for ADAMTS-5. PCR products of the appropriate size, 5' amplification product of 1404 bp and 3' amplification product of 1519 bp were found using a uterus cDNA library as substrate. The Advantage-GC PCR Kit from Clontech was used for the PCR reactions. Reaction conditions were those recommended by the manufacturer, with the following exceptions: the amount of GC Melt used was 10 µl per 50 µl reaction; the amount of Not1 linearized library used was 0.2 ng/µl reaction; and the amount of each oligo used was 2 pmol/ul reaction. Cycling conditions were as follows: 95° C. for 1 min, one cycle; followed by 30 cycles consisting of 95° C. for 15 sec/68° C. for 2 min. The 2 overlapping PCR products resulting from the amplifications were digested with EcoR1 and Nsi1 (5' product) or Nsi1 and Not1 (3' product) and ligated into the CHO expression vector pHTop_new, digested with EcoR1 and Not1 using standard ligation enzyme, buffers and conditions. Ligated products were used to transform ElectroMAX DH10B cells from Life Technologies (Carlsbad, Calif.). Cloned PCR fragments of ADAMTS-5 were sequenced to verify sequence.

Nucleotide sequence for full-length ADAMTS-5 protein was the consensus sequence derived from the PCR products. Two silent changes were reflected in this sequence as compared to the published sequence for ADAMTS-5. These changes were a G to an A at nucleotide #711 and an A to a G at nucleotide #2046 (numbering starts at 1 for the A of the ATG start codon for ADAMTS-5). The full-length cDNA, including an open reading frame (ORF) for ADAMTS-5 ORF and 5' and 3' untranslated regions (UTRs), was subcloned into the mammalian expression vector pED6-dpc2.

A cDNA expressing the full-length human aggrecanase-2 (hAgg-2)/ADAMTS-5 protein was cloned into the expression plasmid pHTop. This plasmid was derived from pED (Kaufman et al., Nucleic Acids Res. 19:4485–4490 (1991) by removing the majority of the adenomajor late promoter and inserting six repeats of the tet operator (Gossen and Bujard, Proc. Natl. Acad. Sci. U.S.A. 89:5547–5551 (1992)). A CHO cell line stably expressing hAgg-2 was obtained by transfecting pHTop/hAgg-2 into CHO/A2 cells and selecting clones in 0.05 µM methotrexate. Clones were screened for Aggrecanase-2 expression by western analysis of conditioned media using a polyclonal antibody specific for Aggrecanase-2. The CHO/A2 cell line was derived from CHO DUKX B11 cells (Urlaub and Chasin, Proc. Natl. Acad. Sci. U.S.A. 77:4216–4220 (1980)) by stably integrating a transcriptional activator, a fusion between the tet repressor and the herpes virus VP16 transcription activation domain (Gossen and Bujard, Proc. Natl. Acad. Sci. U.S.A. 89:5547–5551 (1992)).

A truncated ADAMTS-5 protein including a C-terminal protein purification tag was constructed using 3 DNA fragments from the full-length ADAMTS-5 construct described above and a synthetic DNA duplex. ADAMTS-5 was truncated at amino acid residue 752 (Pro) of the full-length aggrecanase protein. Proline at 752 in the full-length protein is N-terminal of a cleavage site in the full-length protein. The 3 DNA fragments consisted of a 5777 bp SgrA1/Not1 fragment containing the pHTop_new vector backbone and a 5' portion of ADAMTS-5, a 1756 bp SgrA1/BspH1 fragment containing ADAMTS-5, and a 304 bp BspH1/BsrG1 fragment containing ADAMTS-5. The 4 oligonucleotide fragments used to build the 110 bp synthetic duplex were as follows: oligonucleotide fragment 1: 5'GTACAAAGAT-TGTTGGAACCTTTATAGAAAA GTAAGGGTTACACT-GACGTGGTGAGGATTC (SEQ ID NO: 20); oligonucleotide fragment 2: 5'CTGGATCCGGATCTGCTTGGAGCCAC-CCGCAGTTCGAAA AATAAGGC (SEQ ID NO: 21) which encodes a GSGSA (SEQ ID NO: 22) peptide linker followed by a WSHPQFEK (SEQ ID NO: 23) Strep-tag II protein purification tag from IBA fused C-terminus to amino acid 752 of the truncated ADAMTS-5 protein, oligonucleotide fragment 3: 5' GGCCGCCTTATTTTTCGAACT-GCGGGTGGCTC CAAGCAGATCCGGATCCAG-GAATCCTCAC (SEQ ID NO: 24) and oligonucleotide fragment 4: 5'CACGTCAGTGTAACCCTTACTTTCTTAT-TAAAGGTTCCAACA ATCTTT (SEQ ID NO: 25). Each oligonucleotide fragment was diluted to a final concentration of 10 pmol/µl with sterile water. Equal volumes (10 µl each) of oligonucleotide fragments 1 and 4 were mixed. Equal volumes (10 µl each) of oligonucleotide fragments 2 and 3 were mixed. Mixtures were heated to 95° C. for 5 minutes and then allowed to cool to room temperature. 1 µl of each mixture was used in the final ligation with the 3 ADAMTS-5 DNA fragments described above. Standard ligation enzyme, buffers, and conditions were used. Ligated products were used to transform ElectroMAX DH10B cells from Life Technologies (Carlsbad, CA). The cloned synthetic oligonucleotides were sequenced to determine fidelity and verify sequence. FIG. 18 is a schematic representation of Streptavidin-tagged aggrecanase-2 proteins of the invention.

Example 2

Expression of ADAMTS-5-wild type(WT) and Active Site Mutant (ASM)

CHO/A2 cells were transfected with ADAMTS-5-WT or ASM expression vectors using Lipofectin (Life Technologies, Inc.). The cells were plated in the presence of 0.02, 0.05, and 0.1 mM Methotrexate (MTX) selection and incubated at 37° C., 5% $CO_2$ for 2 weeks. Colonies were picked and expanded into cell lines while cultured in selection medium.

In another experiment, CHO cells were transfected with active site mutants for aggrecanase-1, as depicted in FIG. 17.

Example 3

Subcloning of ADAMTS-5 Active Site Mutant

The E411-Q411 point mutation in ADAMTS-5 was generated using the QuickChange Site-Directed Mutagenesis Kit (Stratagene, La Jolla, Calif.). Mutagenesis was performed on pHTop/Agg-2 using the QuickChange Site Directed Mutation Kit (Stratagene, catalog #200518). The single base pair mutation, 2597-G to 2597-C, resulted in a single amino acid change at position 411 (E-to-Q) in the catalytic domain of aggrecanase-2 protein (SEQ ID NO: 30). This mutation was shown to inactivate the catalytic activity of mini-stromelysin-1 (Steele et al., Protein Engineering 13:397405(2000)). A CHO cell line stably expressing hAgg-2(E411 Q) active site mutant was obtained by transfecting pHTop/hAgg-2(E411Q) into CHO/A2 cells and selecting clones in 0.05 µM methotrexate. Clones were screened for Aggrecanase-2 expression by western analysis of conditioned media using a polyclonal antibody specific for Aggrecanase-2.

Additionally, E-to-Q mutation in the active site of aggrecanase-1 molecules of the invention is generated. FIG. 17 is a schematic representation of recombinant truncated aggrecanase-1 molecules of the invention that include an E-to-Q mutation in the catalytic domain. Nucleic acid sequences encoding these aggrecanase-1 molecules are cloned into an appropriate vector, for example, pHTop disclosed, and subsequently transfected into an appropriate cell line, for example, CHO cells. Stable transfectants for aggrecanases of the invention can be selected as described above. Expression levels of active site aggrecanase mutants can be detected using an antibody specific for the aggrecanase being expressed.

Example 4

Western Blotting

Conditioned medium from CHO cells expressing ADAMTS-5 WT or ASM were loaded on a 12% SDS-PAGE gel under reducing conditions. The samples were then transferred to a nitrocellulose membrane. ADAMTS-5 protein was detected by a polyclonal antibody against ADAMTS-5, followed by goat-anti-rabbit IgG-HRP and a chemiluminescent substrate (Pierce, Milwaukee, Wis.).

In another experiment, conditioned medium from CHO cells expressing truncated aggrecanase-2 proteins was loaded onto a 12% SDS-PAGE. The results of such an experiment are shown in FIG. 19. Briefly, CHO cells were transfected with a nucleic acid encoding either truncated aggrecanase-2 from amino acid #1 through amino acid #567, or truncated aggrecanase-2 from amino acid #1 through amino acid #628, or a nucleic acid expressing a full-length aggrecanase-2 molecule. Stable CHO cell lines were developed expressing either aggrecanase-2 from amino acid #1 through #567, or from amino acid #1 through #628, or the full-length aggrecanase-2 molecule. Cells were subsequently harvested for proteins and expression levels for the various aggrecanase-2 molecules was determined by Western blot analysis using an antibody specific to aggrecanase-2. As demonstrated by the experiment set forth in FIG. 19, truncated aggrecanase proteins are expressed at higher levels, due to higher stability, as compared with the full-length aggrecanase-2 protein.

Example 5

Microcapillary HPLC-Mass Spectrometry

Recombinant ADAMTS-5-WT or ASM proteins were purified by HP-HPLC and further analyzed by 1D-SDS-polyacrylamide gel electrophoresis. Proteins were visualized by Coommassie blue staining, and protein bands of interest were excised manually, then reduced, alkylated and digested with trypsin or endopeptidase Lys-C (Promega, Madison, Wis.) in situ using an automated in-gel digestion robot. After digestion, the peptide extracts were concentrated and separated by microelectrospray reverse-phase HPLC. Peptide analyses were done on a Finnigan LCQ ion trap mass spectrometer (ThermoQuest, San Jose, Calif.). Automated analysis of MS/MS data was performed using the SEQUEST computer algorithm incorporated into the Finnigan Bioworks data analysis package (ThermoQuest, San Jose, Calif.) using the database of proteins derived from the complete genome.

Example 6

Biological Activity of Expressed Aggrecanase

To measure the biological activity of the expressed aggrecanase proteins; for example, truncated aggrecanases of the invention disclosed, the proteins are recovered from the cell culture and purified by isolating the aggrecanase-related proteins from other proteinaceous materials with which they are co-produced as well as from other contaminants. Purification is carried out using standard techniques known to those skilled in the art. The isolated protein may be assayed in accordance with the following assays:

Assays specifically to determine if the protein is an enzyme capable of cleaving aggrecan at the aggrecanase cleavage site:

Fluorescent peptide assay: Expressed protein is incubated with a synthetic peptide which encompasses amino acids at the aggrecanase cleavage site of aggrecan. Either the N-terminus or the C-terminus of the synthetic peptide is labeled with a fluorophore and the other terminus includes a quencher. Cleavage of the peptide separates the fluorophore and quencher and elicits fluorescence. From this assay it is determined that the expressed aggrecanase protein can cleave aggrecan at the aggrecanase site and that relative fluorescence is a determination of the relative activity of the expressed protein.

Neoepitope western: Expressed aggrecanase protein is incubated with intact aggrecan. After several biochemical manipulations of the resulting sample (dialysis, chondroitinase treatment, lyophilization, and reconstitution) the sample is run on an SDS PAGE gel. The gel is incubated with an antibody that is specific to a site on aggrecan which is only exposed after aggrecanase cleavage. The gel is transferred onto nitrocellulose paper and developed using a secondary antibody (called a western assay) which subsequently results in a banding pattern indicative of products with a molecular weight consistent with aggrecanase generated cleavage products of aggrecan. This assay results in the finding that the expressed aggrecanase protein cleaved native aggrecan at the aggrecanase cleavage site, and also gives the molecular weight of the cleavage products. Relative density of the bands can give an indication of relative aggrecanase activity.

Assay to determine if an expressed protein can cleave aggrecan anywhere in the protein (not specific to the aggrecanase site).

Aggrecan ELISA: Expressed protein is incubated with intact aggrecan which had been previously adhered to plastic wells. The wells are washed and then incubated with an antibody that detects aggrecan. The wells are developed with a secondary antibody. If the original amount of aggrecan remains in the wells, the antibody staining is dense. Whereas, if aggrecan was digested by aggrecanase activity of the expressed aggrecanase protein, the aggrecan comes off the plate and the subsequent staining of the aggrecan-coated wells by the antibody is reduced. This assay tells whether an expressed protein is capable of cleaving aggrecan (anywhere in the protein, not only at the aggrecanase site) and can further determine relative aggrecan cleavage.

The results of one such experiment are shown in FIG. 20, where aggrecan cleavage was detected after incubation of aggrecan with truncated aggrecanase-2 molecules using a 3B3 ELISA assay. The results of such an experiment, shown in FIG. 20 include % aggrecan cleavage subsequent to incubation with truncated aggrecanases, for example, aggrecanase-2 from amino acid #1 through #567 and aggrecanase-2 from amino acid #1 through #628. As shown in FIG. 20, truncated aggrecanases of the invention having one or both TSP domains deleted are biologically active.

Protein analysis of isolated proteins is conducted using standard techniques such as SDS-PAGE acrylamide (Laemmli, Nature 227:680–685 (1970)) stained with silver (Oakley, et al., Anal Biochem. 105:361–363 (1980)) and by immunoblot (Towbin, et al., Proc. Natl. Acad. Sci. USA 76:4350–4354 (1979)). Using the above described assays, expressed aggrecanase-related proteins are evaluated for their activity and useful aggrecanase-related molecules are identified.

Activity Assay: Mirotiter plates (Costar) were coated with hyaluronic acid (ICN), followed by chondroitinase (Seikagaku Chemicals)-treated bovine aggrecan. Conditioned medium from CHO cells expressing WT ADAMTS-5 or ADAMTS-5 ASM was added to the aggrecan-coated plates. Aggrecan cleaved at the $E^{373}$-$A^{374}$ within the interglobular domain was washed away. The remaining uncleaved aggrecan was detected with the 3B3 antibody (ICN), followed by anti-IgM-HRP secondary antibody (Southern Biotechnology). Final color development was with 3,3", 5,5" tetramethylbenzidine (TMB, BioFx Laboratories).

ADAMTS-5 is synthesized in the inactive pro-form (~90 kDa) and can be processed by furin to yield the mature species of ~70 kDa. Conditioned medium from CHO lines transfected with ADAMTS-5 expressed a small amount of active, mature protein. The predominant species expressed was a protein of ~55 kDa, representing a cleavage product of the mature protein.

Conditioned medium from the CHO stable lines transfected with ADAMTS-5 showed that the enzyme was cleaved to yield a species of ~55 kDa. Mass spectrometry and N-terminal sequencing of the clipped form revealed that the cleavage occurred between $E^{753}$-$G^{754}$ residues in the spacer domain. In the presence of EDTA or a non-specific hydroxamate metalloprotease inhibitor, the full-length mature protein, ~70 kDa, was preserved. This cleavage is autocatalytic and not due to an enzyme present in the CHO conditioned medium. Site-specific mutagenesis was performed to mutate the $E^{411}$-$Q^{411}$ within the catalytic HELGH motif (SEQ ID NO: 26) of ADAMTS-5. Stable CHO lines were made with this ADAMTS-5 active site-mutant (ADAMTS-5 ASM). Conditioned medium from CHO stable lines transfected with ADAMTS-5 ASM lacked aggrecanase activity as shown by ELISA (FIG. 16). The full-length ~70 kDa protein rather than the clipped 55 kDa form, was predominant in a western blot of conditioned media from CHO cells expressing ADAMTS-5 ASM.

The above described examples demonstrate that recombinant ADAMTS-5 was susceptible to proteolytic cleavage at residue $E^{753}$-$G^{754}$ in the spacer domain. This cleavage reduced the size of the mature protein to ~55 kDa and was inhibited by EDTA and a non-specific hydroxamate metalloprotease inhibitor. A point mutation in the catalytic domain of ADAMTS-5 inactivated the enzymatic activity of the protein and protected the full-length protein from cleavage. It is therefore contemplated that the proteolytic processing was autocatalytic and not due to a protease present in the conditioned medium of the CHO cells.

Example 7

Expression of Aggrecanase

In order to produce murine, human, or other mammalian aggrecanase-related proteins, the DNA encoding it is transferred into an appropriate expression vector and introduced into mammalian cells or other preferred eukaryotic or prokaryotic hosts including insect host cell culture systems by conventional genetic engineering techniques. Expression system for biologically active recombinant human aggrecanase is contemplated to be stably transformed mammalian cells, insect, yeast, or bacterial cells.

One skilled in the art can construct mammalian expression vectors by employing the nucleotide sequence of FIG. 3 from nucleotide #1 through #2259; nucleotide sequence of FIG. 5 from nucleotide #1 through nucleotide #2256; nucleic acid sequence of FIG. 7 from nucleotide #1 through nucleotide #1884; or nucleic acid sequence of FIG. 9 from nucleotide #1 through nucleotide #1701 or other DNA sequences encoding aggrecanases or aggrecanase-like proteins or other modified sequences and known vectors, such as pCD (Okayama and Berg, Mol. Cell Biol., 2:161–170 (1982)), pJL3, pJL4 (Gough et al., EMBO J., 4:645–653 (1985)) and pMT2 CXM.

The mammalian expression vector pMT2 CXM is a derivative of p91023(b) (Wong et al., Science 228:810–815, 1985) differing from the latter in that it contains the ampicillin resistance gene in place of the tetracycline resistance gene and further contains a XhoI site for insertion of cDNA clones. The functional elements of pMT2 CXM have been described (Kaufman, R. J., Proc. Natl. Acad. Sci. USA 82:689–693 (1985)) and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in *E. coli*.

Plasmid pMT2 CXM is obtained by EcoRI digestion of pMT2-VWF, which has been deposited with the American Type Culture Collection (ATCC), Rockville, Md. (USA) under accession number ATCC 67122. EcoRI digestion excises the cDNA insert present in pMT2-VWF, yielding pMT2 in linear form which can be ligated and used to transform *E. coli* HB 101 or DH-5 to ampicillin resistance. Plasmid pMT2 DNA can be prepared by conventional methods pMT2 CXM is then constructed using loopout/in mutagenesis (Morinaga et al., Biotechnology 84: 636–639 (1984)). This removes bases 1075 to 1145 relative to the Hind III site near the SV40 origin of replication and enhancer sequences of pMT2. In addition it inserts the following sequence:

5' PO-CATGGGCAGCTCGAG 3' (SEQ ID NO:27) at nucleotide #1145. This sequence contains the recognition site for the restriction endonuclease Xho I. A derivative of pMT2CXM, termed pMT23, contains recognition sites for the restriction endonucleases PstI, EcoRI, SalI, and XhoI. Plasmid pMT2 CXM and pMT23 DNA may be prepared by conventional methods.

pEMC2β1 derived from pMT21 may also be suitable in practice of the invention. pMT21 is derived from pMT2 which is derived from pMT2-VWF. As described above EcoRI digestion excises the cDNA insert present in PMT-VWF, yielding pMT2 in linear form which can be ligated and used to transform *E. Coli* HB 101 or DH-5 to ampicillin resistance. Plasmid pMT2 DNA can be prepared by conventional methods.

pMT21 is derived from pMT2 through the following two modifications. First, 76 bp of the 5' untranslated region of the DHFR cDNA including a stretch of 19 G residues from G/C tailing for cDNA cloning is deleted. In this process, a XhoI site is inserted to obtain the following sequence immediately upstream from DHFR:

```
                                              (SEQ ID NO:28)
5'-CTGCAGGCGAGCCTGAATTCCTCGAGCCATCATG
         PstI         EcoRI XhoI
```

Second, a unique ClaI site is introduced by digestion with EcoRV and XbaI, treatment with Klenow fragment of DNA polymerase 1, and ligation to a ClaI linker (CATCGATG). This deletes a 250 bp segment from the adenovirus associated RNA (VAI) region but does not interfere with VAI RNA gene expression or function. pMT21 is digested with EcoRI and XhoI, and used to derive the vector pEMC2B1.

A portion of the EMCV leader is obtained from pMT2-ECAT1 (Jang et al., J. Virol 63:1651–1660 (1989)) by digestion with EcoRI and PstI, resulting in a 2752 bp fragment. This fragment is digested with TaqI yielding an EcoRI-TaqI fragment of 508 bp which is purified by electrophoresis on low melting agarose gel. A 68 bp adapter and its complementary strand are synthesized with a 5' TaqI protruding end and a 3' XhoI protruding end which has the following sequence:

```
5' CGAGGTTAAAAAACGTCTAGGCCCCCCGAACCACGGGGACGTGGTTTTCCTTT    (SEQ ID NO:29)
   TaqI

GAAAAACACGATTGC 3'
        XhoI
```

This sequence matches the EMC virus leader sequence from nucleotide #763 to #827. It also changes the ATG at position 10 within the EMC virus leader to an ATT and is followed by a XhoI site. A three way ligation of the pMT21 EcoRI-16hol fragment, the EMC virus EcoRI-TaqI fragment, and the 68 bp oligonucleotide adapter TaqI-16hol adapter resulting in the vector pEMC2β1.

This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence, in appropriate relationships to direct the high level expression of the desired cDNA in mammalian cells.

The construction of vectors may involve modification of the aggrecanase-related DNA sequences. For instance, a cDNA encoding an aggrecanase can be modified by removing the non-coding nucleotides on the 5' and 3' ends of the coding region. The deleted non-coding nucleotides may or may not be replaced by other sequences known to be beneficial for expression. These vectors are transformed into appropriate host cells for expression of aggrecanase or aggrecanase-like proteins. Additionally, the sequence of FIG. 3 from nucleotide #1 through nucleotide #2259, or FIG. 5 from nucleotide #1 through nucleotide #2256, or FIG. 7 from nucleotide #1 through nucleotide #1884, or FIG. 9 from nucleotide #1 through nucleotide #1701, or fragments of variants thereof or other sequences encoding aggrecanases of the invention or proteins that have aggrecanase activity can be manipulated to express an aggrecanase or aggrecanase-like protein by deleting aggrecanase encoding propeptide sequences and replacing them with sequences encoding the complete propeptides of other aggrecanase proteins.

One skilled in the art can manipulate the sequences of FIG. 3 from nucleotide #1 through nucleotide #2259; or FIG. 5 from nucleotide #1 through nucleotide #2256; or FIG. 7 from nucleotide #1 through nucleotide #1884; or FIG. 9 from nucleotide #1 through nucleotide #1701; or nucleotide sequences encoding aggrecanases molecules of FIGS. 12 and 13 set forth in FIGS. 23 and 24, or fragments and variants thereof, by eliminating or replacing the mammalian regulatory sequences flanking the coding sequence with bacterial sequences to create bacterial vectors for intracellular or extracellular expression of truncated aggrecanase molecules. For example, the coding sequences could be further manipulated (e.g. ligated to other known linkers or modified by deleting non-coding sequences therefrom or altering nucleotides therein by other known techniques). A modified aggrecanase encoding sequence could then be inserted into a known bacterial vector using procedures such as described in T. Taniguchi et al., Proc. Natl Acad. Sci. USA, 77:5230–5233 (1980). This exemplary bacterial vector could then be transformed into bacterial host cells to express an aggrecanase protein of the invention. For a strategy for producing extracellular expression of aggrecanase-related proteins in bacterial cells, see, e.g. European patent application EP 177,343.

Similar manipulations can be performed for construction of an insect vector (see, e.g., procedures described in published European patent application EP 155,476) for expression in insect cells. A yeast vector could also be constructed employing yeast regulatory sequences for intracellular or extracellular expression of the factors of the present invention by yeast cells. (See, e.g., procedures described in published PCT application WO 86/00639 and European patent application EP 123,289).

A method for producing high levels of an aggrecanase-related protein of the invention in mammalian, bacterial, yeast, or insect host cell systems may involve the construction of cells containing multiple copies of the heterologous aggrecanase-related gene. The heterologous gene is linked to an amplifiable marker, e.g., the dihydrofolate reductase (DHFR) gene for which cells containing increased gene copies can be selected for propagation in increasing concentrations of methotrexate (MTX) according to the procedures of Kaufman and Sharp, J. Mol. Biol., 159:601–629 (1982). This approach can be employed with a number of different cell types.

For example, a plasmid containing a DNA sequence for an aggrecanase or aggrecanase-like protein of the invention in operative association with other plasmid sequences enabling expression thereof and the DHFR expression plasmid pAdA26SV(A)3 (Kaufman and Sharp, Mol. Cell. Biol., 2:1304–1319 (1982)) can be co-introduced into DHFR-deficient CHO cells, DUKX-BII, by various methods including calcium phosphate coprecipitation and transfection, electroporation or protoplast fusion. DHFR expressing transformants are selected for growth in alpha media with dialyzed fetal calf serum, and subsequently selected for amplification by growth in increasing concentrations of MTX (e.g. sequential steps in 0.02, 0.2, 1.0 and 5 µM MTX) as described in Kaufman et al., Mol Cell Biol., 5:1750–1759 (1985). Transformants are cloned, and biologically active aggrecanase expression is monitored by at least one of the assays described above. Aggrecanase protein expression should increase with increasing levels of MTX resistance. Aggrecanase polypeptides are characterized using standard techniques known in the art such as pulse labeling with $^{35}$S methionine or cysteine and polyacrylamide gel electrophoresis. Similar procedures can be followed to produce other aggrecanases or aggrecanase-like proteins.

In one example, an aggrecanase nucleotide sequence of the present invention is cloned into the expression vector pED6 (Kaufman et al., Nucleic Acid Res. 19:4485–4490 (1991)). COS and CHO DUKX B11 cells are transiently transfected with an aggrecanase sequence of the invention (+/−co-transfection of PACE on a separate pED6 plasmid) by lipofection (LF2000, Invitrogen). Duplicate transfections are performed for each molecule of interest: (a) one transfection set for harvesting conditioned media for activity assay and (b) one transfection set for 35-S-methionine/cysteine metabolic labeling.

On day one media is changed to DME(COS) or alpha (CHO) media +1% heat-inactivated fetal calf serum +/−100 µg/ml heparin on wells of set (a) to be harvested for activity assay. After 48 h (day 4), conditioned media is harvested for activity assay.

On day 3, the duplicate wells of set (b) were changed to MEM (methionine-free/cysteine free) media +1% heat-inactivated fetal calf serum +100 µg/ml heparin+100 µCi/ml 35S-methionine/cysteine (Redivue Pro mix, Amersham). Following 6 h incubation at 37° C., conditioned media is harvested and run on SDS-PAGE gels under reducing conditions. Proteins are visualized by autoradiography.

Example 8

Biological Activity of Expressed Aggrecanase

To measure the biological activity of the expressed aggrecanase-related proteins obtained in the examples above, the proteins are recovered from the cell culture and purified by isolating the aggrecanase-related proteins from other proteinaceous materials with which they are co-produced as well as from other contaminants. The purified protein may be assayed in accordance with assays described above. Purification is carried out using standard techniques known to those skilled in the art.

Protein analysis is conducted using standard techniques such as SDS-PAGE acrylamide (Laemmli, Nature 227: 680–685 (1970)) stained with silver (Oakley et al., Anal.

Biochem. 105:361–363 (1980)) and by immunoblot (Towbin et al., Proc. Natl. Acad. Sci. USA 76:4350–4354 (1979)).

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

---

We claim:

1. An isolated, recombinantly-produced or chemically-synthesized aggrecanase consisting of an amino acid sequence at least 95% identical to an amino acid sequence selected from the group consisting of SEQ ID NOs: 4, 6 and 8, or fragments thereof, wherein said fragments retain aggrecanase activity.

2. An isolated, recombinantly-produced or chemically-synthesized fusion protein consisting of:
   comprising the aggrecanase of claim 1 and
   at least one peptide tag.

* * * * *

UNITED STATES PATENT AND TRADEMARK OFFICE
CERTIFICATE OF CORRECTION

PATENT NO.       : 7,150,983 B2                                              Page 1 of 1
APPLICATION NO.  : 10/358283
DATED            : December 19, 2006
INVENTOR(S)      : Georgiadis et al.

It is certified that error appears in the above-identified patent and that said Letters Patent is hereby corrected as shown below:

Claim 2, line 2, delete "consisting of:".

Signed and Sealed this

Twenty-sixth Day of February, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,150,983 B2 |
| APPLICATION NO. | : 10/358283 |
| DATED | : December 19, 2006 |
| INVENTOR(S) | : Georgiadis et al. |

Page 1 of 1

It is certified that error appears in the above-identified patent and that said Letters Patent is hereby corrected as shown below:

Column 102
    Claim 2, line 2, delete "consisting of:".

This certificate supersedes the Certificate of Correction issued February 26, 2008.

Signed and Sealed this

Eighteenth Day of March, 2008

JON W. DUDAS
*Director of the United States Patent and Trademark Office*

SEQUENCE LISTING

<160> NUMBER OF SEQ ID NOS: 33

<210> SEQ ID NO 1
<211> LENGTH: 5533
<212> TYPE: DNA
<213> ORGANISM: Homo sapiens

<400> SEQUENCE: 1

```
cttgactcaa tcctgcaagc aagtgtgtgt gtgtccccat ccccgcccc gttaacttca      60
tagcaaataa caaataccca taaagtccca gtcgcgcagc ccctcccgc gggcagcgca     120
ctatgctgct cgggtgggcg tccctgctgc tgtgcgcgtt ccgcctgccc ctggccgcgg    180
tcggccccgc cgcgacacct gcccaggata aagccgggca gcctccgact gctgcagcag    240
ccgcccagcc ccgccggcgg caggggagg aggtgcagga gcgagccgag cctcccggcc     300
acccgcaccc cctggcgcag cggcgcagga gcaagggct ggtgcagaac atcgaccaac     360
tctactccgg cggcggcaag gtgggctacc tcgtctacgc gggcggccgg aggttcctct    420
tggacctgga gcgagatggt tcggtgggca ttgctggctt cgtgcccgca ggaggcggga    480
cgagtgcgcc ctggcgccac cggagccact gcttctatcg gggcacagtg gacgctagtc    540
cccgctctct ggctgtcttt gacctctgtg ggggtctcga cggcttcttc gcggtcaagc    600
acgcgcgcta caccctaaag ccactgctgc gcggaccctg ggcggaggaa gaaaaggggc    660
gcgtgtacgg ggatgggtcc gcacggatcc tgcacgtcta caccgcgag ggcttcagct     720
tcgaggccct gccgccgcgc gccagctgcg aaacccccgc gtccacaccg gaggcccacg    780
agcatgctcc ggcgcacagc aacccgagcg gacgcgcagc actggcctcg cagctcttgg    840
accagtccgc tctctcgccc gctggggct caggaccgca gacgtggtgg cggcggcggc      900
gccgctccat ctcccgggcc cgccaggtgg agctgcttct ggtggctgac gcgtccatgg    960
cgcggttgta tggccgggc ctgcagcatt acctgctgac cctggcctcc atcgccaata   1020
ggctgtacag ccatgctagc atcgagaacc acatccgcct ggccgtggtg aaggtggtgg    1080
tgctaggcga caaggacaag agcctggaag tgagcaagaa cgctgccacc acactcaaga   1140
acttttgcaa gtggcagcac caacacaacc agctgggaga tgaccatgag gagcactacg    1200
atgcagctat cctgttttact cgggaggatt tatgtgggca tcattcatgt gacaccctgg    1260
gaatggcaga cgttgggacc atatgttctc cagagcgcag ctgtgctgtg attgaagacg    1320
atggcctcca cgcagccttc actgtggctc acgaaatcgg acatttactt ggcctctccc    1380
atgacgattc caaattctgt gaagagacct ttggttccac agaagataag cgcttaatgt    1440
cttccatcct taccagcatt gatgcatcta agccctggtc caaatgcact tcagccacca    1500
tcacagaatt cctggatgat ggccatggta actgtttgct ggacctacca cgaaagcaga    1560
tcctgggccc cgaagaactc ccaggacaga cctacgatgc cacccagcag tgcaacctga    1620
cattcgggcc tgagtactcc gtgtgtcccg gcatggatgt ctgtgctcgc ctgtggtgtg    1680
ctgtggtacg ccagggccag atggtctgtc tgaccaagaa gctgcctgcg gtggaaggga    1740
cgccttgtgg aaagggggaga atctgcctgc agggcaaatg tgtggacaaa accaagaaaa   1800
```

```
aatattattc aacgtcaagc catggcaact ggggatcttg gggatcctgg ggccagtgtt    1860
ctcgctcatg tggaggagga gtgcagtttg cctatcgtca ctgtaataac cctgctccca    1920
gaaacaacgg acgctactgc acagggaaga gggccatcta ccgctcctgc agtctcatgc    1980
cctgcccacc caatggtaaa tcatttcgtc atgaacagtg tgaggccaaa aatggctatc    2040
agtctgatgc aaaaggagtc aaaacttttg tggaatgggt tcccaaatat gcaggtgtcc    2100
tgccagcgga tgtgtgcaag ctgacctgca gagccaaggg cactggctac tatgtggtat    2160
tttctccaaa ggtgaccgat ggcactgaat gtaggccgta cagtaattcc gtctgcgtcc    2220
gggggaagtg tgtgagaact ggctgtgacg gcatcattgg ctcaaagctg cagtatgaca    2280
agtgcggagt atgtggagga gacaactcca gctgtacaaa gattgttgga acctttaata    2340
agaaaagtaa gggttacact gacgtggtga ggattcctga aggggcaacc cacataaaag    2400
ttcgacagtt caaagccaaa gaccagacta gattcactgc ctatttagcc ctgaaaaaga    2460
aaaacggtga gtaccttatc aatggaaagt acatgatctc cacttcagag actatcattg    2520
acatcaatgg aacagtcatg aactatagcg gttggagcca cagggatgac ttcctgcatg    2580
gcatgggcta ctctgccacg aaggaaattc taatagtgca gattcttgca acagacccca    2640
ctaaaccatt agatgtccgt tatagctttt ttgttcccaa gaagtccact ccaaaagtaa    2700
actctgtcac tagtcatggc agcaataaag tgggatcaca cacttcgcag ccgcagtggg    2760
tcacgggccc atggctcgcc tgctctagga cctgtgacac aggttggcac accagaacgg    2820
tgcagtgcca ggatgaaaac cggaagttag caaaaggatg tcctctctcc caaaggcctt    2880
ctgcgtttaa gcaatgcttg ttgaagaaat gttagcctgt ggttatgatc ttatgcacaa    2940
agataactgg aggattcagc accgatgcag tcgtggtgaa caggaggtct acctaacgca    3000
cagaaagtca tgcttcagtg acattgtcaa caggagtcca attatgggca gaatctgctc    3060
tctgtgacca aaagaggatg tgcactgctt cacgtgacag tggtgacctt gcaatataga    3120
aaaacttggg agttattgaa catcccctgg gattacaaga aacactgatg aatgtaaaat    3180
caggggacat ttgaagatgg cagaactgtc tcccccttgt cacctacctc tgatagaatg    3240
tctttaatgg tatcataatc attttcaccc ataatacaca gtagcttctt cttactgttt    3300
gtaaatacat tctcccttgg tatgtcactt tatatcccct ggttctatta aaatatccat    3360
atatatttct ataaaaaaag tgtttgacca agtaggtct gcagctattt caacttcctt    3420
ccgtttccag aaagagctgt ggatatttta ctggaaatta agaacttgct gctgttttaa    3480
taagatgtag tatattttct gactacagga gataaaattt cagtcaaaaa accattttga    3540
cagcaagtat cttctgagaa attttgaaaa gtaaatagat ctcagtgtat ctagtcactt    3600
aaatacatac acgggttcat ttacttaaaa cctttgactg cctgtatttt tttcaggtag    3660
ctagccaaat taatgcataa tttcagatgt agaagtaggg tttgcgtgtg tgtgtgtgat    3720
catactcaag agtctaaaaa ctagtttcct tgtgttggaa atttaaaagg aaaaaaatcg    3780
tatttcactg tgttttcaat ttatattttc acaactactt tctctctcca gagctttcat    3840
ctgatatctc acaatgtatg atatacgtac aaaaacacaca gcaagttttc tatcatgtcc    3900
aacacattca acactggtat acctcctacc agcaagcctt taaaatgcgt tgtgtttgc    3960 ttatttgttt tgttcaaggg ttcagtaaga cctacaatgt tttgtatttc ttgacttatt    4020
ttattagaaa cattaaagat cacttggtag ttagccacat tgagaagtgg ttatcattgt    4080
taatgtggtt aatgccaaaa agtggttaat attaataaga ctgttccac accataggca    4140 ataatttctt aatttaaaaa atctaagtat attcctattg tactaaatat ttttcccaac    4200
```

```
tggaaagcac ttgattgtac ccgtaagtgt ttgagtgatg acatgtgatg attttcagaa    4260
agttgttgtt tttgtttcca tagcctgttt aagtaggttg taagtttgaa tagttagaca    4320
tggaaattat tttataagca cacacctaaa gatatctttt tagatgataa aatgtacacc    4380
cccccatcac caacctcaca acttagaaaa tctaagttgt ttgatttcat tgggatttct    4440
tttgttgtga aacactgcaa agccaatttt tctttataaa aattcatagt aatcctgcca    4500
aatgtgccta ttgttaaaga tttgcatgtg aagatcttag ggaaccactg tttgagttct    4560
acaagctcat gagagtttat ttttattata agatgttttt aatataaaag aattatgtaa    4620
ctgatcacta tattacatca tttcagtggg ccaggaaaat agatgtcttg ctgttttcag    4680
tattttctta agaaattgct tttaaaacaa ataattgttt tacaaaacca ataattatcc    4740
tttgaatttt catagactga ctttgctttc gacgtagaaa ttttttttttc ttaataaatt    4800 atcactttga gaaatgaggc ctgtacaagg ctgataacct atatgtgatg gagatcaccc    4860
aatgccaagg gcagaaagca aacctagtta aataggtgag aaaaaaaata ataatcccag    4920
tgccatttgt ctgtgcaaag agaattagga gagaggttaa tgttactttt ttccattttg    4980
gaaataattt taatcaagta actcaaatgt gacaaaattt atttttattt tttgtggtta    5040
tattcccaac aacattaaaa aatactcgag gcataaatgt agttgtctcc tactctgctt    5100
ctcttactat actcatacat ttttaatatg gtttatcaat gattcatgtt tccctcaaat    5160
agtgatggtt tacacctgtc atggaaacaa tcctagagag ctcagagcaa ttaaaccact    5220
attccatgct tttaagtagt tttctccacc tttttcttat gagtctcact agattgactg    5280
aggaatgtat gtctaaattc ctggagaaga tgatatggat tggaaactga aattcagaga    5340
aatggagtgt tcaatagata ccacgaattg tgaacaaagg gaaaattcta tacaactcaa    5400
tctaagtcag tccactttga cttcgtactg tctttcacct ttccattgtt gcatcttgaa    5460 tttttttaaaa tgtctagaat tcaggatgct aggggctact tctccaaaaa aaaaaaaaaa    5520
aaaaaaaaaa aaa                                                       5533
```

<210> SEQ ID NO 2
<211> LENGTH: 930
<212> TYPE: PRT
<213> ORGANISM: Homo sapiens

<400> SEQUENCE: 2

```
Met Leu Leu Gly Trp Ala Ser Leu Leu Cys Ala Phe Arg Leu Pro
  1               5                  10                  15

Leu Ala Ala Val Gly Pro Ala Ala Thr Pro Ala Gln Asp Lys Ala Gly
                 20                  25                  30

Gln Pro Pro Thr Ala Ala Ala Ala Gln Pro Arg Arg Arg Gln Gly
         35                  40                  45

Glu Glu Val Gln Glu Arg Ala Glu Pro Pro Gly His Pro His Pro Leu
         50                  55                  60

Ala Gln Arg Arg Arg Ser Lys Gly Leu Val Gln Asn Ile Asp Gln Leu
 65                  70                  75                  80

Tyr Ser Gly Gly Gly Lys Val Gly Tyr Leu Val Tyr Ala Gly Arg
                 85                  90                  95

Arg Phe Leu Leu Asp Leu Glu Arg Asp Gly Ser Val Gly Ile Ala Gly
                100                 105                 110

Phe Val Pro Ala Gly Gly Gly Thr Ser Ala Pro Trp Arg His Arg Ser
                115                 120                 125
```

```
His Cys Phe Tyr Arg Gly Thr Val Asp Ala Ser Pro Arg Ser Leu Ala
    130                 135                 140

Val Phe Asp Leu Cys Gly Gly Leu Asp Gly Phe Ala Val Lys His
145                 150                 155                 160

Ala Arg Tyr Thr Leu Lys Pro Leu Leu Arg Gly Pro Trp Ala Glu Glu
                165                 170                 175

Glu Lys Gly Arg Val Tyr Gly Asp Gly Ser Ala Arg Ile Leu His Val
                180                 185                 190

Tyr Thr Arg Glu Gly Phe Ser Phe Glu Ala Leu Pro Arg Ala Ser
        195                 200                 205

Cys Glu Thr Pro Ala Ser Thr Pro Glu Ala His Glu His Ala Pro Ala
    210                 215                 220

His Ser Asn Pro Ser Gly Arg Ala Ala Leu Ala Ser Gln Leu Leu Asp
225                 230                 235                 240

Gln Ser Ala Leu Ser Pro Ala Gly Ser Gly Pro Gln Thr Trp Trp
                245                 250                 255

Arg Arg Arg Arg Arg Ser Ile Ser Arg Ala Arg Gln Val Glu Leu Leu
                260                 265                 270

Leu Val Ala Asp Ala Ser Met Ala Arg Leu Tyr Gly Arg Gly Leu Gln
            275                 280                 285

His Tyr Leu Leu Thr Leu Ala Ser Ile Ala Asn Arg Leu Tyr Ser His
    290                 295                 300

Ala Ser Ile Glu Asn His Ile Arg Leu Ala Val Val Lys Val Val
305                 310                 315                 320

Leu Gly Asp Lys Asp Lys Ser Leu Glu Val Ser Lys Asn Ala Ala Thr
                325                 330                 335

Thr Leu Lys Asn Phe Cys Lys Trp Gln His Gln His Asn Gln Leu Gly
                340                 345                 350

Asp Asp His Glu Glu His Tyr Asp Ala Ala Ile Leu Phe Thr Arg Glu
            355                 360                 365

Asp Leu Cys Gly His His Ser Cys Asp Thr Leu Gly Met Ala Asp Val
    370                 375                 380

Gly Thr Ile Cys Ser Pro Glu Arg Ser Cys Ala Val Ile Glu Asp Asp
385                 390                 395                 400

Gly Leu His Ala Ala Phe Thr Val Ala His Glu Ile Gly His Leu Leu
                405                 410                 415

Gly Leu Ser His Asp Asp Ser Lys Phe Cys Glu Glu Thr Phe Gly Ser
                420                 425                 430

Thr Glu Asp Lys Arg Leu Met Ser Ser Ile Leu Thr Ser Ile Asp Ala
        435                 440                 445

Ser Lys Pro Trp Ser Lys Cys Thr Ser Ala Thr Ile Thr Glu Phe Leu
450                 455                 460

Asp Asp Gly His Gly Asn Cys Leu Leu Asp Leu Pro Arg Lys Gln Ile
465                 470                 475                 480

Leu Gly Pro Glu Glu Leu Pro Gly Gln Thr Tyr Asp Ala Thr Gln Gln
                485                 490                 495

Cys Asn Leu Thr Phe Gly Pro Glu Tyr Ser Val Cys Pro Gly Met Asp
                500                 505                 510

Val Cys Ala Arg Leu Trp Cys Ala Val Arg Gln Gly Gln Met Val
        515                 520                 525

Cys Leu Thr Lys Lys Leu Pro Ala Val Glu Gly Thr Pro Cys Gly Lys
    530                 535                 540

Gly Arg Ile Cys Leu Gln Gly Lys Cys Val Asp Lys Thr Lys Lys Lys
```

```
                545                 550                 555                 560
Tyr Tyr Ser Thr Ser Ser His Gly Asn Trp Gly Ser Trp Gly Ser Trp
                565                 570                 575
Gly Gln Cys Ser Arg Ser Cys Gly Gly Gly Val Gln Phe Ala Tyr Arg
            580                 585                 590
His Cys Asn Asn Pro Ala Pro Arg Asn Asn Gly Arg Tyr Cys Thr Gly
        595                 600                 605
Lys Arg Ala Ile Tyr Arg Ser Cys Ser Leu Met Pro Cys Pro Pro Asn
    610                 615                 620
Gly Lys Ser Phe Arg His Glu Gln Cys Glu Ala Lys Asn Gly Tyr Gln
625                 630                 635                 640
Ser Asp Ala Lys Gly Val Lys Thr Phe Val Glu Trp Val Pro Lys Tyr
                645                 650                 655
Ala Gly Val Leu Pro Ala Asp Val Cys Lys Leu Thr Cys Arg Ala Lys
                660                 665                 670
Gly Thr Gly Tyr Tyr Val Val Phe Ser Pro Lys Val Thr Asp Gly Thr
            675                 680                 685
Glu Cys Arg Pro Tyr Ser Asn Ser Val Cys Val Arg Gly Lys Cys Val
        690                 695                 700
Arg Thr Gly Cys Asp Gly Ile Ile Gly Ser Lys Leu Gln Tyr Asp Lys
705                 710                 715                 720
Cys Gly Val Cys Gly Gly Asp Asn Ser Ser Cys Thr Lys Ile Val Gly
                725                 730                 735
Thr Phe Asn Lys Lys Ser Lys Gly Tyr Thr Asp Val Val Arg Ile Pro
            740                 745                 750
Glu Gly Ala Thr His Ile Lys Val Arg Gln Phe Lys Ala Lys Asp Gln
        755                 760                 765
Thr Arg Phe Thr Ala Tyr Leu Ala Leu Lys Lys Lys Asn Gly Glu Tyr
    770                 775                 780
Leu Ile Asn Gly Lys Tyr Met Ile Ser Thr Ser Glu Thr Ile Ile Asp
785                 790                 795                 800
Ile Asn Gly Thr Val Met Asn Tyr Ser Gly Trp Ser His Arg Asp Asp
                805                 810                 815
Phe Leu His Gly Met Gly Tyr Ser Ala Thr Lys Glu Ile Leu Ile Val
                820                 825                 830
Gln Ile Leu Ala Thr Asp Pro Thr Lys Pro Leu Asp Val Arg Tyr Ser
            835                 840                 845
Phe Phe Val Pro Lys Lys Ser Thr Pro Lys Val Asn Ser Val Thr Ser
        850                 855                 860
His Gly Ser Asn Lys Val Gly Ser His Thr Ser Gln Pro Gln Trp Val
865                 870                 875                 880
Thr Gly Pro Trp Leu Ala Cys Ser Arg Thr Cys Asp Thr Gly Trp His
                885                 890                 895
Thr Arg Thr Val Gln Cys Gln Asp Gly Asn Arg Lys Leu Ala Lys Gly
                900                 905                 910
Cys Pro Leu Ser Gln Arg Pro Ser Ala Phe Lys Gln Cys Leu Leu Lys
            915                 920                 925
Lys Cys
    930

<210> SEQ ID NO 3
<211> LENGTH: 2259
<212> TYPE: DNA
<213> ORGANISM: Homo sapiens
```

<400> SEQUENCE: 3

```
atgctgctcg gtgggcgtc cctgctgctg tgcgcgttcc gcctgcccct ggccgcggtc      60
ggccccgccg cgacacctgc ccaggataaa gccgggcagc ctccgactgc tgcagcagcc    120
gcccagcccc gccggcggca gggggaggag gtgcaggagc gagccgagcc tcccggccac    180
ccgcaccccc tggcgcagcg cgcaggagc aaggggctgg tgcagaacat cgaccaactc    240
tactccggcg cggcaaggt gggctacctc gtctacgcgg gcggccggag gttcctcttg    300
gacctggagc gagatggttc ggtgggcatt gctggcttcg tgcccgcagg aggcgggacg    360
agtgcgccct ggcgccaccg gagccactgc ttctatcggg gcacagtgga cgctagtccc    420
cgctctctgg ctgtctttga cctctgtggg ggtctcgacg gcttcttcgc ggtcaagcac    480
gcgcgctaca ccctaaagcc actgctgcgc ggaccctggg cggaggaaga aaggggcgc    540
gtgtacgggg atgggtccgc acggatcctg cacgtctaca cccgcgaggg cttcagcttc    600
gaggccctgc cgccgcgcgc cagctgcgaa accccgcgt ccacaccgga ggcccacgag    660
catgctccgg cgcacagcaa cccgagcgga cgcgcagcac tggcctcgca gctcttggac    720
cagtccgctc tctcgcccgc tgggggctca ggaccgcaga cgtggtggcg gcggcggcgc    780
cgctccatct cccgggcccg ccaggtggag ctgcttctgg tggctgacgc gtccatggcg    840
cggttgtatg gccgggcct gcagcattac ctgctgaccc tggcctccat cgccaatagg    900
ctgtacagcc atgctagcat cgagaaccac atccgcctgg ccgtggtgaa ggtggtggtg    960
ctaggcgaca aggacaagag cctggaagtg agcaagaacg ctgccaccac actcaagaac   1020
ttttgcaagt ggcagcacca acacaaccag ctgggagatg accatgagga gcactacgat   1080
gcagctatcc tgtttactcg ggaggattta tgtgggcatc attcatgtga cccctggga   1140
atggcagacg ttgggaccat atgttctcca gagcgcagct gtgctgtgat gaagacgat   1200
ggcctccacag cagccttcac tgtggctcac gaaatcggac attacttgg cctctcccat   1260
gacgattcca aattctgtga agagaccttt ggttccacag aagataagcg cttaatgtct   1320
tccatcctta ccagcattga tgcatctaag ccctggtcca atgcacttc agccaccatc   1380
acagaattcc tggatgatgg ccatggtaac tgtttgctgg acctaccacg aaagcagatc   1440
ctgggccccg aagaactccc aggacagacc tacgatgcca cccagcagtg caacctgaca   1500
ttcgggcctg agtactccgt gtgtccggc atggatgtct gtgctcgcct gtggtgtgct   1560
gtggtacgcc agggccagat ggtctgtctg accaagaagc tgcctgcggt ggaagggacg   1620
ccttgtggaa agggagaat ctgcctgcag ggcaaatgtg tggacaaaac caagaaaaaa   1680
tattattcaa cgtcaagcca tggcaactgg ggatcttggg gatcctgggg ccagtgttct   1740
cgctcatgtg gaggaggagt gcagtttgcc tatcgtcact gtaataaccc tgctcccaga   1800
aacaacggac gctactgcac agggaagagg gccatctacc gctcctgcag tctcatgccc   1860
tgcccaccca tggtaaatc atttcgtcat gaacagtgtg aggccaaaaa tggctatcag   1920
tctgatgcaa aaggagtcaa aacttttgtg gaatgggttc caaatatgc aggtgtcctg   1980
ccagcggatg tgtgcaagct gacctgcaga gccaagggca ctggctacta tgtggtattt   2040
tctccaaagg tgaccgatgg cactgaatgt aggccgtaca gtaattccgt ctgcgtccgg   2100
gggaagtgtg tgagaactgg ctgtgacggc atcattggct caaagctgca gtatgacaag   2160
tgcggagtat gtggaggaga caactccagc tgtacaaaga ttgttggaac ctttaataag   2220
aaaagtaagg gttacactga cgtggtgagg attcctgaa                         2259
```

<210> SEQ ID NO 4
<211> LENGTH: 753
<212> TYPE: PRT
<213> ORGANISM: Homo sapiens

<400> SEQUENCE: 4

```
Met Leu Leu Gly Trp Ala Ser Leu Leu Leu Cys Ala Phe Arg Leu Pro
  1               5                  10                  15

Leu Ala Ala Val Gly Pro Ala Ala Thr Pro Ala Gln Asp Lys Ala Gly
             20                  25                  30

Gln Pro Pro Thr Ala Ala Ala Ala Gln Pro Arg Arg Arg Gln Gly
         35                  40                  45

Glu Glu Val Gln Glu Arg Ala Glu Pro Pro Gly His Pro His Pro Leu
     50                  55                  60

Ala Gln Arg Arg Arg Ser Lys Gly Leu Val Gln Asn Ile Asp Gln Leu
 65                  70                  75                  80

Tyr Ser Gly Gly Gly Lys Val Gly Tyr Leu Val Tyr Ala Gly Gly Arg
                 85                  90                  95

Arg Phe Leu Leu Asp Leu Glu Arg Asp Gly Ser Val Gly Ile Ala Gly
            100                 105                 110

Phe Val Pro Ala Gly Gly Thr Ser Ala Pro Trp Arg His Arg Ser
        115                 120                 125

His Cys Phe Tyr Arg Gly Thr Val Asp Ala Ser Pro Arg Ser Leu Ala
    130                 135                 140

Val Phe Asp Leu Cys Gly Gly Leu Asp Gly Phe Phe Ala Val Lys His
145                 150                 155                 160

Ala Arg Tyr Thr Leu Lys Pro Leu Leu Arg Gly Pro Trp Ala Glu Glu
                165                 170                 175

Glu Lys Gly Arg Val Tyr Gly Asp Gly Ser Ala Arg Ile Leu His Val
            180                 185                 190

Tyr Thr Arg Glu Gly Phe Ser Phe Glu Ala Leu Pro Pro Arg Ala Ser
        195                 200                 205

Cys Glu Thr Pro Ala Ser Thr Pro Glu Ala His Glu His Ala Pro Ala
    210                 215                 220

His Ser Asn Pro Ser Gly Arg Ala Ala Leu Ala Ser Gln Leu Leu Asp
225                 230                 235                 240

Gln Ser Ala Leu Ser Pro Ala Gly Gly Ser Gly Pro Gln Thr Trp Trp
                245                 250                 255

Arg Arg Arg Arg Arg Ser Ile Ser Arg Ala Arg Gln Val Glu Leu Leu
            260                 265                 270

Leu Val Ala Asp Ala Ser Met Ala Arg Leu Tyr Gly Arg Gly Leu Gln
        275                 280                 285

His Tyr Leu Leu Thr Leu Ala Ser Ile Ala Asn Arg Leu Tyr Ser His
    290                 295                 300

Ala Ser Ile Glu Asn His Ile Arg Leu Ala Val Val Lys Val Val Val
305                 310                 315                 320

Leu Gly Asp Lys Asp Lys Ser Leu Glu Val Ser Lys Asn Ala Ala Thr
                325                 330                 335

Thr Leu Lys Asn Phe Cys Lys Trp Gln His Gln His Asn Gln Leu Gly
            340                 345                 350

Asp Asp His Glu Glu His Tyr Asp Ala Ala Ile Leu Phe Thr Arg Glu
        355                 360                 365

Asp Leu Cys Gly His His Ser Cys Asp Thr Leu Gly Met Ala Asp Val
    370                 375                 380
```

Gly Thr Ile Cys Ser Pro Glu Arg Ser Cys Ala Val Ile Glu Asp Asp
385                 390                 395                 400

Gly Leu His Ala Ala Phe Thr Val Ala His Glu Ile Gly His Leu Leu
            405                 410                 415

Gly Leu Ser His Asp Asp Ser Lys Phe Cys Glu Thr Phe Gly Ser
            420                 425                 430

Thr Glu Asp Lys Arg Leu Met Ser Ser Ile Leu Thr Ser Ile Asp Ala
        435                 440                 445

Ser Lys Pro Trp Ser Lys Cys Thr Ser Ala Thr Ile Thr Glu Phe Leu
    450                 455                 460

Asp Asp Gly His Gly Asn Cys Leu Leu Asp Leu Pro Arg Lys Gln Ile
465                 470                 475                 480

Leu Gly Pro Glu Glu Leu Pro Gly Gln Thr Tyr Asp Ala Thr Gln Gln
                485                 490                 495

Cys Asn Leu Thr Phe Gly Pro Glu Tyr Ser Val Cys Pro Gly Met Asp
            500                 505                 510

Val Cys Ala Arg Leu Trp Cys Ala Val Val Arg Gln Gly Gln Met Val
        515                 520                 525

Cys Leu Thr Lys Lys Leu Pro Ala Val Glu Gly Thr Pro Cys Gly Lys
530                 535                 540

Gly Arg Ile Cys Leu Gln Gly Lys Cys Val Asp Lys Thr Lys Lys Lys
545                 550                 555                 560

Tyr Tyr Ser Thr Ser His Gly Asn Trp Gly Ser Trp Gly Ser Trp
                565                 570                 575

Gly Gln Cys Ser Arg Ser Cys Gly Gly Val Gln Phe Ala Tyr Arg
            580                 585                 590

His Cys Asn Asn Pro Ala Pro Arg Asn Gly Arg Tyr Cys Thr Gly
            595                 600                 605

Lys Arg Ala Ile Tyr Arg Ser Cys Ser Leu Met Pro Cys Pro Pro Asn
    610                 615                 620

Gly Lys Ser Phe Arg His Glu Gln Cys Glu Ala Lys Asn Gly Tyr Gln
625                 630                 635                 640

Ser Asp Ala Lys Gly Val Lys Thr Phe Val Glu Trp Val Pro Lys Tyr
            645                 650                 655

Ala Gly Val Leu Pro Ala Asp Val Cys Lys Leu Thr Cys Arg Ala Lys
            660                 665                 670

Gly Thr Gly Tyr Tyr Val Val Phe Ser Pro Lys Val Thr Asp Gly Thr
            675                 680                 685

Glu Cys Arg Pro Tyr Ser Asn Ser Val Cys Val Arg Gly Lys Cys Val
690                 695                 700

Arg Thr Gly Cys Asp Gly Ile Ile Gly Ser Lys Leu Gln Tyr Asp Lys
705                 710                 715                 720

Cys Gly Val Cys Gly Gly Asp Asn Ser Ser Cys Thr Lys Ile Val Gly
            725                 730                 735

Thr Phe Asn Lys Lys Ser Lys Gly Tyr Thr Asp Val Val Arg Ile Pro
            740                 745                 750

Glu

<210> SEQ ID NO 5
<211> LENGTH: 2256
<212> TYPE: DNA
<213> ORGANISM: Homo sapiens

<400> SEQUENCE: 5

```
atgctgctcg ggtgggcgtc cctgctgctg tgcgcgttcc gcctgcccct ggccgcggtc      60
ggccccgccg cgacacctgc ccaggataaa gccgggcagc ctccgactgc tgcagcagcc     120
gcccagcccc gccggcggca gggggaggag gtgcaggagc gagccgagcc tcccggccac     180
ccgcaccccc tggcgcagcg gcgcaggagc aaggggctgg tgcagaacat cgaccaactc     240
tactccggcg gcggcaaggt gggctacctc gtctacgcgg gcggccggag gttcctcttg     300
gacctggagc gagatggttc ggtgggcatt gctggcttcg tgcccgcagg aggcgggacg     360
agtgcgccct ggcgccaccg gagccactgc ttctatcggg gcacagtgga cgctagtccc     420
cgctctctgg ctgtctttga cctctgtggg ggtctcgacg gcttcttcgc ggtcaagcac     480
gcgcgctaca ccctaaagcc actgctgcgc ggaccctggg cggaggaaga aaaggggcgc     540
gtgtacgggg atgggtccgc acggatcctg cacgtctaca cccgcgaggg cttcagcttc     600
gaggccctgc cgccgcgcgc cagctgcgaa accccgcgt ccacaccgga ggcccacgag      660
catgctccgg cgcacagcaa cccgagcgga cgcgcagcac tggcctcgca gctcttggac     720
cagtccgctc tctcgcccgc tggggctca ggaccgcaga cgtggtggcg gcggcggcgc       780
cgctccatct cccgggcccg ccaggtggag ctgcttctgg tggctgacgc gtccatggcg     840
cggttgtatg gccggggcct gcagcattac ctgctgaccc tggcctccat cgccaatagg     900
ctgtacagcc atgctagcat cgagaaccac atccgcctgg ccgtggtgaa ggtggtggtg     960
ctaggcgaca aggacaagag cctggaagtg agcaagaacg ctgccaccac actcaagaac    1020
ttttgcaagt ggcagcacca acacaaccag ctgggagatg accatgagga gcactacgat    1080
gcagctatcc tgtttactcg ggaggattta tgtgggcatc attcatgtga caccctggga    1140
atggcagacg ttgggaccat atgttctcca gagcgcagct gtgctgtgat tgaagacgat    1200
ggcctccacg cagccttcac tgtggctcac gaaatcggac atttacttgg cctctcccat    1260
gacgattcca aattctgtga agagaccttt ggttccacag aagataagcg cttaatgtct    1320
tccatcctta ccagcattga tgcatctaag ccctggtcca aatgcacttc agccaccatc    1380
acagaattcc tggatgatgg ccatggtaac tgtttgctgg acctaccacg aaagcagatc    1440
ctgggccccg aagaactccc aggacagacc tacgatgcca cccagcagtg caacctgaca    1500
ttcgggcctc agtactccgt tgtgtcccgg catggatgtct gtgctcgcct gtggtgtgct    1560
gtggtacgcc agggccagat ggtctgtctg accaagaagc tgcctgcggt ggaagggacg    1620
ccttgtggaa aggggagaat ctgcctgcag ggcaaatgtg tggacaaaac caagaaaaaa    1680
tattattcaa cgtcaagcca tggcaactgg ggatcttggg gatcctgggg ccagtgttct    1740
cgctcatgtg gaggaggagt gcagtttgcc tatcgtcact gtaataaccc tgctcccaga    1800
aacaacggac gctactgcac agggaagagg gccatctacc gctcctgcag tctcatgccc    1860
tgcccaccca atggtaaatc atttcgtcat gaacagtgtg aggccaaaaa tggctatcag    1920
tctgatgcaa aaggagtcaa aacttttgtg gaatgggttc ccaaatatgc aggtgtcctg    1980
ccagcggatg tgtgcaagct gacctgcaga gccaagggca ctggctacta tgtggtattt    2040
tctccaaagg tgaccgatgg cactgaatgt aggccgtaca gtaattccgt ctgcgtccgg    2100
gggaagtgtg tgagaactgg ctgtgacggc atcattggct caaagctgca gtatgacaag    2160
tgcggagtat gtggaggaga caactccagc tgtacaaaga ttgttggaac ctttaataag    2220
aaaagtaagg gttacactga cgtggtgagg attcct                             2256
```

<210> SEQ ID NO 6

<211> LENGTH: 752
<212> TYPE: PRT
<213> ORGANISM: Homo sapiens

<400> SEQUENCE: 6

```
Met Leu Leu Gly Trp Ala Ser Leu Leu Cys Ala Phe Arg Leu Pro
  1               5                  10                  15

Leu Ala Ala Val Gly Pro Ala Ala Thr Pro Ala Gln Asp Lys Ala Gly
             20                  25                  30

Gln Pro Pro Thr Ala Ala Ala Ala Gln Pro Arg Arg Gln Gly
         35                  40                  45

Glu Glu Val Gln Glu Arg Ala Glu Pro Pro Gly Pro His Pro Leu
 50                  55                  60

Ala Gln Arg Arg Ser Lys Gly Leu Val Gln Asn Ile Asp Gln Leu
 65                  70                  75                  80

Tyr Ser Gly Gly Lys Val Gly Tyr Leu Val Tyr Ala Gly Gly Arg
                 85                  90                  95

Arg Phe Leu Leu Asp Leu Glu Arg Asp Gly Ser Val Gly Ile Ala Gly
            100                 105                 110

Phe Val Pro Ala Gly Gly Thr Ser Ala Pro Trp Arg His Arg Ser
        115                 120                 125

His Cys Phe Tyr Arg Gly Thr Val Asp Ala Ser Pro Arg Ser Leu Ala
    130                 135                 140

Val Phe Asp Leu Cys Gly Gly Leu Asp Gly Phe Phe Ala Val Lys His
145                 150                 155                 160

Ala Arg Tyr Thr Leu Lys Pro Leu Leu Arg Gly Pro Trp Ala Glu Glu
                165                 170                 175

Glu Lys Gly Arg Val Tyr Gly Asp Gly Ser Ala Arg Ile Leu His Val
            180                 185                 190

Tyr Thr Arg Glu Gly Phe Ser Phe Glu Ala Leu Pro Pro Arg Ala Ser
        195                 200                 205

Cys Glu Thr Pro Ala Ser Thr Pro Glu Ala His Glu His Ala Pro Ala
    210                 215                 220

His Ser Asn Pro Ser Gly Arg Ala Ala Leu Ala Ser Gln Leu Leu Asp
225                 230                 235                 240

Gln Ser Ala Leu Ser Pro Ala Gly Gly Ser Gly Pro Gln Thr Trp Trp
                245                 250                 255

Arg Arg Arg Arg Arg Ser Ile Ser Arg Ala Arg Gln Val Glu Leu Leu
            260                 265                 270

Leu Val Ala Asp Ala Ser Met Ala Arg Leu Tyr Gly Arg Gly Leu Gln
        275                 280                 285

His Tyr Leu Leu Thr Leu Ala Ser Ile Ala Asn Arg Leu Tyr Ser His
    290                 295                 300

Ala Ser Ile Glu Asn His Ile Arg Leu Ala Val Val Lys Val Val Val
305                 310                 315                 320

Leu Gly Asp Lys Asp Lys Ser Leu Glu Val Ser Lys Asn Ala Ala Thr
                325                 330                 335

Thr Leu Lys Asn Phe Cys Lys Trp Gln His Gln His Asn Gln Leu Gly
            340                 345                 350

Asp Asp His Glu Glu His Tyr Asp Ala Ala Ile Leu Phe Thr Arg Glu
        355                 360                 365

Asp Leu Cys Gly His His Ser Cys Asp Thr Leu Gly Met Ala Asp Val
    370                 375                 380

Gly Thr Ile Cys Ser Pro Glu Arg Ser Cys Ala Val Ile Glu Asp Asp
```

|     |     |     |     | 385 |     |     |     | 390 |     |     |     | 395 |     |     |     | 400 |
| --- | --- | --- | --- | --- | --- | --- | --- | --- | --- | --- | --- | --- | --- | --- | --- | --- |
| Gly | Leu | His | Ala | Ala | Phe | Thr | Val | Ala | His | Glu | Ile | Gly | His | Leu | Leu |     |
|     |     |     |     |     |     |     | 405 |     |     |     |     | 410 |     |     |     | 415 |

Gly Leu Ser His Asp Asp Ser Lys Phe Cys Glu Glu Thr Phe Gly Ser
               420                   425            430

Thr Glu Asp Lys Arg Leu Met Ser Ser Ile Leu Thr Ser Ile Asp Ala
           435                   440                 445

Ser Lys Pro Trp Ser Lys Cys Thr Ser Ala Thr Ile Thr Glu Phe Leu
    450                 455                   460

Asp Asp Gly His Gly Asn Cys Leu Leu Asp Leu Pro Arg Lys Gln Ile
465                 470                 475                480

Leu Gly Pro Glu Glu Leu Pro Gly Gln Thr Tyr Asp Ala Thr Gln Gln
               485                   490            495

Cys Asn Leu Thr Phe Gly Pro Glu Tyr Ser Val Cys Pro Gly Met Asp
           500                   505                 510

Val Cys Ala Arg Leu Trp Cys Ala Val Val Arg Gln Gly Gln Met Val
               515                   520            525

Cys Leu Thr Lys Lys Leu Pro Ala Val Glu Gly Thr Pro Cys Gly Lys
           530                   535                 540

Gly Arg Ile Cys Leu Gln Gly Lys Cys Val Asp Lys Thr Lys Lys Lys
545                 550                 555                560

Tyr Tyr Ser Thr Ser Ser His Gly Asn Trp Gly Ser Trp Gly Ser Trp
               565                   570                575

Gly Gln Cys Ser Arg Ser Cys Gly Gly Val Gln Phe Ala Tyr Arg
           580                   585                590

His Cys Asn Asn Pro Ala Pro Arg Asn Asn Gly Arg Tyr Cys Thr Gly
               595                   600            605

Lys Arg Ala Ile Tyr Arg Ser Cys Ser Leu Met Pro Cys Pro Pro Asn
           610                   615                 620

Gly Lys Ser Phe Arg His Glu Gln Cys Glu Ala Lys Asn Gly Tyr Gln
625                 630                 635                640

Ser Asp Ala Lys Gly Val Lys Thr Phe Val Glu Trp Val Pro Lys Tyr
               645                   650                655

Ala Gly Val Leu Pro Ala Asp Val Cys Lys Leu Thr Cys Arg Ala Lys
           660                   665                 670

Gly Thr Gly Tyr Tyr Val Val Phe Ser Pro Lys Val Thr Asp Gly Thr
               675                   680            685

Glu Cys Arg Pro Tyr Ser Asn Ser Val Cys Val Arg Gly Lys Cys Val
           690                   695                 700

Arg Thr Gly Cys Asp Gly Ile Ile Gly Ser Lys Leu Gln Tyr Asp Lys
705                 710                 715                720

Cys Gly Val Cys Gly Gly Asp Asn Ser Ser Cys Thr Lys Ile Val Gly
               725                   730                735

Thr Phe Asn Lys Lys Ser Lys Gly Tyr Thr Asp Val Val Arg Ile Pro
           740                   745                750

<210> SEQ ID NO 7
<211> LENGTH: 2006
<212> TYPE: DNA
<213> ORGANISM: Homo sapiens

<400> SEQUENCE: 7

```
cttgactcaa tcctgcaagc aagtgtgtgt gtgtccccat ccccgcccc gttaacttca      60 tagcaaataa caaataccca taaagtccca gtcgcgcagc ccctcccgc gggcagcgca     120
```

-continued

| | |
|---|---|
| ctatgctgct cgggtgggcg tccctgctgc tgtgcgcgtt ccgcctgccc ctggccgcgg | 180 |
| tcggccccgc cgcgacacct gcccaggata aagccgggca gcctccgact gctgcagcag | 240 |
| ccgcccagcc ccgccggcgg caggggagg aggtgcagga gcgagccgag cctcccggcc | 300 |
| acccgcaccc cctggcgcag cggcgcagga gcaagggct ggtgcagaac atcgaccaac | 360 |
| tctactccgg cggcggcaag gtgggctacc tcgtctacgc gggcggccgg aggttcctct | 420 |
| tggacctgga gcgagatggt tcggtgggca ttgctggctt cgtgcccgca ggaggcggga | 480 |
| cgagtgcgcc ctggcgccac cggagccact gcttctatcg gggcacagtg gacgctagtc | 540 |
| cccgctctct ggctgtcttt gacctctgtg ggggtctcga cggcttcttc gcggtcaagc | 600 |
| acgcgcgcta cccctaaag ccactgctgc gcggaccctg gcggaggaa gaaaaggggc | 660 |
| gcgtgtacgg ggatgggtcc gcacggatcc tgcacgtcta cacccgcgag ggcttcagct | 720 |
| tcgaggccct gccgccgcgc gccagctgcg aaaccccgc gtccacaccg gaggcccacg | 780 |
| agcatgctcc ggcgcacagc aacccgagcg gacgcgcagc actggcctcg cagctcttgg | 840 |
| accagtccgc tctctcgccc gctgggggct caggaccgca gacgtggtgg cggcggcggc | 900 |
| gccgctccat ctcccgggcc cgccaggtgg agctgcttct ggtggctgac gcgtccatgg | 960 |
| cgcggttgta tggccgggc ctgcagcatt acctgctgac cctggcctcc atcgccaata | 1020 |
| ggctgtacag ccatgctagc atcgagaacc acatccgcct ggccgtggtg aaggtggtgg | 1080 |
| tgctaggcga caaggacaag agcctggaag tgagcaagaa cgctgccacc acactcaaga | 1140 |
| acttttgcaa gtggcagcac caacacaacc agctgggaga tgaccatgag gagcactacg | 1200 |
| atgcagctat cctgttttact cgggaggatt tatgtgggca tcattcatgt gacaccctgg | 1260 |
| gaatggcaga cgttgggacc atatgttctc cagagcgcag ctgtgctgtg attgaagacg | 1320 |
| atggcctcca cgcagccttc actgtggctc acgaaatcgg acatttactt ggcctctccc | 1380 |
| atgacgattc caaattctgt gaagagacct ttggttccac agaagataag cgcttaatgt | 1440 |
| cttccatcct taccagcatt gatgcatcta agccctggtc caaatgcact tcagccacca | 1500 |
| tcacagaatt cctggatgat ggccatggta actgtttgct ggacctacca cgaaagcaga | 1560 |
| tcctgggccc gaagaactc ccaggacaga cctacgatgc cacccagcag tgcaacctga | 1620 |
| cattcgggcc tgagtactcc gtgtgtccg gcatggatgt ctgtgctcgc ctgtggtgtg | 1680 |
| ctgtggtacg ccagggccag atggtctgtc tgaccaagaa gctgcctgcg gtggaaggga | 1740 |
| cgccttgtgg aaagggggaga atctgcctgc agggcaaatg tgtggacaaa accaagaaaa | 1800 |
| aatattattc aacgtcaagc catggcaact ggggatcttg gggatcctgg ggccagtgtt | 1860 |
| ctcgctcatg tggaggagga gtgcagtttg cctatcgtca ctgtaataac cctgctccca | 1920 |
| gaaacaacgg acgctactgc acagggaaga gggccatcta ccgctcctgc agtctcatgc | 1980 |
| cctgcccacc caatggtaaa tcattt | 2006 |

<210> SEQ ID NO 8
<211> LENGTH: 628
<212> TYPE: PRT
<213> ORGANISM: Homo sapiens

<400> SEQUENCE: 8

Met Leu Leu Gly Trp Ala Ser Leu Leu Leu Cys Ala Phe Arg Leu Pro
1               5                   10                  15

Leu Ala Ala Val Gly Pro Ala Ala Thr Pro Ala Gln Asp Lys Ala Gly
            20                  25                  30

```
Gln Pro Pro Thr Ala Ala Ala Ala Gln Pro Arg Arg Gln Gly
         35                  40              45

Glu Glu Val Gln Glu Arg Ala Glu Pro Pro Gly His Pro His Pro Leu
     50              55              60

Ala Gln Arg Arg Arg Ser Lys Gly Leu Val Gln Asn Ile Asp Gln Leu
 65              70              75                       80

Tyr Ser Gly Gly Gly Lys Val Gly Tyr Leu Val Tyr Ala Gly Gly Arg
             85              90                       95

Arg Phe Leu Leu Asp Leu Glu Arg Asp Gly Ser Val Gly Ile Ala Gly
             100             105             110

Phe Val Pro Ala Gly Gly Thr Ser Ala Pro Trp Arg His Arg Ser
         115             120             125

His Cys Phe Tyr Arg Gly Thr Val Asp Ala Ser Pro Arg Ser Leu Ala
     130             135             140

Val Phe Asp Leu Cys Gly Gly Leu Asp Gly Phe Phe Ala Val Lys His
145             150             155                       160

Ala Arg Tyr Thr Leu Lys Pro Leu Leu Arg Gly Pro Trp Ala Glu Glu
             165             170             175

Glu Lys Gly Arg Val Tyr Gly Asp Gly Ser Ala Arg Ile Leu His Val
             180             185             190

Tyr Thr Arg Glu Gly Phe Ser Phe Glu Ala Leu Pro Pro Arg Ala Ser
         195             200             205

Cys Glu Thr Pro Ala Ser Thr Pro Glu Ala His Glu His Ala Pro Ala
         210             215             220

His Ser Asn Pro Ser Gly Arg Ala Ala Leu Ala Ser Gln Leu Leu Asp
225             230             235                       240

Gln Ser Ala Leu Ser Pro Ala Gly Gly Ser Gly Pro Gln Thr Trp Trp
             245             250             255

Arg Arg Arg Arg Arg Ser Ile Ser Arg Ala Arg Gln Val Glu Leu Leu
         260             265             270

Leu Val Ala Asp Ala Ser Met Ala Arg Leu Tyr Gly Arg Gly Leu Gln
         275             280             285

His Tyr Leu Leu Thr Leu Ala Ser Ile Ala Asn Arg Leu Tyr Ser His
     290             295             300

Ala Ser Ile Glu Asn His Ile Arg Leu Ala Val Val Lys Val Val Val
305             310             315                       320

Leu Gly Asp Lys Asp Lys Ser Leu Glu Val Ser Lys Asn Ala Ala Thr
             325             330             335

Thr Leu Lys Asn Phe Cys Lys Trp Gln His Gln His Asn Gln Leu Gly
             340             345             350

Asp Asp His Glu Glu His Tyr Asp Ala Ala Ile Leu Phe Thr Arg Glu
         355             360             365

Asp Leu Cys Gly His His Ser Cys Asp Thr Leu Gly Met Ala Asp Val
     370             375             380

Gly Thr Ile Cys Ser Pro Glu Arg Ser Cys Ala Val Ile Glu Asp Asp
385             390             395                       400

Gly Leu His Ala Ala Phe Thr Val Ala His Glu Ile Gly His Leu Leu
             405             410             415

Gly Leu Ser His Asp Asp Ser Lys Phe Cys Glu Glu Thr Phe Gly Ser
             420             425             430

Thr Glu Asp Lys Arg Leu Met Ser Ser Ile Leu Thr Ser Ile Asp Ala
         435             440             445

Ser Lys Pro Trp Ser Lys Cys Thr Ser Ala Thr Ile Thr Glu Phe Leu
```

```
                  450                 455                 460
Asp Asp Gly His Gly Asn Cys Leu Leu Asp Leu Pro Arg Lys Gln Ile
465                 470                 475                 480

Leu Gly Pro Glu Glu Leu Pro Gly Gln Thr Tyr Asp Ala Thr Gln Gln
                485                 490                 495

Cys Asn Leu Thr Phe Gly Pro Glu Tyr Ser Val Cys Pro Gly Met Asp
                500                 505                 510

Val Cys Ala Arg Leu Trp Cys Ala Val Val Arg Gly Gln Met Val
            515                 520                 525

Cys Leu Thr Lys Lys Leu Pro Ala Val Glu Gly Thr Pro Cys Gly Lys
        530                 535                 540

Gly Arg Ile Cys Leu Gln Gly Lys Cys Val Asp Lys Thr Lys Lys
545                 550                 555                 560

Tyr Tyr Ser Thr Ser Ser His Gly Asn Trp Gly Ser Trp Gly Ser Trp
                565                 570                 575

Gly Gln Cys Ser Arg Ser Cys Gly Gly Val Gln Phe Ala Tyr Arg
                580                 585                 590

His Cys Asn Asn Pro Ala Pro Arg Asn Asn Gly Arg Tyr Cys Thr Gly
            595                 600                 605

Lys Arg Ala Ile Tyr Arg Ser Cys Ser Leu Met Pro Cys Pro Pro Asn
        610                 615                 620

Gly Lys Ser Phe
625

<210> SEQ ID NO 9
<211> LENGTH: 1701
<212> TYPE: DNA
<213> ORGANISM: Homo sapiens

<400> SEQUENCE: 9
atgctgctcg ggtgggcgtc cctgctgctg tgcgcgttcc gcctgcccct ggccgcggtc      60
ggccccgccg cgacacctgc ccaggataaa gccgggcagc ctccgactgc tgcagcagcc     120
gcccagcccc gccggcggca gggggaggag gtgcaggagc gagccgagcc tcccggccac     180
ccgcaccccc tggcgcagcg gcgcaggagc aaggggctgg tgcagaacat cgaccaactc     240
tactccggcg gcggcaaggt gggctacctc gtctacgcgg gcggccggag gttcctcttg     300
gacctggagc gagatggttc ggtgggcatt gctggcttcg tgcccgcagg aggcgggacg     360
agtgcgccct ggcgccaccg gagccactgc ttctatcggg gcacagtgga cgctagtccc     420
cgctctctgg ctgtctttga cctctgtggg ggtctcgacg gcttcttcgc ggtcaagcac     480
gcgcgctaca ccctaaagcc actgctgcgc ggaccctggg cggaggaaga aaaggggcgc     540
gtgtacgggg atgggtccgc acggatcctg cacgtctaca cccgcgaggg cttcagcttc     600
gaggccctgc cgccgcgcgc cagctgcgaa accccgcgt ccacaccgga ggcccacgag     660
catgctccgg cgcacagcaa cccgagcgga cgcgcagcac tggcctcgca gctcttggac     720
cagtccgctc tctcgcccgc tgggggctca ggaccgcaga cgtggtggcg gcggcggcgc     780
cgctccatct cccgggcccg ccaggtggag ctgcttctgg tggctgacgc gtccatggcg     840
cggttgtatg gccggggcct gcagcattac ctgctgaccc tggcctccat cgccaatagg     900
ctgtacagcc atgctagcat cgagaaccac atccgcctgg ccgtggtgaa ggtggtggtg     960
ctaggcgaca aggacaagag cctggaagtg agcaagaacg ctgccaccac actcaagaac    1020
ttttgcaagt ggcagcacca acacaaccag ctgggagatg accatgagga gcactacgat    1080
```

-continued

```
gcagctatcc tgtttactcg ggaggattta tgtgggcatc attcatgtga caccctggga   1140
atggcagacg ttgggaccat atgttctcca gagcgcagct gtgctgtgat tgaagacgat   1200
ggcctccacg cagccttcac tgtggctcac gaaatcggac atttacttgg cctctcccat   1260
gacgattcca aattctgtga agagaccttt ggttccacag aagataagcg cttaatgtct   1320
tccatcctta ccagcattga tgcatctaag ccctggtcca atgcacttc agccaccatc    1380 acagaattcc tggatgatgg ccatggtaac tgtttgctgg acctaccacg aaagcagatc   1440
ctgggccccg aagaactccc aggacagacc tacgatgcca cccagcagtg caacctgaca   1500
ttcgggcctg agtactccgt tgtcccggc atggatgtct gtgctcgcct gtggtgtgct    1560
gtggtacgcc agggccagat ggtctgtctg accaagaagc tgcctgcggt ggaagggacg   1620
ccttgtggaa aggggagaat ctgcctgcag ggcaaatgtg tggacaaaac caagaaaaaa   1680
tattattcaa cgtcaagcca t                                             1701
```

<210> SEQ ID NO 10
<211> LENGTH: 567
<212> TYPE: PRT
<213> ORGANISM: Homo sapiens

<400> SEQUENCE: 10

```
Met Leu Leu Gly Trp Ala Ser Leu Leu Leu Cys Ala Phe Arg Leu Pro
 1               5                   10                  15

Leu Ala Ala Val Gly Pro Ala Ala Thr Pro Ala Gln Asp Lys Ala Gly
                20                  25                  30

Gln Pro Pro Thr Ala Ala Ala Ala Gln Pro Arg Arg Arg Gln Gly
            35                  40                  45

Glu Glu Val Gln Glu Arg Ala Glu Pro Pro Gly His Pro His Pro Leu
        50                  55                  60

Ala Gln Arg Arg Ser Lys Gly Leu Val Gln Asn Ile Asp Gln Leu
65                  70                  75                  80

Tyr Ser Gly Gly Gly Lys Val Gly Tyr Leu Val Tyr Ala Gly Gly Arg
                85                  90                  95

Arg Phe Leu Leu Asp Leu Glu Arg Asp Gly Ser Val Gly Ile Ala Gly
                100                 105                 110

Phe Val Pro Ala Gly Gly Thr Ser Ala Pro Trp Arg His Arg Ser
            115                 120                 125

His Cys Phe Tyr Arg Gly Thr Val Asp Ala Ser Pro Arg Ser Leu Ala
        130                 135                 140

Val Phe Asp Leu Cys Gly Gly Leu Asp Gly Phe Phe Ala Val Lys His
145                 150                 155                 160

Ala Arg Tyr Thr Leu Lys Pro Leu Leu Arg Gly Pro Trp Ala Glu Glu
                165                 170                 175

Glu Lys Gly Arg Val Tyr Gly Asp Gly Ser Ala Arg Ile Leu His Val
                180                 185                 190

Tyr Thr Arg Glu Gly Phe Ser Phe Glu Ala Leu Pro Pro Arg Ala Ser
            195                 200                 205

Cys Glu Thr Pro Ala Ser Thr Pro Glu Ala His Glu His Ala Pro Ala
        210                 215                 220

His Ser Asn Pro Ser Gly Arg Ala Ala Leu Ala Ser Gln Leu Leu Asp
225                 230                 235                 240

Gln Ser Ala Leu Ser Pro Ala Gly Gly Ser Gly Pro Gln Thr Trp Trp
                245                 250                 255

Arg Arg Arg Arg Arg Ser Ile Ser Arg Ala Arg Gln Val Glu Leu Leu
```

```
                    260                 265                 270
Leu Val Ala Asp Ala Ser Met Ala Arg Leu Tyr Gly Arg Gly Leu Gln
            275                 280                 285

His Tyr Leu Leu Thr Leu Ala Ser Ile Ala Asn Arg Leu Tyr Ser His
        290                 295                 300

Ala Ser Ile Glu Asn His Ile Arg Leu Ala Val Val Lys Val Val
305                 310                 315                 320

Leu Gly Asp Lys Asp Lys Ser Leu Glu Val Ser Lys Asn Ala Ala Thr
                325                 330                 335

Thr Leu Lys Asn Phe Cys Lys Trp Gln His Gln His Asn Gln Leu Gly
            340                 345                 350

Asp Asp His Glu Glu His Tyr Asp Ala Ala Ile Leu Phe Thr Arg Glu
        355                 360                 365

Asp Leu Cys Gly His His Ser Cys Asp Thr Leu Gly Met Ala Asp Val
    370                 375                 380

Gly Thr Ile Cys Ser Pro Glu Arg Ser Cys Ala Val Ile Glu Asp Asp
385                 390                 395                 400

Gly Leu His Ala Ala Phe Thr Val Ala His Glu Ile Gly His Leu Leu
                405                 410                 415

Gly Leu Ser His Asp Asp Ser Lys Phe Cys Glu Glu Thr Phe Gly Ser
            420                 425                 430

Thr Glu Asp Lys Arg Leu Met Ser Ser Ile Leu Thr Ser Ile Asp Ala
        435                 440                 445

Ser Lys Pro Trp Ser Lys Cys Thr Ser Ala Thr Ile Thr Glu Phe Leu
    450                 455                 460

Asp Asp Gly His Gly Asn Cys Leu Leu Asp Leu Pro Arg Lys Gln Ile
465                 470                 475                 480

Leu Gly Pro Glu Glu Leu Pro Gly Gln Thr Tyr Asp Ala Thr Gln Gln
                485                 490                 495

Cys Asn Leu Thr Phe Gly Pro Glu Tyr Ser Val Cys Pro Gly Met Asp
            500                 505                 510

Val Cys Ala Arg Leu Trp Cys Ala Val Val Arg Gln Gly Gln Met Val
        515                 520                 525

Cys Leu Thr Lys Lys Leu Pro Ala Val Glu Gly Thr Pro Cys Gly Lys
    530                 535                 540

Gly Arg Ile Cys Leu Gln Gly Lys Cys Val Asp Lys Thr Lys Lys Lys
545                 550                 555                 560

Tyr Tyr Ser Thr Ser His
                565

<210> SEQ ID NO 11
<211> LENGTH: 837
<212> TYPE: PRT
<213> ORGANISM: Homo sapiens

<400> SEQUENCE: 11

Met Ser Gln Thr Gly Ser His Pro Gly Arg Gly Leu Ala Gly Arg Trp
1               5                   10                  15

Leu Trp Gly Ala Gln Pro Cys Leu Leu Leu Pro Ile Val Pro Leu Ser
            20                  25                  30

Trp Leu Val Trp Leu Leu Leu Leu Leu Ala Ser Leu Leu Pro Ser
        35                  40                  45

Ala Arg Leu Ala Ser Pro Leu Pro Arg Glu Glu Glu Ile Val Phe Pro
    50                  55                  60
```

-continued

| | | | | | | | | | | | |
|---|---|---|---|---|---|---|---|---|---|---|---|
|Glu|Lys|Leu|Asn|Gly|Ser|Val|Leu|Pro|Gly|Ser|Gly|Thr|Pro|Ala|Arg|
|65| | | |70| | | |75| | | |80|
|Leu|Leu|Cys|Arg|Leu|Gln|Ala|Phe|Gly|Glu|Thr|Leu|Leu|Leu|Glu|Leu|
| | | |85| | | |90| | | |95| |
|Glu|Gln|Asp|Ser|Gly|Val|Gln|Val|Glu|Gly|Leu|Thr|Val|Gln|Tyr|Leu|
| | |100| | | |105| | | |110| | |
|Gly|Gln|Ala|Pro|Glu|Leu|Leu|Gly|Gly|Ala|Glu|Pro|Gly|Thr|Tyr|Leu|
| |115| | | |120| | | |125| | |
|Thr|Gly|Thr|Ile|Asn|Gly|Asp|Pro|Glu|Ser|Val|Ala|Ser|Leu|His|Trp|
|130| | | |135| | | |140| | | | |
|Asp|Gly|Gly|Ala|Leu|Leu|Gly|Val|Leu|Gln|Tyr|Arg|Gly|Ala|Glu|Leu|
|145| | | |150| | | |155| | | |160|
|His|Leu|Gln|Pro|Leu|Glu|Gly|Gly|Thr|Pro|Asn|Ser|Ala|Gly|Gly|Pro|
| | | |165| | | |170| | | |175| |
|Gly|Ala|His|Ile|Leu|Arg|Arg|Lys|Ser|Pro|Ala|Ser|Gly|Gln|Gly|Pro|
| | |180| | | |185| | | |190| | |
|Met|Cys|Asn|Val|Lys|Ala|Pro|Leu|Gly|Ser|Pro|Ser|Arg|Pro|Arg|
| |195| | | |200| | | |205| | | |
|Arg|Ala|Lys|Arg|Phe|Ala|Ser|Leu|Ser|Arg|Phe|Val|Glu|Thr|Leu|Val|
|210| | | |215| | | |220| | | | |
|Val|Ala|Asp|Asp|Lys|Met|Ala|Ala|Phe|His|Gly|Ala|Gly|Leu|Lys|Arg|
|225| | | |230| | | |235| | | |240|
|Tyr|Leu|Leu|Thr|Val|Met|Ala|Ala|Ala|Lys|Ala|Phe|Lys|His|Pro|
| | | |245| | | |250| | | |255| |
|Ser|Ile|Arg|Asn|Pro|Val|Ser|Leu|Val|Val|Thr|Arg|Leu|Val|Ile|Leu|
| | |260| | | |265| | | |270| | |
|Gly|Ser|Gly|Glu|Glu|Gly|Pro|Gln|Val|Gly|Pro|Ser|Ala|Ala|Gln|Thr|
| |275| | | |280| | | |285| | | |
|Leu|Arg|Ser|Phe|Cys|Ala|Trp|Gln|Arg|Gly|Leu|Asn|Thr|Pro|Glu|Asp|
|290| | | |295| | | |300| | | | |
|Ser|Asp|Pro|Asp|His|Phe|Asp|Thr|Ala|Ile|Leu|Phe|Thr|Arg|Gln|Asp|
|305| | | |310| | | |315| | | |320|
|Leu|Cys|Gly|Val|Ser|Thr|Cys|Asp|Thr|Leu|Gly|Met|Ala|Asp|Val|Gly|
| | | |325| | | |330| | | |335| |
|Thr|Val|Cys|Asp|Pro|Ala|Arg|Ser|Cys|Ala|Ile|Val|Glu|Asp|Asp|Gly|
| | |340| | | |345| | | |350| | |
|Leu|Gln|Ser|Ala|Phe|Thr|Ala|Ala|His|Glu|Leu|Gly|His|Val|Phe|Asn|
| |355| | | |360| | | |365| | | |
|Met|Leu|His|Asp|Asn|Ser|Lys|Pro|Cys|Ile|Ser|Leu|Asn|Gly|Pro|Leu|
|370| | | |375| | | |380| | | | |
|Ser|Thr|Ser|Arg|His|Val|Met|Ala|Pro|Val|Met|Ala|His|Val|Asp|Pro|
|385| | | |390| | | |395| | | |400|
|Glu|Glu|Pro|Trp|Ser|Pro|Cys|Ser|Ala|Arg|Phe|Ile|Thr|Asp|Phe|Leu|
| | | |405| | | |410| | | |415| |
|Asp|Asn|Gly|Tyr|Gly|His|Cys|Leu|Leu|Asp|Lys|Pro|Glu|Ala|Pro|Leu|
| | |420| | | |425| | | |430| | |
|His|Leu|Pro|Val|Thr|Phe|Pro|Gly|Lys|Asp|Tyr|Asp|Ala|Asp|Arg|Gln|
| |435| | | |440| | | |445| | | |
|Cys|Gln|Leu|Thr|Phe|Gly|Pro|Asp|Ser|Arg|His|Cys|Pro|Gln|Leu|Pro|
|450| | | |455| | | |460| | | | |
|Pro|Pro|Cys|Ala|Ala|Leu|Trp|Cys|Ser|Gly|His|Leu|Asn|Gly|His|Ala|
|465| | | |470| | | |475| | | |480|
|Met|Cys|Gln|Thr|Lys|His|Ser|Pro|Trp|Ala|Asp|Gly|Thr|Pro|Cys|Gly|

```
                485                 490                 495
Pro Ala Gln Ala Cys Met Gly Gly Arg Cys Leu His Met Asp Gln Leu
            500                 505                 510

Gln Asp Phe Asn Ile Pro Gln Ala Gly Gly Trp Gly Pro Trp Gly Pro
        515                 520                 525

Trp Gly Asp Cys Ser Arg Thr Cys Gly Gly Val Gln Phe Ser Ser
        530                 535             540

Arg Asp Cys Thr Arg Pro Val Pro Arg Asn Gly Lys Tyr Cys Glu
545                 550                 555                 560

Gly Arg Arg Thr Arg Phe Arg Ser Cys Asn Thr Glu Asp Cys Pro Thr
                565                 570                 575

Gly Ser Ala Leu Thr Phe Arg Glu Glu Gln Cys Ala Ala Tyr Asn His
            580                 585                 590

Arg Thr Asp Leu Phe Lys Ser Phe Pro Gly Pro Met Asp Trp Val Pro
        595                 600                 605

Arg Tyr Thr Gly Val Ala Pro Gln Asp Gln Cys Lys Leu Thr Cys Gln
    610                 615                 620

Ala Arg Ala Leu Gly Tyr Tyr Tyr Val Leu Glu Pro Arg Val Val Asp
625                 630                 635                 640

Gly Thr Pro Cys Ser Pro Asp Ser Ser Val Cys Val Gln Gly Arg
                645                 650                 655

Cys Ile His Ala Gly Cys Asp Arg Ile Ile Gly Ser Lys Lys Phe
            660                 665                 670

Asp Lys Cys Met Val Cys Gly Asp Gly Ser Gly Cys Ser Lys Gln
        675                 680                 685

Ser Gly Ser Phe Arg Lys Phe Arg Tyr Gly Tyr Asn Asn Val Val Thr
    690                 695                 700

Ile Pro Ala Gly Ala Thr His Ile Leu Val Arg Gln Gln Gly Asn Pro
705                 710                 715                 720

Gly His Arg Ser Ile Tyr Leu Ala Leu Lys Leu Pro Asp Gly Ser Tyr
                725                 730                 735

Ala Leu Asn Gly Glu Tyr Thr Leu Met Pro Ser Pro Thr Asp Val Val
            740                 745                 750

Leu Pro Gly Ala Val Ser Leu Arg Tyr Ser Gly Ala Thr Ala Ala Ser
        755                 760                 765

Glu Thr Leu Ser Gly His Gly Pro Leu Ala Gln Pro Leu Thr Leu Gln
    770                 775                 780

Val Leu Val Ala Gly Asn Pro Gln Asp Thr Arg Leu Arg Tyr Ser Phe
785                 790                 795                 800

Phe Val Pro Arg Pro Thr Pro Ser Thr Pro Arg Pro Thr Pro Gln Asp
                805                 810                 815

Trp Leu His Arg Arg Ala Gln Ile Leu Glu Ile Leu Arg Arg Pro
            820                 825                 830

Trp Ala Gly Arg Lys
        835

<210> SEQ ID NO 12
<211> LENGTH: 575
<212> TYPE: PRT
<213> ORGANISM: Homo sapiens

<400> SEQUENCE: 12

Met Ser Gln Thr Gly Ser His Pro Gly Arg Gly Leu Ala Gly Arg Trp
  1               5                  10                  15
```

```
Leu Trp Gly Ala Gln Pro Cys Leu Leu Leu Pro Ile Val Pro Leu Ser
            20                  25                  30

Trp Leu Val Trp Leu Leu Leu Leu Leu Ala Ser Leu Leu Pro Ser
        35                  40                  45

Ala Arg Leu Ala Ser Pro Leu Pro Arg Glu Glu Ile Val Phe Pro
    50                  55                  60

Glu Lys Leu Asn Gly Ser Val Leu Pro Gly Ser Gly Thr Pro Ala Arg
 65                  70                  75                  80

Leu Leu Cys Arg Leu Gln Ala Phe Gly Glu Thr Leu Leu Glu Leu
                85                  90                  95

Glu Gln Asp Ser Gly Val Gln Val Glu Gly Leu Thr Val Gln Tyr Leu
            100                 105                 110

Gly Gln Ala Pro Glu Leu Leu Gly Gly Ala Glu Pro Gly Thr Tyr Leu
            115                 120                 125

Thr Gly Thr Ile Asn Gly Asp Pro Glu Ser Val Ala Ser Leu His Trp
    130                 135                 140

Asp Gly Gly Ala Leu Leu Gly Val Leu Gln Tyr Arg Gly Ala Glu Leu
145                 150                 155                 160

His Leu Gln Pro Leu Glu Gly Gly Thr Pro Asn Ser Ala Gly Gly Pro
                165                 170                 175

Gly Ala His Ile Leu Arg Arg Lys Ser Pro Ala Ser Gly Gln Gly Pro
            180                 185                 190

Met Cys Asn Val Lys Ala Pro Leu Gly Ser Pro Ser Pro Arg Pro Arg
        195                 200                 205

Arg Ala Lys Arg Phe Ala Ser Leu Ser Arg Phe Val Glu Thr Leu Val
    210                 215                 220

Val Ala Asp Asp Lys Met Ala Ala Phe His Gly Ala Gly Leu Lys Arg
225                 230                 235                 240

Tyr Leu Leu Thr Val Met Ala Ala Ala Lys Ala Phe Lys His Pro
                245                 250                 255

Ser Ile Arg Asn Pro Val Ser Leu Val Val Thr Arg Leu Val Ile Leu
            260                 265                 270

Gly Ser Gly Glu Glu Gly Pro Gln Val Gly Pro Ser Ala Ala Gln Thr
        275                 280                 285

Leu Arg Ser Phe Cys Ala Trp Gln Arg Gly Leu Asn Thr Pro Glu Asp
    290                 295                 300

Ser Asp Pro Asp His Phe Asp Thr Ala Ile Leu Phe Thr Arg Gln Asp
305                 310                 315                 320

Leu Cys Gly Val Ser Thr Cys Asp Thr Leu Gly Met Ala Asp Val Gly
                325                 330                 335

Thr Val Cys Asp Pro Ala Arg Ser Cys Ala Ile Val Glu Asp Asp Gly
            340                 345                 350

Leu Gln Ser Ala Phe Thr Ala Ala His Glu Leu Gly His Val Phe Asn
        355                 360                 365

Met Leu His Asp Asn Ser Lys Pro Cys Ile Ser Leu Asn Gly Pro Leu
    370                 375                 380

Ser Thr Ser Arg His Val Met Ala Pro Val Met Ala His Val Asp Pro
385                 390                 395                 400

Glu Glu Pro Trp Ser Pro Cys Ser Ala Arg Phe Ile Thr Asp Phe Leu
                405                 410                 415

Asp Asn Gly Tyr Gly His Cys Leu Leu Asp Lys Pro Glu Ala Pro Leu
            420                 425                 430

His Leu Pro Val Thr Phe Pro Gly Lys Asp Tyr Asp Ala Asp Arg Gln
```

```
                435                 440                 445
Cys Gln Leu Thr Phe Gly Pro Asp Ser Arg His Cys Pro Gln Leu Pro
    450                 455                 460

Pro Pro Cys Ala Ala Leu Trp Cys Ser Gly His Leu Asn Gly His Ala
465                 470                 475                 480

Met Cys Gln Thr Lys His Ser Pro Trp Ala Asp Gly Thr Pro Cys Gly
                485                 490                 495

Pro Ala Gln Ala Cys Met Gly Gly Arg Cys Leu His Met Asp Gln Leu
            500                 505                 510

Gln Asp Phe Asn Ile Pro Gln Ala Gly Gly Trp Gly Pro Trp Gly Pro
        515                 520                 525

Trp Gly Asp Cys Ser Arg Thr Cys Gly Gly Val Gln Phe Ser Ser
    530                 535                 540

Arg Asp Cys Thr Arg Pro Val Pro Arg Asn Gly Gly Lys Tyr Cys Glu
545                 550                 555                 560

Gly Arg Arg Thr Arg Phe Arg Ser Cys Asn Thr Glu Asp Cys Pro
                565                 570                 575

<210> SEQ ID NO 13
<211> LENGTH: 520
<212> TYPE: PRT
<213> ORGANISM: Homo sapiens

<400> SEQUENCE: 13

Met Ser Gln Thr Gly Ser His Pro Gly Arg Gly Leu Ala Gly Arg Trp
1               5                   10                  15

Leu Trp Gly Ala Gln Pro Cys Leu Leu Leu Pro Ile Val Pro Leu Ser
            20                  25                  30

Trp Leu Val Trp Leu Leu Leu Leu Ala Ser Leu Leu Pro Ser
        35                  40                  45

Ala Arg Leu Ala Ser Pro Leu Pro Arg Glu Glu Glu Ile Val Phe Pro
    50                  55                  60

Glu Lys Leu Asn Gly Ser Val Leu Pro Gly Ser Gly Thr Pro Ala Arg
65                  70                  75                  80

Leu Leu Cys Arg Leu Gln Ala Phe Gly Glu Thr Leu Leu Glu Leu
                85                  90                  95

Glu Gln Asp Ser Gly Val Gln Val Glu Gly Leu Thr Val Gln Tyr Leu
            100                 105                 110

Gly Gln Ala Pro Glu Leu Leu Gly Gly Ala Glu Pro Gly Thr Tyr Leu
        115                 120                 125

Thr Gly Thr Ile Asn Gly Asp Pro Glu Ser Val Ala Ser Leu His Trp
    130                 135                 140

Asp Gly Gly Ala Leu Leu Gly Val Leu Gln Tyr Arg Gly Ala Glu Leu
145                 150                 155                 160

His Leu Gln Pro Leu Glu Gly Gly Thr Pro Asn Ser Ala Gly Gly Pro
                165                 170                 175

Gly Ala His Ile Leu Arg Arg Lys Ser Pro Ala Ser Gly Gln Gly Pro
            180                 185                 190

Met Cys Asn Val Lys Ala Pro Leu Gly Ser Pro Ser Pro Arg Pro Arg
        195                 200                 205

Arg Ala Lys Arg Phe Ala Ser Leu Ser Arg Phe Val Glu Thr Leu Val
    210                 215                 220

Val Ala Asp Asp Lys Met Ala Ala Phe His Gly Ala Gly Leu Lys Arg
225                 230                 235                 240
```

Tyr Leu Leu Thr Val Met Ala Ala Ala Lys Ala Phe Lys His Pro
                245                 250                 255

Ser Ile Arg Asn Pro Val Ser Leu Val Val Thr Arg Leu Val Ile Leu
            260                 265                 270

Gly Ser Gly Glu Glu Gly Pro Gln Val Gly Pro Ser Ala Ala Gln Thr
        275                 280                 285

Leu Arg Ser Phe Cys Ala Trp Gln Arg Gly Leu Asn Thr Pro Glu Asp
    290                 295                 300

Ser Asp Pro Asp His Phe Asp Thr Ala Ile Leu Phe Thr Arg Gln Asp
305                 310                 315                 320

Leu Cys Gly Val Ser Thr Cys Asp Thr Leu Gly Met Ala Asp Val Gly
                325                 330                 335

Thr Val Cys Asp Pro Ala Arg Ser Cys Ala Ile Val Glu Asp Asp Gly
            340                 345                 350

Leu Gln Ser Ala Phe Thr Ala Ala His Glu Leu Gly His Val Phe Asn
        355                 360                 365

Met Leu His Asp Asn Ser Lys Pro Cys Ile Ser Leu Asn Gly Pro Leu
    370                 375                 380

Ser Thr Ser Arg His Val Met Ala Pro Val Met Ala His Val Asp Pro
385                 390                 395                 400

Glu Glu Pro Trp Ser Pro Cys Ser Ala Arg Phe Ile Thr Asp Phe Leu
                405                 410                 415

Asp Asn Gly Tyr Gly His Cys Leu Leu Asp Lys Pro Glu Ala Pro Leu
            420                 425                 430

His Leu Pro Val Thr Phe Pro Gly Lys Asp Tyr Asp Ala Asp Arg Gln
        435                 440                 445

Cys Gln Leu Thr Phe Gly Pro Asp Ser Arg His Cys Pro Gln Leu Pro
    450                 455                 460

Pro Pro Cys Ala Ala Leu Trp Cys Ser Gly His Leu Asn Gly His Ala
465                 470                 475                 480

Met Cys Gln Thr Lys His Ser Pro Trp Ala Asp Gly Thr Pro Cys Gly
                485                 490                 495

Pro Ala Gln Ala Cys Met Gly Gly Arg Cys Leu His Met Asp Gln Leu
            500                 505                 510

Gln Asp Phe Asn Ile Pro Gln Ala
        515                 520

<210> SEQ ID NO 14
<211> LENGTH: 2318
<212> TYPE: DNA
<213> ORGANISM: Homo sapiens

<400> SEQUENCE: 14
gaattcccac catgctgctc gggtgggcgt ccctgctgct gtgcgcgttc cgcctgcccc      60
tggccgcggt cggccccgcc gcgacacctg cccaggataa agccgggcag cctccgactg     120
ctgcagcagc cgcccagccc cgccggcggc agggggagga ggtgcaggag cgagccgagc     180
ctcccggcca cccgcacccc ctggcgcagc ggcgcaggag caaggggctg gtgcagaaca     240
tcgaccaact ctactccggc ggcggcaagg tgggctacct cgtctacgcg ggcggccgga     300
ggttcctctt ggacctggag cgagatggtt cgtgggcat tgctggcttc gtgcccgcag     360
gaggcgggac gagtgcgccc tggcgccacc ggagccactg cttctatcgg ggcacagtgg     420
acgctagtcc ccgctctctg gctgtctttg acctctgtgg gggtctcgac ggcttcttcg     480
cggtcaagca cgcgcgctac accctaaagc cactgctgcg cggaccctgg gcggaggaag     540

-continued

```
aaaagggcg cgtgtacggg gatgggtccg cacggatcct gcacgtctac acccgcgagg      600
gcttcagctt cgaggccctg ccgccgcgcg ccagctgcga aaccccgcg tccacaccgg       660 aggcccacga gcatgctccg gcgcacagca acccgagcgg acgcgcagca ctggcctcgc     720
agctcttgga ccagtccgct ctctcgcccg ctggggctc aggaccgcag acgtggtggc      780
ggcggcggcg ccgctccatc tcccgggccc gccaggtgga gctgcttctg gtggctgacg    840
cgtccatggc gcggttgtat ggccggggcc tgcagcatta cctgctgacc ctggcctcca    900
tcgccaatag gctgtacagc catgctagca tcgagaacca catccgcctg gccgtggtga    960
aggtggtggt gctaggcgac aaggacaaga gcctggaagt gagcaagaac gctgccacca   1020
cactcaagaa cttttgcaag tggcagcacc aacacaacca gctgggagat gaccatgagg   1080
agcactacga tgcagctatc ctgtttactc gggaggattt atgtgggcat cattcatgtg   1140
acaccctggg aatggcagac gttgggacca tatgttctcc agagcgcagc tgtgctgtga   1200
ttgaagacga tggcctccac gcagccttca ctgtggctca cgaaatcgga catttacttg   1260
gcctctccca tgacgattcc aaattctgtg aagagacctt tggttccaca gaagataagc   1320
gcttaatgtc ttccatcctt accagcattg atgcatctaa gccctggtcc aaatgcactt   1380
cagccaccat cacagaattc ctggatgatg ccatggtaa ctgtttgctg gacctaccac     1440
gaaagcagat cctgggcccc gaagaactcc aggacagac tacgatgcc acccagcagt     1500 gcaacctgac attcgggcct gagtactccg tgtgtcccgg catggatgtc tgtgctcgcc   1560
tgtggtgtgc tgtggtacgc cagggccaga tggtctgtct gaccaagaag ctgcctgcgg   1620
tggaagggac gccttgtgga aggggagaa tctgcctgca gggcaaatgt gtggacaaaa    1680
ccaagaaaaa atattattca acgtcaagcc atggcaactg gggatcttgg ggatcctggg   1740
gccagtgttc tcgctcatgt ggaggaggag tgcagtttgc ctatcgtcac tgtaataacc   1800
ctgctcccag aaacaacgga cgctactgca caggaagag gccatctac cgctcctgca     1860 gtctcatgcc ctgcccaccc aatggtaaat catttcgtca tgaacagtgt gaggccaaaa    1920
atggctatca gtctgatgca aaaggagtca aacttttgt ggaatgggtt cccaaatatg    1980
caggtgtcct gccagcggat gtgtgcaagc tgacctgcag agccaagggc actggctact    2040
atgtggtatt ttctccaaag gtgaccgatg cactgaatg taggccgtac agtaattccg     2100
tctgcgtccg ggggaagtgt gtgagaactg gctgtgacgg catcattggc tcaaagctgc   2160
agtatgacaa gtgcggagta tgtggaggag acaactccag ctgtacaaag attgttggaa   2220
cctttaataa gaaaagtaag ggttacactg acgtggtgag gattcctgga tccggatctg   2280
cttggagcca cccgcagttc gaaaaataag gcggccgc                           2318
```

<210> SEQ ID NO 15
<211> LENGTH: 763
<212> TYPE: PRT
<213> ORGANISM: Homo sapiens

<400> SEQUENCE: 15

Met Leu Leu Gly Trp Ala Ser Leu Leu Leu Cys Ala Phe Arg Leu Pro
1               5                   10                  15

Leu Ala Ala Val Gly Pro Ala Ala Thr Pro Ala Gln Asp Lys Ala Gly
                20                  25                  30

Gln Pro Pro Thr Ala Ala Ala Ala Ala Gln Pro Arg Arg Gln Gly
            35                  40                  45

Glu Glu Val Gln Glu Arg Ala Glu Pro Pro Gly His Pro His Pro Leu

```
                    50                  55                  60
Ala Gln Arg Arg Ser Lys Gly Leu Val Gln Asn Ile Asp Gln Leu
 65                  70                  75                  80

Tyr Ser Gly Gly Lys Val Gly Tyr Leu Val Tyr Ala Gly Gly Arg
                     85                  90                  95

Arg Phe Leu Leu Asp Leu Glu Arg Asp Gly Ser Val Gly Ile Ala Gly
                    100                 105                 110

Phe Val Pro Ala Gly Gly Thr Ser Ala Pro Trp Arg His Arg Ser
                115                 120                 125

His Cys Phe Tyr Arg Gly Thr Val Asp Ala Ser Pro Arg Ser Leu Ala
                130                 135                 140

Val Phe Asp Leu Cys Gly Gly Leu Asp Gly Phe Phe Ala Val Lys His
145                 150                 155                 160

Ala Arg Tyr Thr Leu Lys Pro Leu Leu Arg Gly Pro Trp Ala Glu Glu
                165                 170                 175

Glu Lys Gly Arg Val Tyr Gly Asp Gly Ser Ala Arg Ile Leu His Val
                180                 185                 190

Tyr Thr Arg Glu Gly Phe Ser Phe Glu Ala Leu Pro Pro Arg Ala Ser
                195                 200                 205

Cys Glu Thr Pro Ala Ser Thr Pro Glu Ala His Glu His Ala Pro Ala
210                 215                 220

His Ser Asn Pro Ser Gly Arg Ala Ala Leu Ala Ser Gln Leu Leu Asp
225                 230                 235                 240

Gln Ser Ala Leu Ser Pro Ala Gly Gly Ser Gly Pro Gln Thr Trp Trp
                245                 250                 255

Arg Arg Arg Arg Arg Ser Ile Ser Arg Ala Arg Gln Val Glu Leu Leu
                260                 265                 270

Leu Val Ala Asp Ala Ser Met Ala Arg Leu Tyr Gly Arg Gly Leu Gln
                275                 280                 285

His Tyr Leu Leu Thr Leu Ala Ser Ile Ala Asn Arg Leu Tyr Ser His
                290                 295                 300

Ala Ser Ile Glu Asn His Ile Arg Leu Ala Val Val Lys Val Val Val
305                 310                 315                 320

Leu Gly Asp Lys Asp Lys Ser Leu Glu Val Ser Lys Asn Ala Ala Thr
                325                 330                 335

Thr Leu Lys Asn Phe Cys Lys Trp Gln His Gln His Asn Gln Leu Gly
                340                 345                 350

Asp Asp His Glu Glu His Tyr Asp Ala Ala Ile Leu Phe Thr Arg Glu
                355                 360                 365

Asp Leu Cys Gly His His Ser Cys Asp Thr Leu Gly Met Ala Asp Val
                370                 375                 380

Gly Thr Ile Cys Ser Pro Glu Arg Ser Cys Ala Val Ile Glu Asp Asp
385                 390                 395                 400

Gly Leu His Ala Ala Phe Thr Val Ala His Glu Ile Gly His Leu Leu
                    405                 410                 415

Gly Leu Ser His Asp Asp Ser Lys Phe Cys Glu Glu Thr Phe Gly Ser
                420                 425                 430

Thr Glu Asp Lys Arg Leu Met Ser Ser Ile Leu Thr Ser Ile Asp Ala
                435                 440                 445

Ser Lys Pro Trp Ser Lys Cys Thr Ser Ala Thr Ile Thr Glu Phe Leu
450                 455                 460

Asp Asp Gly His Gly Asn Cys Leu Leu Asp Leu Pro Arg Lys Gln Ile
465                 470                 475                 480
```

-continued

```
Leu Gly Pro Glu Glu Leu Pro Gly Gln Thr Tyr Asp Ala Thr Gln Gln
                485                 490                 495
Cys Asn Leu Thr Phe Gly Pro Glu Tyr Ser Val Cys Pro Gly Met Asp
            500                 505                 510
Val Cys Ala Arg Leu Trp Cys Ala Val Val Arg Gln Gly Gln Met Val
        515                 520                 525
Cys Leu Thr Lys Lys Leu Pro Ala Val Glu Gly Thr Pro Cys Gly Lys
    530                 535                 540
Gly Arg Ile Cys Leu Gln Gly Lys Cys Val Asp Lys Thr Lys Lys Lys
545                 550                 555                 560
Tyr Tyr Ser Thr Ser Ser His Gly Asn Trp Gly Ser Trp Gly Ser Trp
                565                 570                 575
Gly Gln Cys Ser Arg Ser Cys Gly Gly Val Gln Phe Ala Tyr Arg
            580                 585                 590
His Cys Asn Asn Pro Ala Pro Arg Asn Asn Gly Arg Tyr Cys Thr Gly
        595                 600                 605
Lys Arg Ala Ile Tyr Arg Ser Cys Ser Leu Met Pro Cys Pro Pro Asn
    610                 615                 620
Gly Lys Ser Phe Arg His Glu Gln Cys Glu Ala Lys Asn Gly Tyr Gln
625                 630                 635                 640
Ser Asp Ala Lys Gly Val Lys Thr Phe Val Glu Trp Val Pro Lys Tyr
                645                 650                 655
Ala Gly Val Leu Pro Ala Asp Val Cys Lys Leu Thr Cys Arg Ala Lys
            660                 665                 670
Gly Thr Gly Tyr Tyr Val Val Phe Ser Pro Lys Val Thr Asp Gly Thr
        675                 680                 685
Glu Cys Arg Pro Tyr Ser Asn Ser Val Cys Val Arg Gly Lys Cys Val
    690                 695                 700
Arg Thr Gly Cys Asp Gly Ile Ile Gly Ser Lys Leu Gln Tyr Asp Lys
705                 710                 715                 720
Cys Gly Val Cys Gly Gly Asp Asn Ser Ser Cys Thr Lys Ile Val Gly
                725                 730                 735
Thr Phe Asn Lys Lys Ser Lys Gly Tyr Thr Asp Val Val Arg Ile Pro
            740                 745                 750
Gly Ser Ala Trp Ser His Pro Gln Phe Glu Lys
        755                 760
```

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 16
gactgactga attcataccc ataaagtccc agtcgcgca          39

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 17
cagggcttag atgcatcaat gctgg          25

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 18
taccagcatt gatgcatcta agccct                                    26

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 19
aaatgggcgc ggccgctgca tcggtgctga atcctccagt tatct              45

<210> SEQ ID NO 20
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gtacaaagat tgttggaacc tttaataaga aaagtaaggg ttacactgac gtggtgagga  60
ttc                                                              63

<210> SEQ ID NO 21
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ctggatccgg atctgcttgg agccacccgc agttcgaaaa ataaggc              47

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 22

Gly Ser Gly Ser Ala
 1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      Strep-tag II peptide

<400> SEQUENCE: 23

Trp Ser His Pro Gln Phe Glu Lys
 1               5

<210> SEQ ID NO 24
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ggccgcctta tttttcgaac tgcgggtggc tccaagcaga tccggatcca ggaatcctca    60
c                                                                    61

<210> SEQ ID NO 25
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cacgtcagtg taaccttac ttttcttatt aaaggttcca acaatcttt                 49

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      catalytic motif

<400> SEQUENCE: 26

His Glu Leu Gly His
 1               5

<210> SEQ ID NO 27
<211> LENGTH: 15
<212> TYPE: DNA
<213> ORGANISM: Artificial Sequence
<220> FEATURE:
<223> OTHER INFORMATION: Description of Artificial Sequence: Synthetic
      insert nucleotide sequence

<400> SEQUENCE: 27
catgggcagc tcgag                                                     15

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence: Synthetic
      insert nucleotide sequence

<400> SEQUENCE: 28
ctgcaggcga gcctgaattc ctcgagccat catg                                34

<210> SEQ ID NO 29
<211> LENGTH: 68
<212> TYPE: DNA
<213> ORGANISM: Artificial Sequence
<220> FEATURE:
<223> OTHER INFORMATION: Description of Artificial Sequence: Synthetic
      adapter sequence

<400> SEQUENCE: 29
cgaggttaaa aaacgtctag gcccccccgaa ccacggggac gtggttttcc tttgaaaaac    60
acgattgc    68

<210> SEQ ID NO 30
<211> LENGTH: 930
<212> TYPE: PRT
<213> ORGANISM: Homo sapiens

<400> SEQUENCE: 30

```
Met Leu Leu Gly Trp Ala Ser Leu Leu Cys Ala Phe Arg Leu Pro
 1               5                  10                  15

Leu Ala Ala Val Gly Pro Ala Ala Thr Pro Ala Gln Asp Lys Ala Gly
                20                  25                  30

Gln Pro Pro Thr Ala Ala Ala Ala Gln Pro Arg Arg Arg Gln Gly
         35                  40                  45

Glu Glu Val Gln Glu Arg Ala Glu Pro Pro Gly His Pro His Pro Leu
     50                  55                  60

Ala Gln Arg Arg Arg Ser Lys Gly Leu Val Gln Asn Ile Asp Gln Leu
 65                  70                  75                  80

Tyr Ser Gly Gly Gly Lys Val Gly Tyr Leu Val Tyr Ala Gly Gly Arg
                85                  90                  95

Arg Phe Leu Leu Asp Leu Glu Arg Asp Gly Ser Val Gly Ile Ala Gly
                100                 105                 110

Phe Val Pro Ala Gly Gly Gly Thr Ser Ala Pro Trp Arg His Arg Ser
            115                 120                 125

His Cys Phe Tyr Arg Gly Thr Val Asp Ala Ser Pro Arg Ser Leu Ala
        130                 135                 140

Val Phe Asp Leu Cys Gly Gly Leu Asp Gly Phe Phe Ala Val Lys His
145                 150                 155                 160

Ala Arg Tyr Thr Leu Lys Pro Leu Leu Arg Gly Pro Trp Ala Glu Glu
                165                 170                 175

Glu Lys Gly Arg Val Tyr Gly Asp Gly Ser Ala Arg Ile Leu His Val
            180                 185                 190

Tyr Thr Arg Glu Gly Phe Ser Phe Glu Ala Leu Pro Pro Arg Ala Ser
        195                 200                 205

Cys Glu Thr Pro Ala Ser Thr Pro Glu Ala His Glu His Ala Pro Ala
    210                 215                 220

His Ser Asn Pro Ser Gly Arg Ala Ala Leu Ala Ser Gln Leu Leu Asp
225                 230                 235                 240

Gln Ser Ala Leu Ser Pro Ala Gly Gly Ser Gly Pro Gln Thr Trp Trp
                245                 250                 255

Arg Arg Arg Arg Arg Ser Ile Ser Arg Ala Arg Gln Val Glu Leu Leu
            260                 265                 270

Leu Val Ala Asp Ala Ser Met Ala Arg Leu Tyr Gly Arg Gly Leu Gln
        275                 280                 285

His Tyr Leu Leu Thr Leu Ala Ser Ile Ala Asn Arg Leu Tyr Ser His
    290                 295                 300

Ala Ser Ile Glu Asn His Ile Arg Leu Ala Val Val Lys Val Val Val
305                 310                 315                 320

Leu Gly Asp Lys Asp Lys Ser Leu Glu Val Ser Lys Asn Ala Ala Thr
                325                 330                 335

Thr Leu Lys Asn Phe Cys Lys Trp Gln His Gln His Asn Gln Leu Gly
            340                 345                 350
```

-continued

```
Asp Asp His Glu Glu His Tyr Asp Ala Ala Ile Leu Phe Thr Arg Glu
        355                 360                 365
Asp Leu Cys Gly His His Ser Cys Asp Thr Leu Gly Met Ala Asp Val
    370                 375                 380
Gly Thr Ile Cys Ser Pro Glu Arg Ser Cys Ala Val Ile Glu Asp Asp
385                 390                 395                 400
Gly Leu His Ala Ala Phe Thr Val Ala His Gln Ile Gly His Leu Leu
                405                 410                 415
Gly Leu Ser His Asp Asp Ser Lys Phe Cys Glu Glu Thr Phe Gly Ser
            420                 425                 430
Thr Glu Asp Lys Arg Leu Met Ser Ser Ile Leu Thr Ser Ile Asp Ala
        435                 440                 445
Ser Lys Pro Trp Ser Lys Cys Thr Ser Ala Thr Ile Thr Glu Phe Leu
    450                 455                 460
Asp Asp Gly His Gly Asn Cys Leu Leu Asp Leu Pro Arg Lys Gln Ile
465                 470                 475                 480
Leu Gly Pro Glu Glu Leu Pro Gly Gln Thr Tyr Asp Ala Thr Gln Gln
                485                 490                 495
Cys Asn Leu Thr Phe Gly Pro Glu Tyr Ser Val Cys Pro Gly Met Asp
            500                 505                 510
Val Cys Ala Arg Leu Trp Cys Ala Val Val Arg Gln Gly Gln Met Val
        515                 520                 525
Cys Leu Thr Lys Lys Leu Pro Ala Val Glu Gly Thr Pro Cys Gly Lys
    530                 535                 540
Gly Arg Ile Cys Leu Gln Gly Lys Cys Val Asp Lys Thr Lys Lys Lys
545                 550                 555                 560
Tyr Tyr Ser Thr Ser Ser His Gly Asn Trp Gly Ser Trp Gly Ser Trp
                565                 570                 575
Gly Gln Cys Ser Arg Ser Cys Gly Gly Gly Val Gln Phe Ala Tyr Arg
            580                 585                 590
His Cys Asn Asn Pro Ala Pro Arg Asn Asn Gly Arg Tyr Cys Thr Gly
        595                 600                 605
Lys Arg Ala Ile Tyr Arg Ser Cys Ser Leu Met Pro Cys Pro Pro Asn
    610                 615                 620
Gly Lys Ser Phe Arg His Glu Gln Cys Glu Ala Lys Asn Gly Tyr Gln
625                 630                 635                 640
Ser Asp Ala Lys Gly Val Lys Thr Phe Val Glu Trp Val Pro Lys Tyr
                645                 650                 655
Ala Gly Val Leu Pro Ala Asp Val Cys Lys Leu Thr Cys Arg Ala Lys
            660                 665                 670
Gly Thr Gly Tyr Tyr Val Val Phe Ser Pro Lys Val Thr Asp Gly Thr
        675                 680                 685
Glu Cys Arg Pro Tyr Ser Asn Ser Val Cys Val Arg Gly Lys Cys Val
    690                 695                 700
Arg Thr Gly Cys Asp Gly Ile Ile Gly Ser Lys Leu Gln Tyr Asp Lys
705                 710                 715                 720
Cys Gly Val Cys Gly Gly Asp Asn Ser Ser Cys Thr Lys Ile Val Gly
                725                 730                 735
Thr Phe Asn Lys Lys Ser Lys Gly Tyr Thr Asp Val Val Arg Ile Pro
            740                 745                 750
Glu Gly Ala Thr His Ile Lys Val Arg Gln Phe Lys Ala Lys Asp Gln
        755                 760                 765
Thr Arg Phe Thr Ala Tyr Leu Ala Leu Lys Lys Lys Asn Gly Glu Tyr
```

```
                    770                 775                 780
Leu Ile Asn Gly Lys Tyr Met Ile Ser Thr Ser Glu Thr Ile Ile Asp
785                 790                 795                 800

Ile Asn Gly Thr Val Met Asn Tyr Ser Gly Trp Ser His Arg Asp Asp
                805                 810                 815

Phe Leu His Gly Met Gly Tyr Ser Ala Thr Lys Glu Ile Leu Ile Val
                820                 825                 830

Gln Ile Leu Ala Thr Asp Pro Thr Lys Pro Leu Asp Val Arg Tyr Ser
            835                 840                 845

Phe Phe Val Pro Lys Lys Ser Thr Pro Lys Val Asn Ser Val Thr Ser
850                 855                 860

His Gly Ser Asn Lys Val Gly Ser His Thr Ser Gln Pro Gln Trp Val
865                 870                 875                 880

Thr Gly Pro Trp Leu Ala Cys Ser Arg Thr Cys Asp Thr Gly Trp His
                885                 890                 895

Thr Arg Thr Val Gln Cys Gln Asp Gly Asn Arg Lys Leu Ala Lys Gly
                900                 905                 910

Cys Pro Leu Ser Gln Arg Pro Ser Ala Phe Lys Gln Cys Leu Leu Lys
            915                 920                 925

Lys Cys
    930

<210> SEQ ID NO 31
<211> LENGTH: 4307
<212> TYPE: DNA
<213> ORGANISM: Homo sapiens

<400> SEQUENCE: 31
cacagacaca tatgcacgag agagacagag gaggaaagag acagagacaa aggcacagcg      60
gaagaaggca gagacagggc aggcacagaa gcggcccaga cagagtccta cagagggaga     120
ggccagagaa gctgcagaag acacaggcag ggagagacaa agatccagga aaggagggct     180
caggaggaga gtttggagaa gccagacccc tgggcacctc tcccaagccc aaggactaag     240
ttttctccat ttcctttaac ggtcctcagc ccttctgaaa actttgcctc tgaccttggc     300
aggagtccaa gccccaggc tacagagagg agctttccaa agctagggtg tggaggactt      360
ggtgccctag acggcctcag tccctcccag ctgcagtacc agtgccatgt cccagacagg     420
ctcgcatccc gggaggggct tggcagggcg ctggctgtgg ggagcccaac cctgcctcct     480
gctccccatt gtgccgctct cctggctggt gtggctgctt ctgctactgc tggcctctct     540
cctgccctca gcccggctgg ccagcccccct ccccgggag gaggagatcg tgtttccaga      600
gaagctcaac ggcagcgtcc tgcctggctc gggcacccct gccaggctgt tgtgccgctt     660
gcaggccttt ggggagacgc tgctactaga gctggagcag actccggtg tgcaggtcga      720 ggggctgaca gtgcagtacc tgggccaggc gcctgagctg ctgggtggag cagagcctgg     780
cacctacctg actggcacca tcaatggaga tccggagtcg gtggcatctc tgcactggga     840
tgggggagcc ctgttaggcg tgttacaata tcgggggggct gaactccacc tccagccct     900 ggagggaggc acccctaact ctgctggggg acctggggct cacatcctac gccggaagag     960
tcctgccagc ggtcaaggtc ccatgtgcaa cgtcaaggcc cctcttggaa gccccagccc    1020
cagaccccga agagccaagc gctttgcttc actgagtaga tttgtggaga cactggtggt    1080
ggcagatgac aagatggccg cattccacgg tgcggggcta aagcgctacc tgctaacagt    1140
gatggcagca gcagccaagg ccttcaagca cccaagcatc cgcaatcctg tcagcttggt    1200
```

-continued

```
ggtgactcgg ctagtgatcc tggggtcagg cgaggagggg ccccaagtgg ggcccagtgc   1260
tgcccagacc ctgcgcagct tctgtgcctg gcagcggggc ctcaacaccc ctgaggactc   1320

ggaccctgac cactttgaca cagccattct gtttacccgt caggacctgt gtggagtctc   1380
cacttgcgac acgctgggta tggctgatgt gggcaccgtc tgtgacccgg ctcggagctg   1440
tgccattgtg gaggatgatg ggctccagtc agccttcact gctgctcatg aactgggtca   1500
tgtcttcaac atgctccatg acaactccaa gccatgcatc agtttgaatg ggcctttgag   1560
cacctctcgc catgtcatgg cccctgtgat ggctcatgtg gatcctgagg agccctggtc   1620
cccctgcagt gcccgcttca tcactgactt cctggacaat ggctatgggc actgtctctt   1680
agacaaacca gaggctccat tgcatctgcc tgtgactttc cctggcaagg actatgatgc   1740
tgaccgccag tgccagctga ccttcgggcc cgactcacgc cattgtccac agctgccgcc   1800
gccctgtgct gccctctggt gctctggcca cctcaatggc catgccatgt gccagaccaa   1860
acactcgccc tgggccgatg gcacaccctg cgggcccgca caggcctgca tgggtggtcg   1920
ctgcctccac atggaccagc tccaggactt caatattcca caggctggtg gctggggtcc   1980
ttggggacca tggggtgact gctctcggac ctgtgggggt ggtgtccagt tctcctcccg   2040
agactgcacg aggcctgtcc cccggaatgg tggcaagtac tgtgagggcc gccgtacccg   2100
cttccgctcc tgcaacactg aggactgccc aactggctca gccctgacct tccgcgagga   2160
gcagtgtgct gcctacaacc accgcaccga cctcttcaag agcttcccag ggcccatgga   2220
ctgggttcct cgctacacag gcgtggcccc ccaggaccag tgcaaactca cctgccaggc   2280
ccgggcactg ggctactact atgtgctgga gccacgggtg gtagatggga ccccctgttc   2340
cccggacagc tcctcggtct gtgtccaggg ccgatgcatc catgctggct gtgatcgcat   2400
cattggctcc aagaagaagt ttgacaagtg catggtgtgc ggaggggacg gttctggttg   2460
cagcaagcag tcaggctcct tcaggaaatt caggtacgga tacaacaatg tggtcactat   2520
ccccgcgggg gccacccaca ttcttgtccg gcagcaggga aaccctggcc accggagcat   2580
ctacttggcc ctgaagctgc cagatggctc ctatgccctc aatggtgaat acacgctgat   2640
gccctccccc acagatgtgg tactgcctgg ggcagtcagc ttgcgctaca gcggggccac   2700
tgcagcctca gagacactgt caggccatgg gccactggcc cagcctttga cactgcaagt   2760
cctagtggct ggcaaccccc aggacacacg cctccgatac agcttcttcg tgccccggcc   2820
gaccccttca acgccacgcc ccactcccca ggactggctg caccgaagag cacagattct   2880
ggagatcctt cggcggcgcc cctgggcggg caggaaataa cctcactatc ccggctgccc   2940
tttctgggca ccggggcctc ggacttagct gggagaaaga gagagcttct gttgctgcct   3000
catgctaaga ctcagtgggg aggggctgtg ggcgtgagac ctgcccctcc tctctgccct   3060
aatgcgcagg ctggccctgc cctggtttcc tgccctggga ggcagtgatg ggttagtgga   3120
tggaaggggc tgacagacag ccctccatct aaactgcccc ctctgccctg cgggtcacag   3180
gagggagggg gaaggcaggg agggcctggg ccccagttgt atttatttag tatttattca   3240
cttttattta gcaccaggga aggggacaag gactagggtc ctggggaacc tgacccctga   3300
cccctcatag ccctcaccct ggggctagga aatccagggt ggtggtgata ggtataagtg   3360
gtgtgtgtat gcgtgtgtgt gtgtgtgtga aaatgtgtgt gtgcttatgt atgaggtaca   3420
acctgttctg ctttcctctt cctgaatttt attttttggg aaaagaaaag tcaagggtag   3480
ggtgggcctt cagggagtga gggattatct tttttttttt ttctttcttt ctttcttttt   3540
```

-continued

```
ttttttttgag acagaatctc gctctgtcgc ccaggctgga gtgcaatggc acaatctcgg    3600
ctcactgcat cctccgcctc ccgggttcaa gtgattctca tgcctcagcc tcctgagtag    3660
ctgggattac aggctcctgc caccacgccc agctaatttt tgttttgttt tgtttggaga    3720
cagagtctcg ctattgtcac cagggctgga atgatttcag ctcactgcaa ccttcgccac    3780
ctgggttcca gcaattctcc tgcctcagcc tcccgagtag ctgagattat aggcacctac    3840
caccacgccc ggctaatttt tgtatttta gtagagacgg ggtttcacca tgttggccag    3900
gctggtctcg aactcctgac cttaggtgat ccactcgcct tcatctccca aagtgctggg    3960
attacaggcg tgagccaccg tgcctggcca cgcccaacta attttgtat ttttagtaga    4020
gacagggttt caccatgttg gccaggctgc tcttgaactc ctgacctcag gtaatcgacc    4080
tgcctcggcc tcccaaagtg ctgggattac aggtgtgagc caccgcccc ggtacatatt    4140
ttttaaattg aattctacta tttatgtgat cctttggag tcagacagat gtggttgcat    4200
cctaactcca tgtctctgag cattagattt ctcatttgcc aataataata cctcccttag    4260
aagtttgttg tgaggattaa ataatgtaaa taaagaacta gcataac                  4307

<210> SEQ ID NO 32
<211> LENGTH: 1726
<212> TYPE: DNA
<213> ORGANISM: Homo sapiens

<400> SEQUENCE: 32
atgtcccaga caggctcgca tcccggggagg ggcttggcag ggcgctggct gtggggagcc     60
caaccctgcc tcctgctccc cattgtgccg ctctcctggc tggtgtggct gcttctgcta    120
ctgctggcct ctctcctgcc ctcagcccgg ctggccagcc cctcccccg ggaggaggag    180
atcgtgtttc cagagaagct caacggcagc gtcctgcctg gctcgggcac ccctgccagg    240
ctgttgtgcc gcttgcaggc cttttgggag acgctgctac tagagctgga gcaggactcc    300
ggtgtgcagg tcgagggct gacagtgcag tacctgggcc aggcgcctga gctgctgggt    360
ggagcagagc ctggcaccta cctgactggc accatcaatg gagatccgga gtcggtggca    420
tctctgcact gggatggggg agccctgtta ggcgtgttac aatatcgggg ggctgaactc    480
cacctccagc ccctggaggg aggcacccct aactctgctg ggggacctgg ggctcacatc    540
ctacgccgga agagtcctgc cagcggtcaa ggtcccatgt gcaacgtcaa ggctcctctt    600
ggaagcccca gccccagacc ccgaagagcc aagcgctttg cttcactgag tagatttgtg    660
gagacactgg tggtggcaga tgacaagatg gccgcattcc acgtgcggg gctaaagcgc    720
tacctgctaa cagtgatggc agcagcagcc aaggccttca gcacccaag catccgcaat    780
cctgtcagct tggtggtgac tcggctagtg atcctggggt caggcgagga ggggccccaa    840
gtggggccca gtgctgccca gaccctgcgc agcttctgtg cctggcagcg gggcctcaac    900
acccctgagg actcggaccc tgaccacttt gacacagcca ttctgtttac ccgtcaggac    960
ctgtgtggag tctccacttg cgacacgctg ggtatggctg atgtgggcac cgtctgtgac   1020
ccggctcgga gctgtgccat tgtggaggat gatgggctcc agtcagcctt cactgctgct   1080
catgaactgg gtcatgtctt caacatgctc catgacaact ccaagccatg catcagtttg   1140
aatgggcctt tgagcacctc tcgccatgtc atggcccctg tgatggctca tgtggatcct   1200
gaggagccct ggtcccctg cagtgcccgc ttcatcactg acttcctgga caatggctat   1260
ggcactgtc tcttagacaa accagaggct ccattgcatc tgcctgtgac tttccctggc   1320
aaggactatg atgctgaccg ccagtgccag ctgacctcg ggcccgactc acgccattgt   1380
```

```
ccacagctgc cgccgccctg tgctgccctc tggtgctctg gccacctcaa tggccatgcc    1440
atgtgccaga ccaaacactc gccctgggcc gatggcacac cctgcgggcc cgcacaggcc    1500
tgcatgggtg gtcgctgcct ccacatggac cagctccagg acttcaatat tccacaggct    1560
ggtggctggg gtccttgggg accatggggt gactgctctc ggacctgtgg gggtggtgtc    1620
cagttctcct cccgagactg cacgaggcct gtccccggga atggtggcaa gtactgtgag    1680
ggccgccgta cccgcttccg ctcctgcaac actgaggact gcccaa                   1726
```

<210> SEQ ID NO 33
<211> LENGTH: 1561
<212> TYPE: DNA
<213> ORGANISM: Homo sapiens

<400> SEQUENCE: 33

```
atgtcccaga caggctcgca tcccgggagg ggcttggcag ggcgctggct gtggggagcc      60
caaccctgcc tcctgctccc cattgtgccg ctctcctggc tggtgtggct gcttctgcta     120
ctgctggcct ctctcctgcc ctcagccgg ctggccagcc cctcccccg ggaggaggag      180 atcgtgtttc cagagaagct caacggcagc gtcctgcctg gctcgggcac ccctgccagg     240
ctgttgtgcc gcttgcaggc cttggggag acgctgctac tagagctgga gcaggactcc     300
ggtgtgcagg tcgagggct gacagtgcag tacctgggcc aggcgcctga gctgctgggt     360
ggagcagagc ctggcaccta cctgactggc accatcaatg gagatccgga gtcggtggca     420
tctctgcact gggatggggg agccctgtta ggcgtgttac aatatcgggg ggctgaactc     480
cacctccagc ccctggaggg aggcacccct aactctgctg ggggacctgg ggctcacatc     540
ctacgccgga agagtcctgc cagcggtcaa ggtcccatgt gcaacgtcaa ggctcctctt     600
ggaagcccca gccccagacc ccgaagagcc aagcgctttg cttcactgag tagatttgtg     660
gagacactgg tggtggcaga tgacaagatg gccgcattcc acggtgcggg gctaaagcgc     720
tacctgctaa cagtgatggc agcagcagcc aaggccttca gcacccaag catccgcaat     780 cctgtcagct tggtggtgac tcggctagtg atcctggggt caggcgagga ggggccccaa     840
gtggggccca gtgctgccca gaccctgcgc agcttctgtg cctggcagcg gggcctcaac     900 accctgagg actcggaccc tgaccacttt gacacagcca ttctgtttac ccgtcaggac     960
ctgtgtggag tctccacttg cgacacgctg gtatggctg atgtgggcac cgtctgtgac    1020
ccggctcgga gctgtgccat tgtggaggat gatgggctcc agtcagcctt cactgctgct    1080
catgaactgg gtcatgtctt caacatgctc atgacaact ccaagccatg catcagtttg    1140
aatgggcctt tgagcacctc tcgccatgtc atggcccctg tgatggctca tgtggatcct    1200 gaggagccc ggtccccctg cagtgccgc ttcatcactg acttcctgga caatggctat    1260 ggcactgtc tcttagacaa accagaggct ccattgcatc tgcctgtgac tttccctggc    1320
aaggactatg atgctgaccg ccagtgccag ctgaccttcg gcccgactc acgccattgt    1380 ccacagctgc cgccgccctg tgctgccctc tggtgctctg gccacctcaa tggccatgcc    1440
atgtgccaga ccaaacactc gccctgggcc gatggcacac cctgcgggcc cgcacaggcc    1500
tgcatgggtg gtcgctgcct ccacatggac cagctccagg acttcaatat tccacaggct    1560
g                                                                   1561
```